(12) United States Patent
Scott et al.

(10) Patent No.: US 8,969,588 B2
(45) Date of Patent: Mar. 3, 2015

(54) SOLID FORMS OF AN ANTIVIRAL COMPOUND

(71) Applicant: Gilead Pharmasset LLC, Foster City, CA (US)

(72) Inventors: Robert William Scott, San Mateo, CA (US); Fang Wang, Foster City, CA (US); Bing Shi, Redwood City, CA (US); Erik Mogalian, San Francisco, CA (US)

(73) Assignee: Gilead Pharmasset LLC, Foster City, CA (US)

( * ) Notice: Subject to any disclaimer, the term of this patent is extended or adjusted under 35 U.S.C. 154(b) by 0 days.

(21) Appl. No.: 13/800,374

(22) Filed: Mar. 13, 2013

(65) Prior Publication Data

US 2013/0324496 A1    Dec. 5, 2013

Related U.S. Application Data

(60) Provisional application No. 61/655,934, filed on Jun. 5, 2012, provisional application No. 61/759,295, filed on Jan. 31, 2013.

(51) Int. Cl.
| | | |
|---|---|---|
| *C07D 403/14* | (2006.01) | |
| *A61K 31/4184* | (2006.01) | |
| *A61K 31/7056* | (2006.01) | |
| *A61K 31/381* | (2006.01) | |
| *C07D 471/08* | (2006.01) | |

(52) U.S. Cl.
CPC .......... *A61K 31/4184* (2013.01); *C07D 403/14* (2013.01); *A61K 31/7056* (2013.01); *A61K 31/381* (2013.01); *C07D 471/08* (2013.01)
USPC ....................................... 548/300.7; 514/394

(58) Field of Classification Search
USPC ...................................................... 548/300.7
See application file for complete search history.

(56) References Cited

U.S. PATENT DOCUMENTS

| | | |
|---|---|---|
| 8,088,368 B2 | 1/2012 | Guo et al. |
| 8,273,341 B2 | 9/2012 | Guo et al. |
| 8,575,118 B2 | 11/2013 | Guo et al. |
| 8,669,234 B2 | 3/2014 | Guo et al. |
| 2013/0324740 A1 | 12/2013 | Scott et al. |
| 2014/0039021 A1 | 2/2014 | Bacon et al. |
| 2014/0051656 A1 | 2/2014 | Bacon et al. |

FOREIGN PATENT DOCUMENTS

| | | |
|---|---|---|
| WO | WO2010/132601 | 11/2010 |
| WO | WO2011/156757 | 12/2011 |

OTHER PUBLICATIONS

U.S. Appl. No. 14/280,478, filed May 16, 2014, Bacon et al.
Guillory, J.K., "Generation of Polymorphs, Hydrates, Solvates, and Amorphous Solids," Polymorphism in Pharmaceutical Solids, edited by Harry G. Brittain, Marcel Decker, Inc., Milford, New Jersey (1999).
Caira, M.R., "Crystalline Polymorphism of Organic Compounds," Topics in Current Chemistry, 198, 163-208 (1998).
Hilfiker, R., et al., "Relevance of Solid-state Properties for Pharmaceutical Products," Polymorphism in the Pharmaceutical Industry, edited by Rolf Hilfiker, 1-19, (2006).
International Search Report and Written Opinion from PCT/US2013/044138, mailed October 15, 2013.
Lawitz, E.J., et al., "A phase 1, randomized, placebo-controlled, 3-day, dose-ranging study of GS-5885, an NS5A inhibitor, in partients with genotype 1 hepatitis C," Journal of Hepatology, 57(1), 24-31 (2012).

*Primary Examiner* — Laura L. Stockton
(74) *Attorney, Agent, or Firm* — J. Elin Hartrum; Brian C. Remy

(57) ABSTRACT

Amorphous and crystalline solid forms of the anti-HCV compound (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester (Compound I) were prepared and characterized in the solid state:

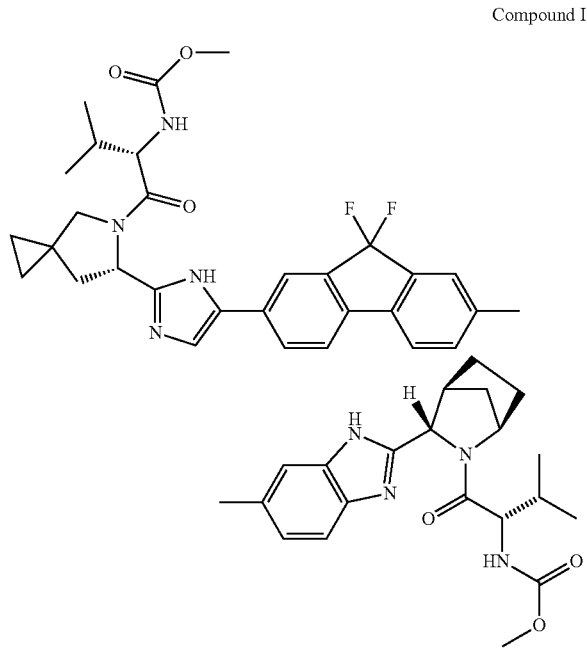

Compound I

Also provided are processes of manufacture and methods of using the amorphous and crystalline forms.

17 Claims, 36 Drawing Sheets

SOLID FORMS OF AN ANTIVIRAL COMPOUND

CROSS REFERENCE TO RELATED APPLICATIONS

This application claims the benefit under 35 U.S.C. §119(e) to U.S. Provisional Application Ser. No. 61/655,934 filed on Jun. 5, 2012 and U.S. Provisional Application Ser. No. 61/759,295, filed on Jan. 31, 2013, the entirety of both of which is incorporated herein by reference.

BACKGROUND

The present disclosure relates generally to crystalline solid forms of the antiviral compound (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester, processes for making the forms, and their therapeutic methods of use.

Hepatitis C is recognized as a chronic viral disease of the liver which is characterized by liver disease. Although drugs targeting the liver are in wide use and have shown effectiveness, toxicity and other side effects have limited their usefulness. Inhibitors of hepatitis C virus (HCV) are useful to limit the establishment and progression of infection by HCV as well as in diagnostic assays for HCV.

The compound (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester, also known as ledipasvir, designated herein as Compound I, is known to be an effective anti-HCV agent, as described for example in WO 2010/132601. A synthesis of compound I is disclosed in U.S. Pat. No. 8,088,368. However, Compound I was not heretofore known in any solid crystalline form.

SUMMARY

The present disclosure fulfills these needs and others by providing crystalline forms of Compound I, salts, and solvates. The present disclosure also provides an amorphous form of Compound I. The present disclosure also provides pharmaceutical compositions comprising amorphous and crystalline forms of Compound I. The disclosure also provides processes for making the amorphous and crystalline forms and methods for using them in the treatment of HCV.

Thus, one embodiment is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester diacetone solvate (Compound I Form I). Compound I Form I is characterized by an X-ray powder diffractogram comprising the following peaks: 6.8, 12.5, and 19.8° 2θ±0.2° 2θ, as determined on a diffractometer using Cu-Kα radiation at a wavelength of 1.54178 Å.

Another embodiment is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester monoacetone solvate (Compound I Form II). Compound I Form II is characterized by an X-ray powder diffractogram comprising the following peaks: 12.2, 12.7, and 20.5° 2θ±0.2° 2θ, as determined on a diffractometer using Cu-Kα radiation at a wavelength of 1.54178 Å.

An additional embodiment is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester (Compound I Form III). Compound I Form III is characterized by an X-ray powder diffractogram comprising the following peaks: 12.4, 14.2, and 21.6° 2θ±0.2° 2θ, as determined on a diffractometer using Cu-Kα radiation at a wavelength of 1.54178 Å.

Still another embodiment is crystalline -(1-{3[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester D-tartrate (Compound I D-tartrate). Compound I D-tartrate is characterized by an X-ray powder diffractogram comprising the following peaks: 4.0, 10.3, and 19.7° 2θ±0.2°θ, as determined on a diffractometer using Cu-Kα radiation at a wavelength of 1.54178 Å.

Another embodiment is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester ethyl acetate solvate (Compound I Form IV), characterized by an X-ray powder diffractogram comprising the following peaks: 15.1, 17.2, and 21.5° 2θ±0.2° 2θ, as determined on a diffractometer using Cu-Kα radiation at a wavelength of 1.54178 Å.

Still another embodiment is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester ethyl acetate solvate (Compound I Form V), characterized by an X-ray powder diffractogram comprising the following peaks: 14.4, 15.3, and 17.4°2θ±0.2° 2θ, as determined on a diffractometer using Cu-Kα radiation at a wavelength of 1.54178 Å. Compound I Form V is a partial ethyl acetate solvate.

Another embodiment is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester isopropyl acetate solvate (Compound I Form VI), characterized by an X-ray powder diffractogram comprising the following peaks: 5.6, 13.3, and 21.1° 2θ±0.2° 2θ, as determined on a diffractometer using Cu-Kα radiation at a wavelength of 1.54178 Å.

In accordance with an additional embodiment, the present disclosure provides crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester methyl acetate solvate (Compound I Form VII), characterized by an X-ray powder diffractogram comprising the following peaks: 11.0, 13.8, and 22.2° 2θ±0.2° 2θ, as determined on a diffractometer using Cu-Kα radiation at a wavelength of 1.54178 Å.

Still another embodiment is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester (Compound I Form VIII), characterized by an X-ray powder diffractogram comprising the following peaks: 9.4, 15.5, and 17.5° 2θ±0.2° 2θ, as determined on a diffractometer using Cu-Kα radiation at a wavelength of 1.54178 Å.

One embodiment is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester ethyl formate solvate (Compound I Form IX), characterized by an X-ray powder diffractogram comprising the following peaks: 13.8, 19.2, and 22.0°2θ±0.2° 2θ, as determined on a diffractometer using Cu-Kα radiation at a wavelength of 1.54178 Å.

Another embodiment is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester acetonitrile solvate (Compound I Form X), characterized by an X-ray powder diffractogram comprising the following peaks: 3.4, 6.9, and 10.3° 2θ±0.2° 2θ, as determined on a diffractometer using Cu-Kα radiation at a wavelength of 1.54178 Å.

Yet a further embodiment is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester tetrahydrofuran solvate (Compound I Form XI), characterized by an X-ray powder diffractogram comprising the following peaks: 3.2, 6.3, and 9.5° 2θ±0.2° 2θ, as determined on a diffractometer using Cu-Kα radiation at a wavelength of 1.54178 Å.

Another embodiment is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester methyl ethyl ketone solvate (Compound I Form XII), characterized by an X-ray powder diffractogram comprising the following peaks: 3.2, 6.4, and 20.6° 2θ±0.2° 2θ, as determined on a diffractometer using Cu-Kα radiation at a wavelength of 1.54178 Å.

Still another embodiment is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester tetrahydrofuran solvate (Compound I Form XIII-THF), characterized by an X-ray powder diffractogram comprising the following peaks: 3.2, 3.5, and 7.0° 2θ±0.2° 2θ, as determined on a diffractometer using Cu-Kα radiation at a wavelength of 1.54178 Å. Compound I Form XIII-THF is a partial THF solvate.

An alternative is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester methyl ethyl ketone solvate (Compound I Form XIII-MEK), characterized by an X-ray powder diffractogram comprising the following peaks: 3.2, 3.5, and 7.0° 2θ±0.2° 2θ, as determined on a diffractometer using Cu-Kα radiation at a wavelength of 1.54178 Å. Compound I Form XIII-MEK is a partial MEK solvate.

In another embodiment, the present disclosure provides crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester methyl tert-butyl ether solvate (Compound I Form XIV), characterized by an X-ray powder diffractogram comprising the following peaks: 6.9, 10.3, and 22.4° 2θ±0.2° 2θ, as determined on a diffractometer using Cu-Kα radiation at a wavelength of 1.54178 Å.

Still another embodiment is crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester (Compound I Form XV), characterized by an X-ray powder diffractogram comprising the following peaks: 12.1, 12.8, and 20.8° 2θ±0.2° 2θ, as determined on a diffractometer using Cu-Kα radiation at a wavelength of 1.54178 Å.

Still another embodiment is amorphous 1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester, characterized by a glass transition temperature (Tg) of about 160° C.

Still another embodiment is a pharmaceutical composition comprising a crystalline or amorphous form of Compound I and a pharmaceutically acceptable excipient.

One embodiment is a composition comprising at least two of Compound I Form I, Compound I Form II, Compound I Form III, and Compound I D-tartrate.

Additionally, the disclosure provides in one embodiment a method for treating a subject suffering from hepatitis C virus (HCV). The method comprises administering to the subject a therapeutically effective amount of any one of amorphous Compound I, Compound I Forms I-XV and Compound I D-tartrate, as described generally above.

Another embodiment, optionally in combination with any other embodiment described herein, is the use of any one of Compound I Forms I-XV and Compound I D-tartrate for treating HCV in a subject suffering therefrom.

Still an additional embodiment, optionally in combination with any other embodiment described herein, is the use of any one of Compound I Forms I-XV and Compound I D-tartrate in the manufacture of a medicament for treating HCV in a subject suffering therefrom.

In another embodiment, the disclosure provides a process for making Compound I Form I. The process comprises the step of contacting amorphous Compound I with acetone, whereby a Compound I Form I is formed.

Still another embodiment is a process for making Compound I Form II. The process comprises the step of partially desolvating Compound I Form I, whereby Compound I Form II is formed.

Another embodiment is a process for making Compound I Form III. The process comprises the step of heating Compound I Form II to about 30-120° C., whereby Compound I Form III is formed.

The disclosure provides in another embodiment a process for making Compound I D-tartrate as described above. The process comprises the step of contacting D-tartaric acid with a solution Compound I in a solvent, whereby Compound I D-tartrate is formed.

Also provided is a process for making Compound I Form IV. The process comprises the step of contacting Compound I Form III with ethyl acetate.

In another embodiment, the present disclosure provides a process for making Compound I Form V. The process comprises the step of desolvating Compound I Form IV. Compound I Form V is a partial ethyl acetate solvate.

Another embodiment is a process for making Compound I Form VI. The process comprises the step of contacting Compound I Form III with isopropyl acetate.

Still another embodiment is a process for making Compound I Form VII. The process comprises the step of contacting Compound I Form III with methyl acetate.

This disclosure provides in another embodiment a process for making Compound I Form VIII. The process comprises the step of desolvating Compound I Form VII.

One embodiment is a process for making Compound I Form IX. The process comprises the step of contacting Compound I Form III with ethyl formate.

Another embodiment is a process for making Compound I Form X. The process comprises the step of contacting Compound I Form III with acetonitrile.

Still another embodiment is a process for making Compound I Form XI. The process comprises the step of contacting Compound I Form III with tetrahydrofuran.

Additionally, the present disclosure provides a process for making Compound I Form XII. The process comprises the step of contacting Compound I Form III with methyl ethyl ketone.

Another embodiment is a process for making Compound I Form XIII-THF. The process comprises the step of desolvating Compound I Form XI. Compound I Form XIII-THF is a partial THF solvate.

Also, the disclosure provides a process for making Compound I Form XIII-MEK. The process comprises the step of desolvating Compound I Form XII. Compound I Form XIII-MEK is a partial MEK solvate.

In still another embodiment, the present disclosure provides a process for making Compound I Form XIV. The process comprises the step of contacting Compound I Form VIII with methyl tert-butyl ether.

In addition, the present disclosure provides a process for making Compound I Form XV. The process comprises the step of desolvating Compound I Form X.

In still another embodiment, the present disclosure provides a process for making amorphous Compound I as outlined in Example 10.

DETAILED DESCRIPTION

Figure 1:
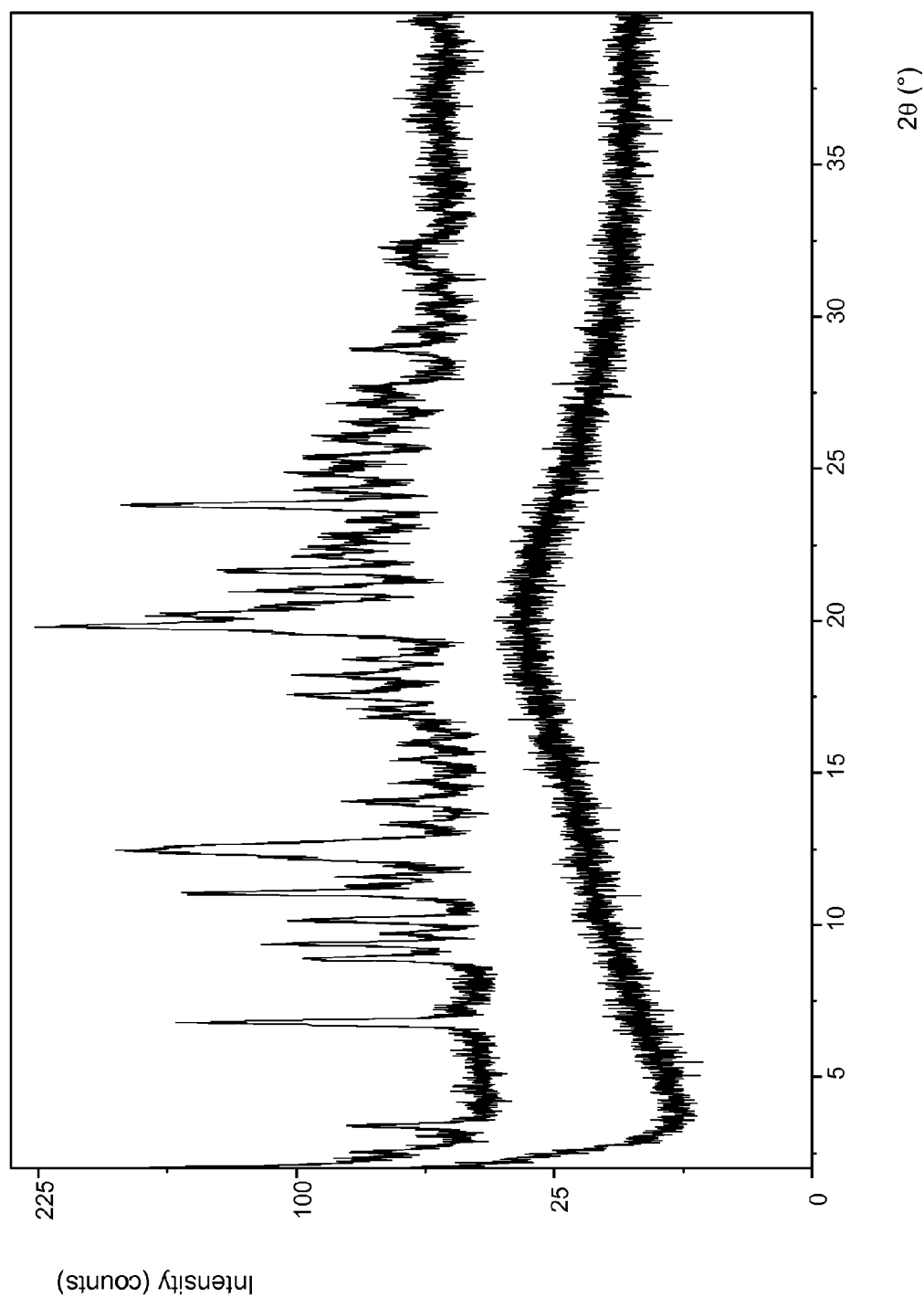
FIG. 1 is a comparison between the XRPD patterns of amorphous Compound I (bottom curve) and Compound I Form I (top curve), respectively.

The compound (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester (Compound I) is a selective and potent inhibitor of HCV NS5A.

ecules have been partially or completely removed. Desolvation techniques to produce desolvated forms include, without limitation, exposure of a Compound I form (solvate) to a vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially solvated wherein solvent molecules are present in stoichiometric or non-stoichiometric amounts.

Any formula or structure given herein, including Compound I, is also intended to represent unlabeled forms as well as isotopically labeled forms of the compounds. Isotopically labeled compounds have structures depicted by the formulae given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium D) $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

Compound I

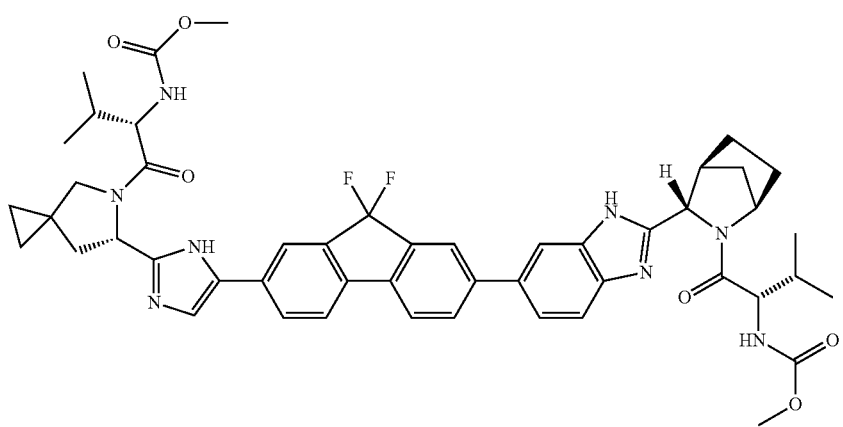

One embodiment is an amorphous form of Compound I. The physicochemical properties of this form include a high glass transition temperature (Tg) of about 160° C. and suitable powder properties for oral dosage. Accordingly, tablet formulations were developed using this form as discussed in Examples 11 and 12 below. In some instances, it is desirable to employ an amorphous version of the drug for improved solubility and bioavailability properties. In other instances, it is desirable to have the drug in crystalline form for improved stability.

Definitions

As used in the present specification, the following words and phrases are generally intended to have the meanings as set forth below, except to the extent that the context in which they are used indicates otherwise.

The term "solvate" refers to a complex formed by the combining of Compound I and a solvent.

The term "desolvated" refers to a Compound I form that is a solvate as described herein, and from which solvent mol- The disclosure also includes Compound I in which from 1 to "n" hydrogens attached to a carbon atom is/are replaced by deuterium, in which n is the number of hydrogens in the molecule. Such compounds exhibit increased resistance to metabolism and are thus useful for increasing the half life of any Compound I when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to absorption, distribution, metabolism and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in Compound I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The term "therapeutically effective amount" refers to an amount that is sufficient to effect treatment, as defined below, when administered to a mammal in need of such treatment. The therapeutically effective amount will vary depending upon the subject being treated, the weight and age of the subject, the severity of the disease condition, the manner of administration and the like, which can readily be determined by one of ordinary skill in the art.

The term "about" refers to a range of ±10%, unless otherwise specified.

In addition, abbreviations as used herein have respective meanings as follows:

| | |
|---|---|
| 2-Me THF | 2 methyl tetrahydrofuran |
| ACN or MeCN | acetonitrile |
| AcOH | acetic acid |
| AN | area normalized |
| Boc | tert-butoxycarbonyl |
| d | doublet |
| DCM | dichloromethane |
| dd | doublet of doublets |
| ddd | doublet of doublet of doublets |
| DMAC | dimethylacetamide |
| DMF | dimethylformamide |
| DMSO | dimethylsulfoxide |
| DSC | Differential scanning calorimetry |
| DVS | Dynamic vapor sorption |
| EDC | 1-ethyl-3-(3-dimethylaminopropyl) carbodiimide |
| eq or equiv | equivalents |
| EtOAc | ethyl acetate |
| EtOH | ethanol |
| g | gram |
| HCV | Hepatitis C virus |
| HPLC | high performance liquid chromatography |
| HPMC | hydroxypropyl methylcellulose |
| HRMS | high resolution mass spectroscopy |
| IPAc or iPrOAc | isopropyl acetate |
| i-PrMgCl | isopropyl magnesium chloride |
| iPrOH | isopropanol |
| L | liter |
| LiHMDS | lithium hexamethyldisilazide |
| m | multiplet |
| MEK | methyl ethyl ketone |
| MeOH | methanol |
| MIBK | methyl iso-butyl ketone |
| mL | milliliter |
| MTBE | methyl tert-butyl ether |
| NH$_4$OAc | ammonium acetate |
| NMR | nuclear magnetic resonance |
| PPh$_3$ | triphenylphosphine |
| PLM | polarized light microscopy |
| RH | relative humidity |
| RRT | relative retention time |
| s | singlet |
| t | triplet |
| tBuOK | potassium tert-butoxide |
| TFA | trifluoroacetic acid |
| TGA | thermogravimetric analysis |
| THF | tetrahydrofuran |
| μL | microliter |
| XRPD | X-ray powder diffraction |

Solid Forms of Compound I

As described generally above, the present disclosure provides solid crystalline forms of Compound I designated as Forms I-XV and D-tartrate. The inventors surprisingly discovered that these forms give rise to a number of technical advantages over the amorphous form of Compound I as explained, for instance, throughout the working examples and figures herein.

Compound I Form I is characterized by its X-ray powder diffractogram that comprises peaks at 6.8, 12.5, and 19.8° 2θ±0.2° 2θ, as determined on a diffractometer using Cu-Kα radiation at a wavelength of 1.54178 Å. The diffractogram comprises additional peaks at 10.2, 11.1, and 23.8° 2θ±0.2° 2θ. Form I also is characterized by its full X-ray powder diffractogram as substantially shown in FIG. 2.

Figure 3:
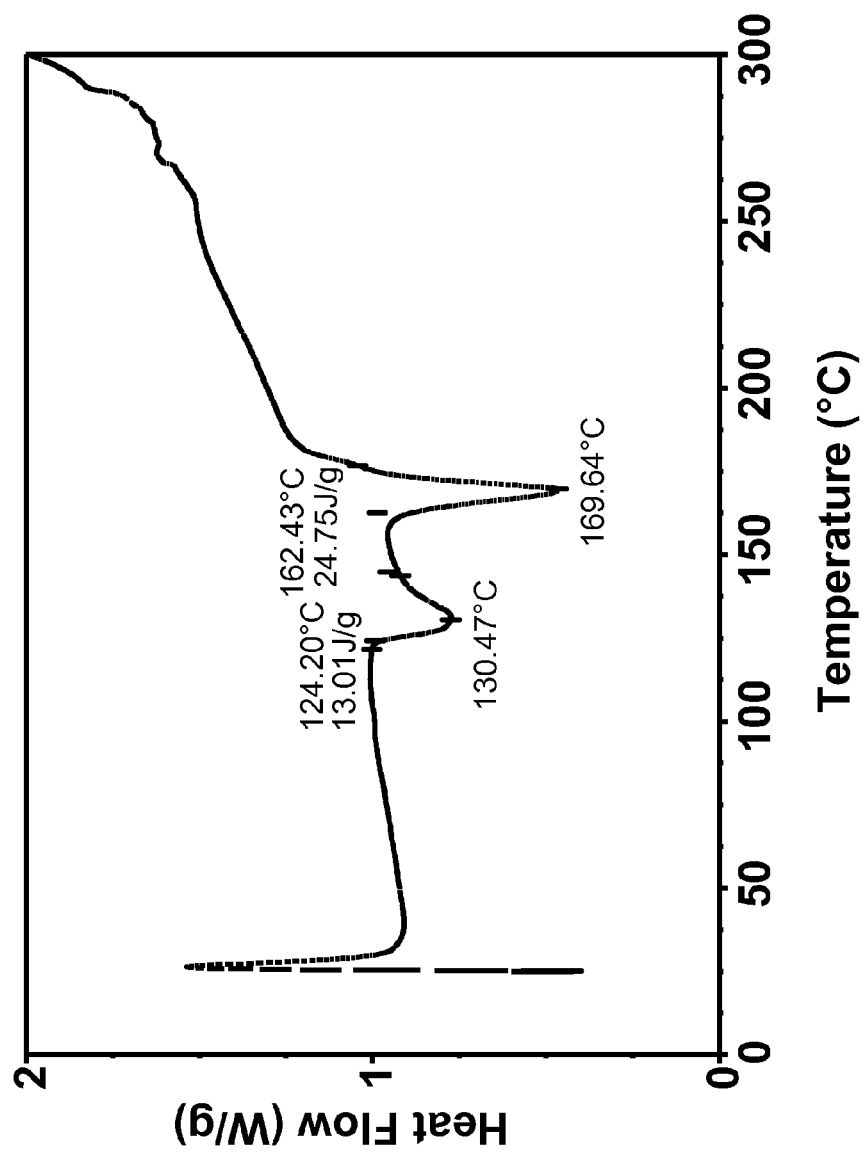
FIG. 3 is differential scanning calorimetry (DSC) curve of Compound I Form I.

In some embodiments, Form I is characterized by its differential scanning calorimetry (DSC) curve that comprises a minor endotherm at about 124° C. and a major endotherm at about 162° C. Form I also is characterized by its full DSC curve as substantially as shown in FIG. 3.

Figure 4:
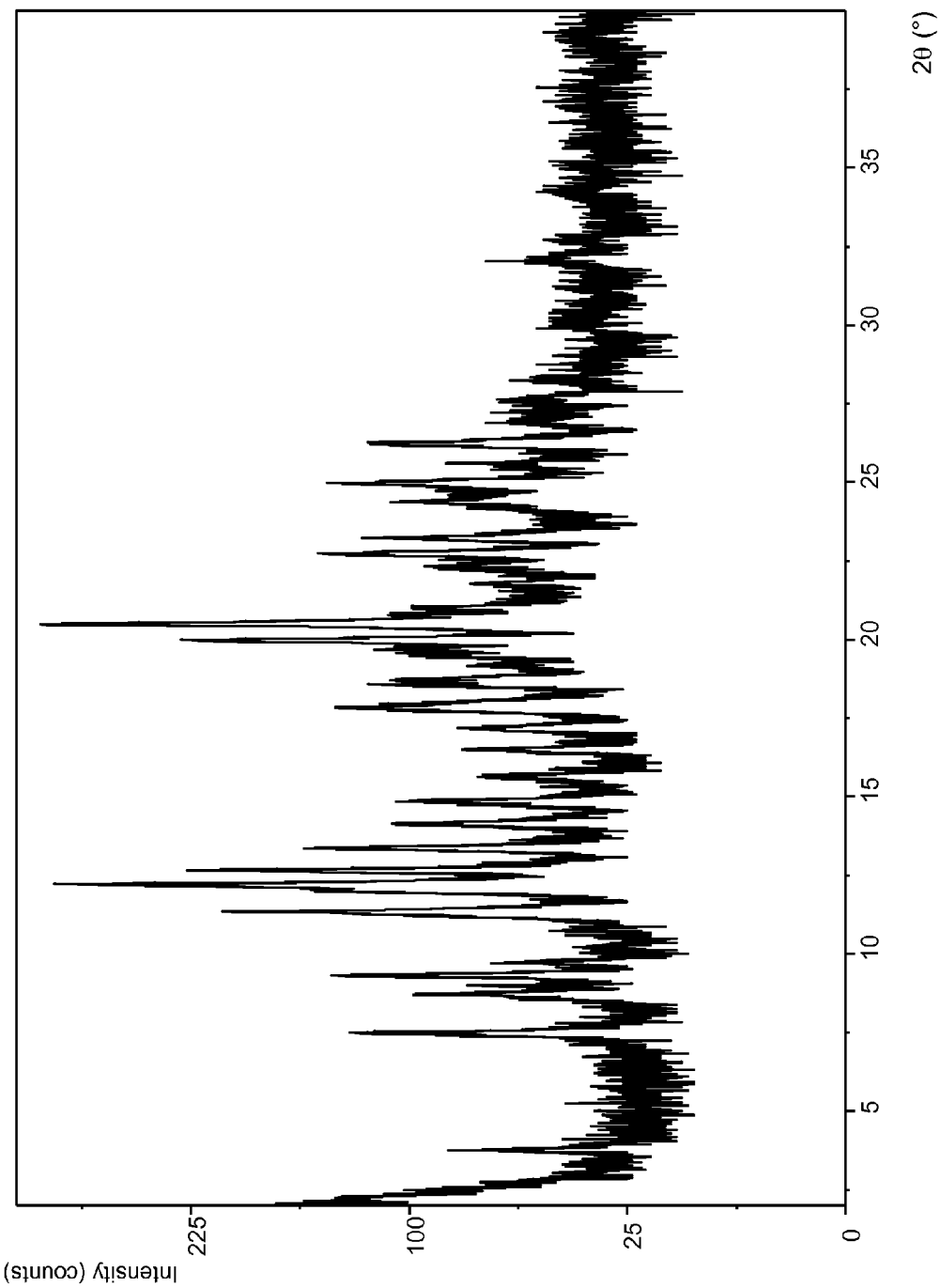
FIG. 4 is an X-ray powder diffraction pattern of Compound I Form II.

Compound I Form II similarly is characterized by its X-ray powder diffractogram that peaks at 12.2, 12.7, and 20.5° 2θ±0.2° 2θ, as determined on a diffractometer using Cu-Kα radiation at a wavelength of 1.54178 Å. The diffractogram comprises additional characteristic peaks at 7.5, 11.4, and 20.0° 2θ±0.2° 2θ. Alternatively, Form II is characterized by its X-ray powder diffractogram substantially as shown in FIG. 4.

Figure 5:
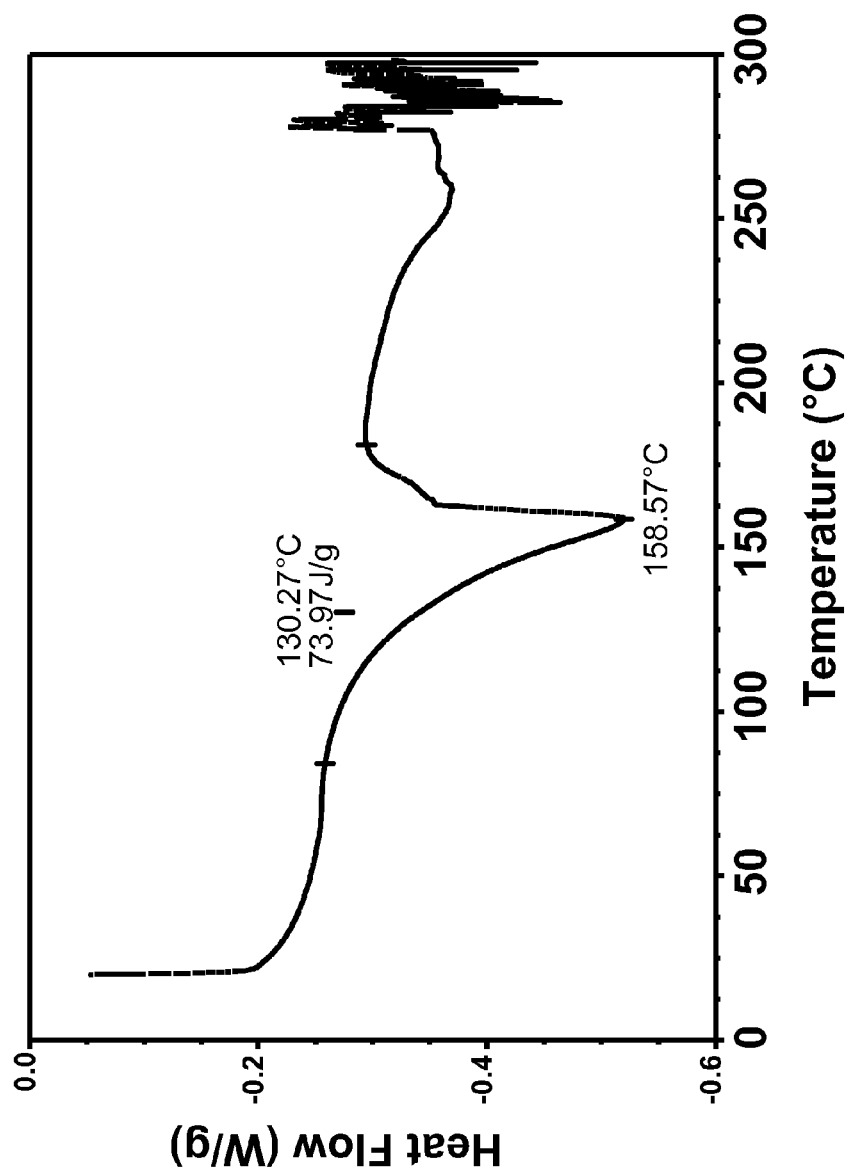
FIG. 5 is differential scanning calorimetry (DSC) curve of Compound I Form II.

In some embodiments, Form II is characterized by its DSC curve that comprises an endotherm at about 130° C. In other embodiments, Form II is characterized by its full DSC curve substantially as shown in FIG. 5.

Figure 7:
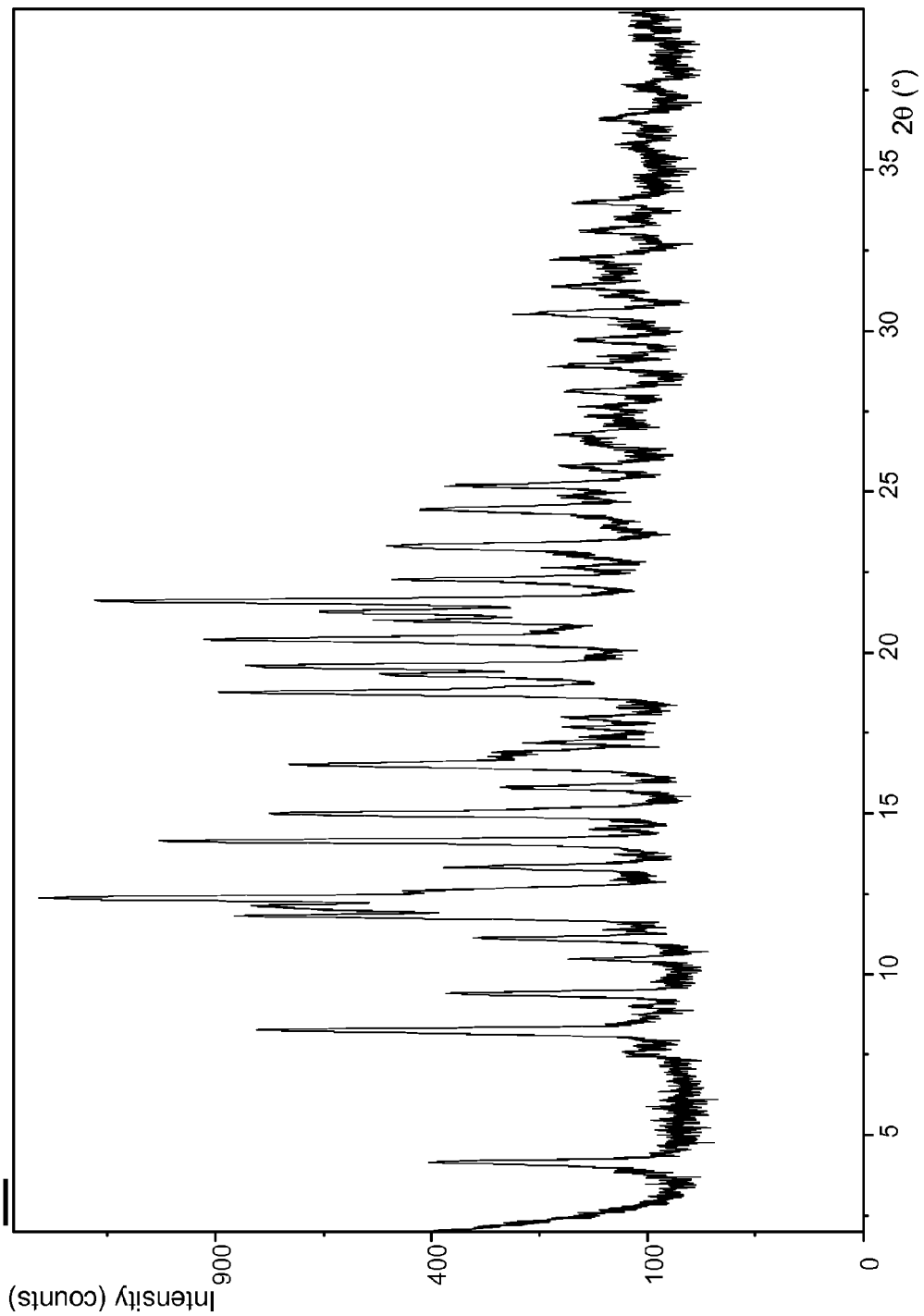
FIG. 7 is an X-ray powder diffraction pattern of Compound I Form III.

Compound I Form III is characterized by its X-ray powder diffractogram that comprises peaks at 12.4, 14.2, and 21.6° 2θ±0.2° 2θ, as determined on a diffractometer using Cu-Kα radiation at a wavelength of 1.54178 Å. The diffractogram for Form III comprises additional characteristic peaks at 8.3, 15.0, and 20.4° 2θ±0.2° 2θ. Form III also is characterized by its full X-ray powder diffractogram that is substantially as shown in FIG. 7.

In some embodiments, Form III is characterized by its DSC curve that comprises an endotherm at about 176° C. Alternatively, Form III is characterized by its full DSC curve as substantially shown in FIG. 8.

Crystalline Compound I D-tartrate according to this disclosure is characterized in one embodiment by its X-ray powder diffractogram that comprises peaks at 4.0, 10.3, and 19.7°2θ±0.2° 2θ, as determined on a diffractometer using Cu-Kα radiation at a wavelength of 1.54178 Å. Additional characterizing peaks occur at 9.1, 12.7, and 24.0° 2θ±0.2° 2θ. Alternatively, Compound I D-tartrate is characterized by its full X-ray powder diffractogram as substantially shown in FIG. 9.

In some embodiments, Compound I D-tartrate is characterized by its DSC curve that comprises an endotherm at about 221° C. Alternatively, Compound I D-tartrate is characterized by its full DSC curve as substantially shown in FIG. 10.

Compound I Form IV is characterized by an X-ray powder diffractogram comprising peaks at 15.1, 17.2, and 21.5° 2θ±0.2° 2θ, as determined on a diffractometer using Cu-Kα radiation at a wavelength of 1.54178 Å. Additional characterizing peaks occur at 5.6, 13.5, and 25.8° 2θ±0.2° 2θ. Compound I Form IV is further characterized by its XRPD diffractogram as substantially shown in FIG. 14.

Alternatively, Compound I Form IV is characterized by a differential scanning calorimetry (DSC) curve that comprises an endotherm at about 167° C. Compound I Form IV also is characterized by its full DSC curve as substantially shown in FIG. 15.

Compound I Form V is characterized by an X-ray powder diffractogram comprising characterizing peaks at 14.4, 15.3, and 17.4° 2θ±0.2° 2θ, as determined on a diffractometer using Cu-Kα radiation at a wavelength of 1.54178 Å. The diffractogram further comprises peaks at 8.6, 11.8, and 18.9° 2θ±0.2° 2θ. Compound I Form V also is characterized by its full XRPD diffractogram as substantially shown in FIG. 16.

Figure 17:
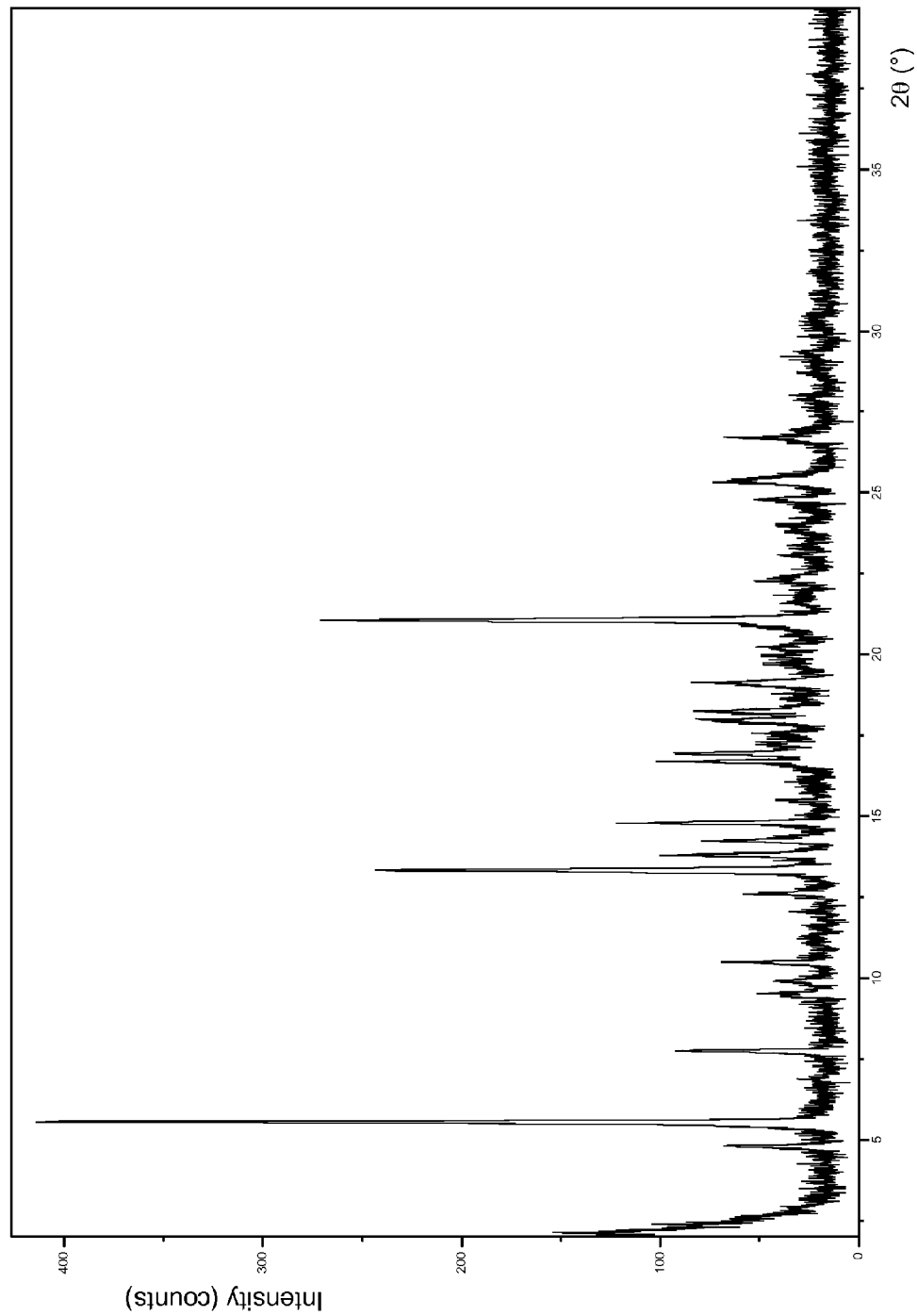
FIG. 17 is an X-ray powder diffraction pattern of Compound I Form VI.

Compound I Form VI is characterized by an X-ray powder diffractogram comprising peaks at 5.6, 13.3, and 21.1° 2θ±0.2° 2θ, as determined on a diffractometer using Cu-Kα radiation at a wavelength of 1.54178 Å. The diffractogram further comprises peaks at 13.8, 14.8, and 16.9° 2θ±0.2° 2θ. Compound I Form VI also is characterized by its full diffractogram substantially as shown in FIG. 17.

Figure 18:
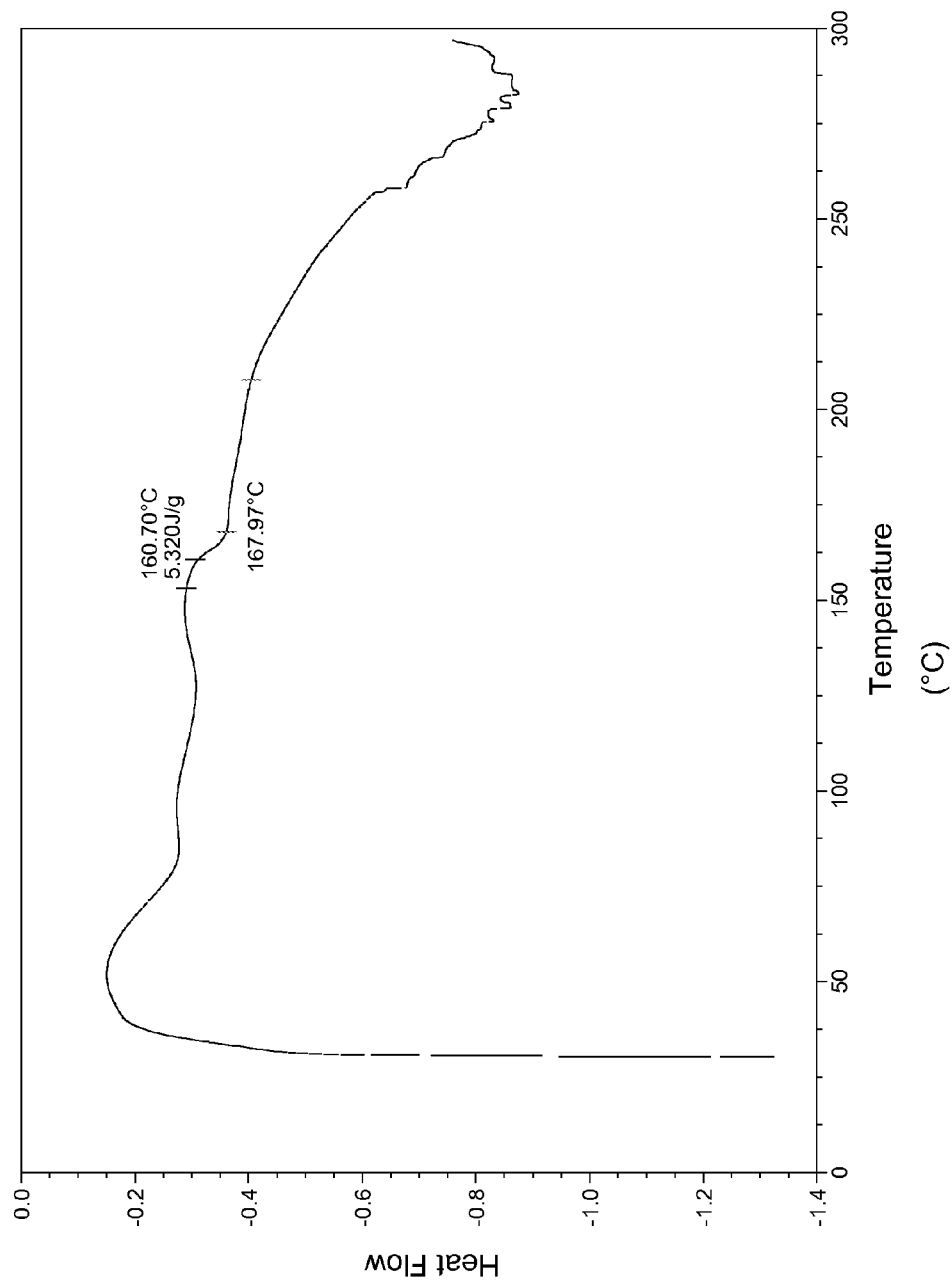
FIG. 18 is differential scanning calorimetry (DSC) curve of Compound I Form VI.

Alternatively, Compound I Form VI is characterized by a differential scanning calorimetry (DSC) curve that comprises an endotherm at about 168° C. In addition, Form VI is characterized by its full DSC curve substantially as shown in FIG. 18.

Figure 19:
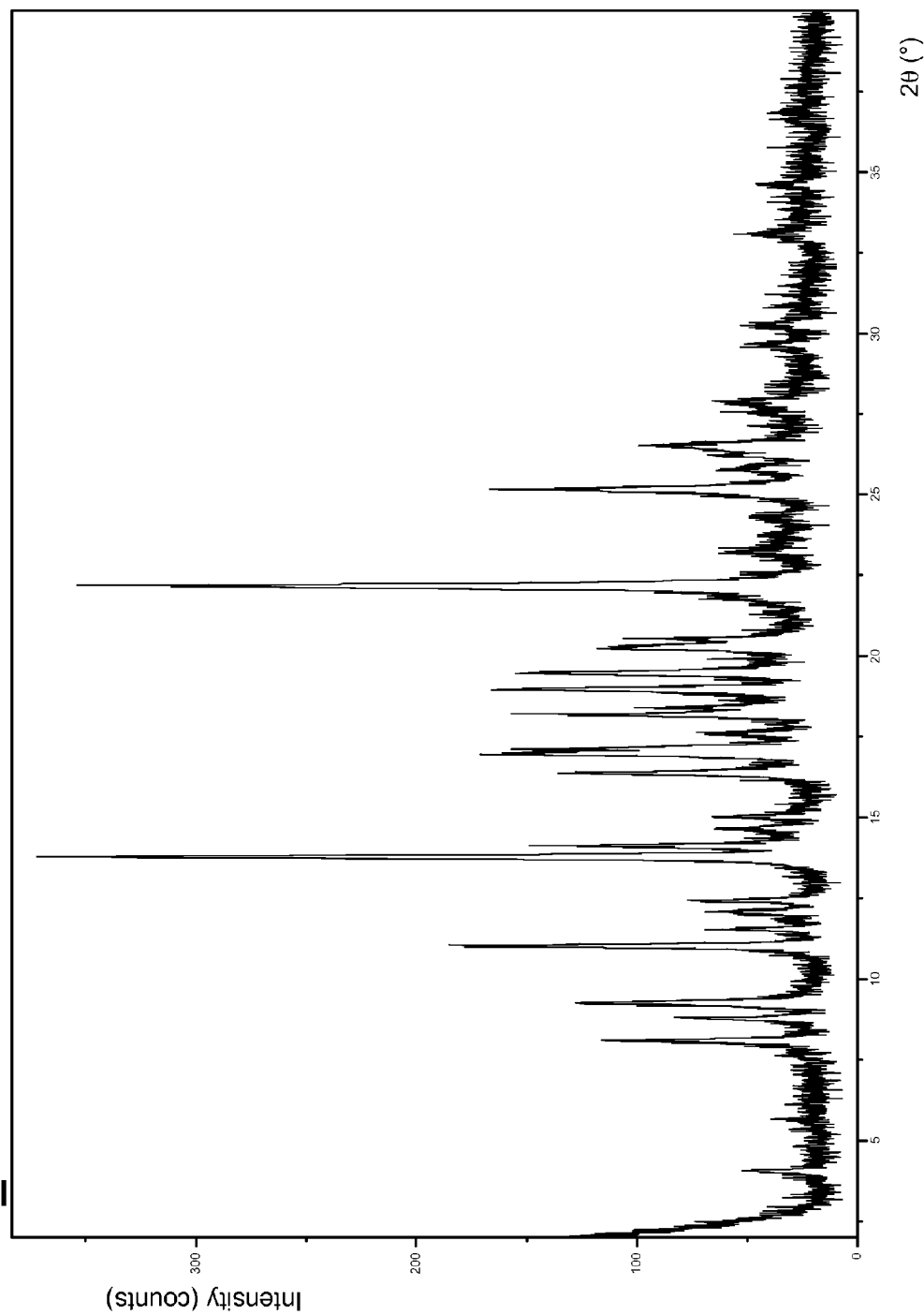
FIG. 19 is an X-ray powder diffraction pattern of Compound I Form VII.

Compound I Form VII is characterized by an X-ray powder diffractogram comprising peaks at 11.0, 13.8, and 22.2° 2θ±0.2° 2θ, as determined on a diffractometer using Cu-Kα radiation at a wavelength of 1.54178 Å. The diffractogram further comprises peaks at 17.0, 19.0, and 19.4° 2θ±0.2° 2θ. Compound I Form VII also is characterized by its XRPD diffractogram substantially as shown in FIG. 19.

Figure 20:
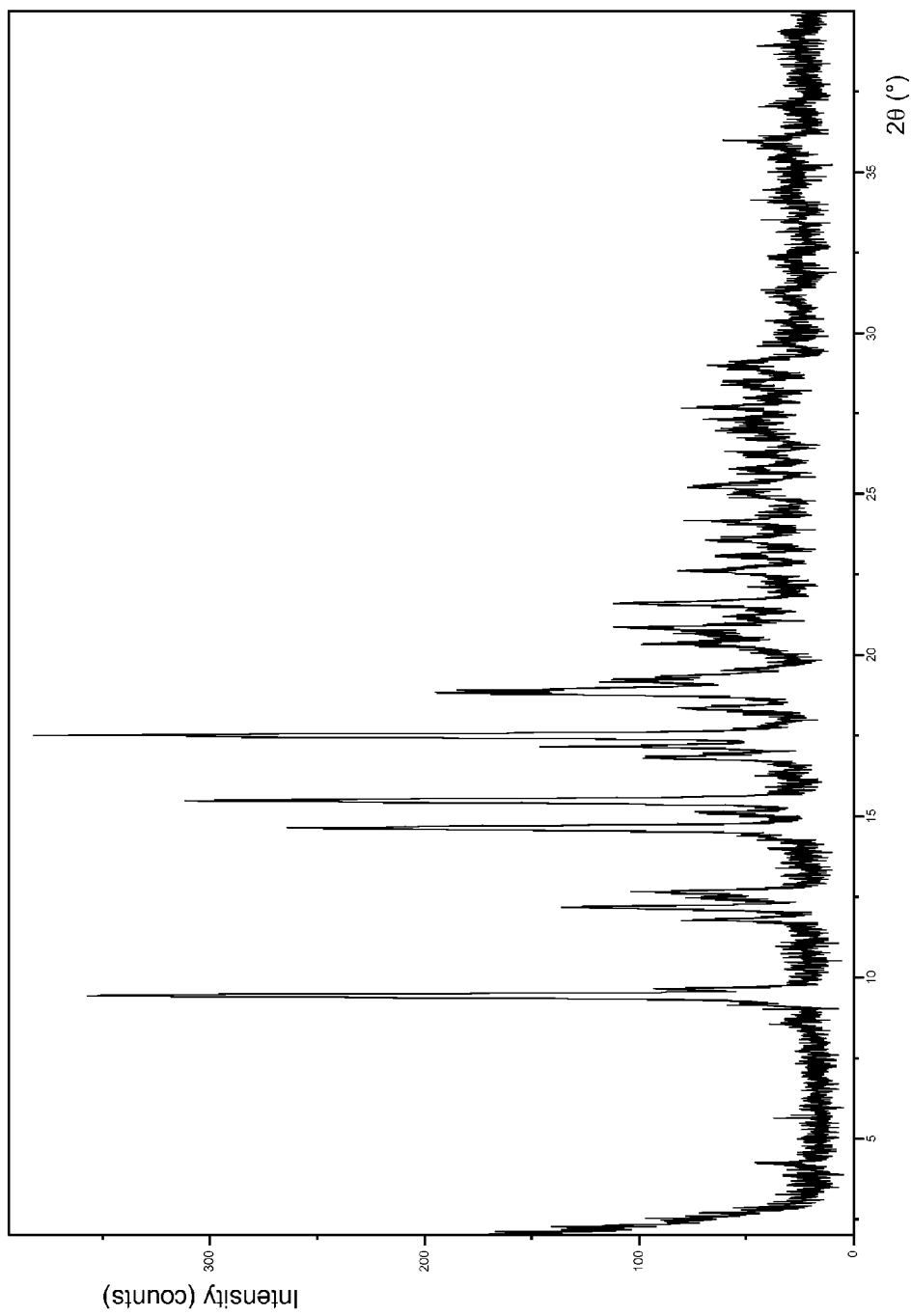
FIG. 20 is an X-ray powder diffraction pattern of Compound I Form VIII.

Compound I Form VIII is characterized by an X-ray powder diffractogram comprising peaks at 9.4, 15.5, and 17.5° 2θ±0.2° 2θ, as determined on a diffractometer using Cu-Kα radiation at a wavelength of 1.54178 Å. The diffractogram further comprises peaks at 14.6, 12.2, and 18.8° 2θ±0.2° 2θ. Compound I Form VIII also is characterized by an XRPD diffractogram substantially as shown in FIG. 20.

Figure 21:
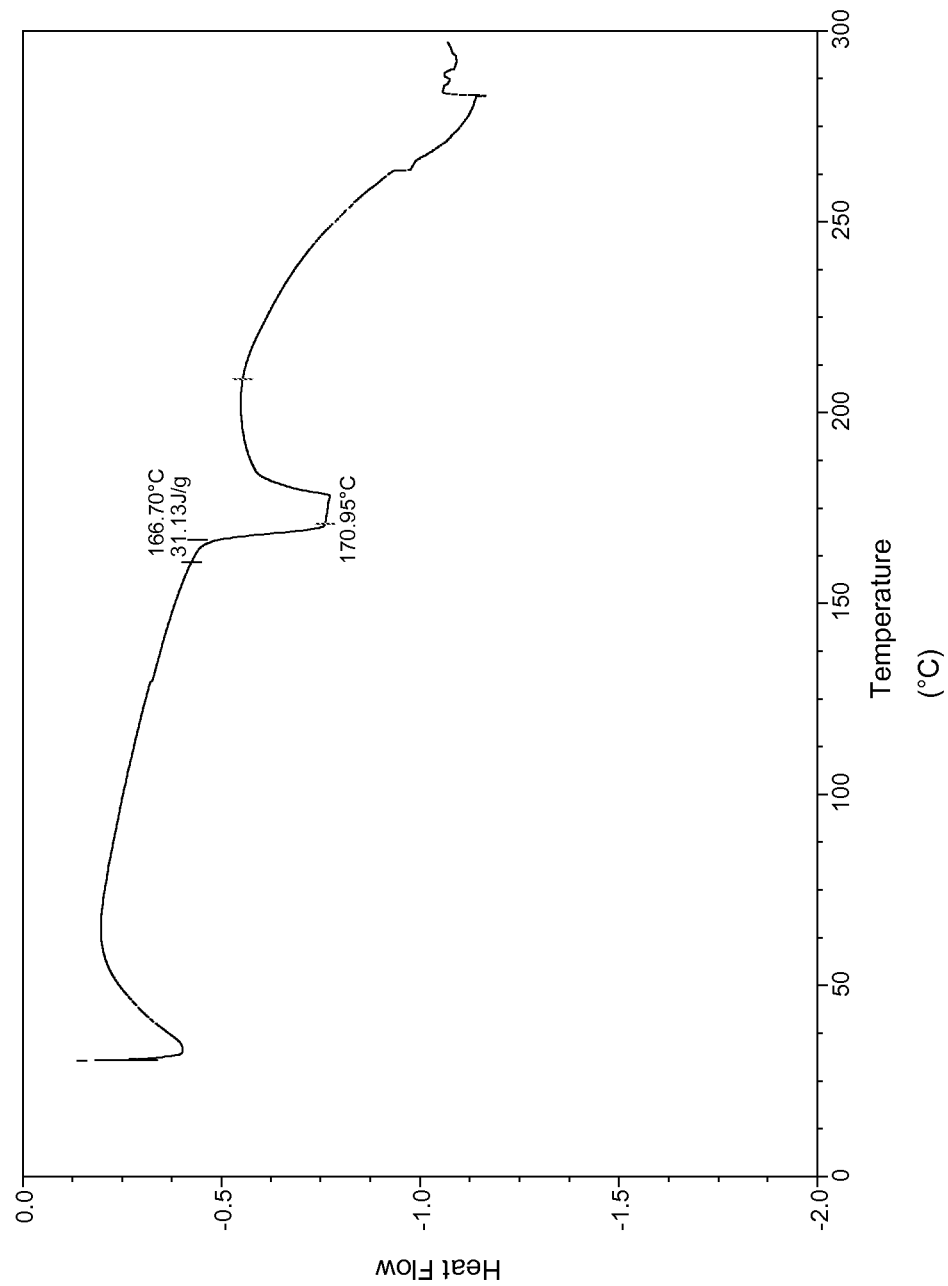
FIG. 21 is differential scanning calorimetry (DSC) curve of Compound I Form VIII.

Alternatively, Compound I Form VIII is characterized by a differential scanning calorimetry (DSC) curve that comprises an endotherm at about 171° C. Form VIII also is characterized by a DSC curve substantially as shown in FIG. 21.

Figure 22:
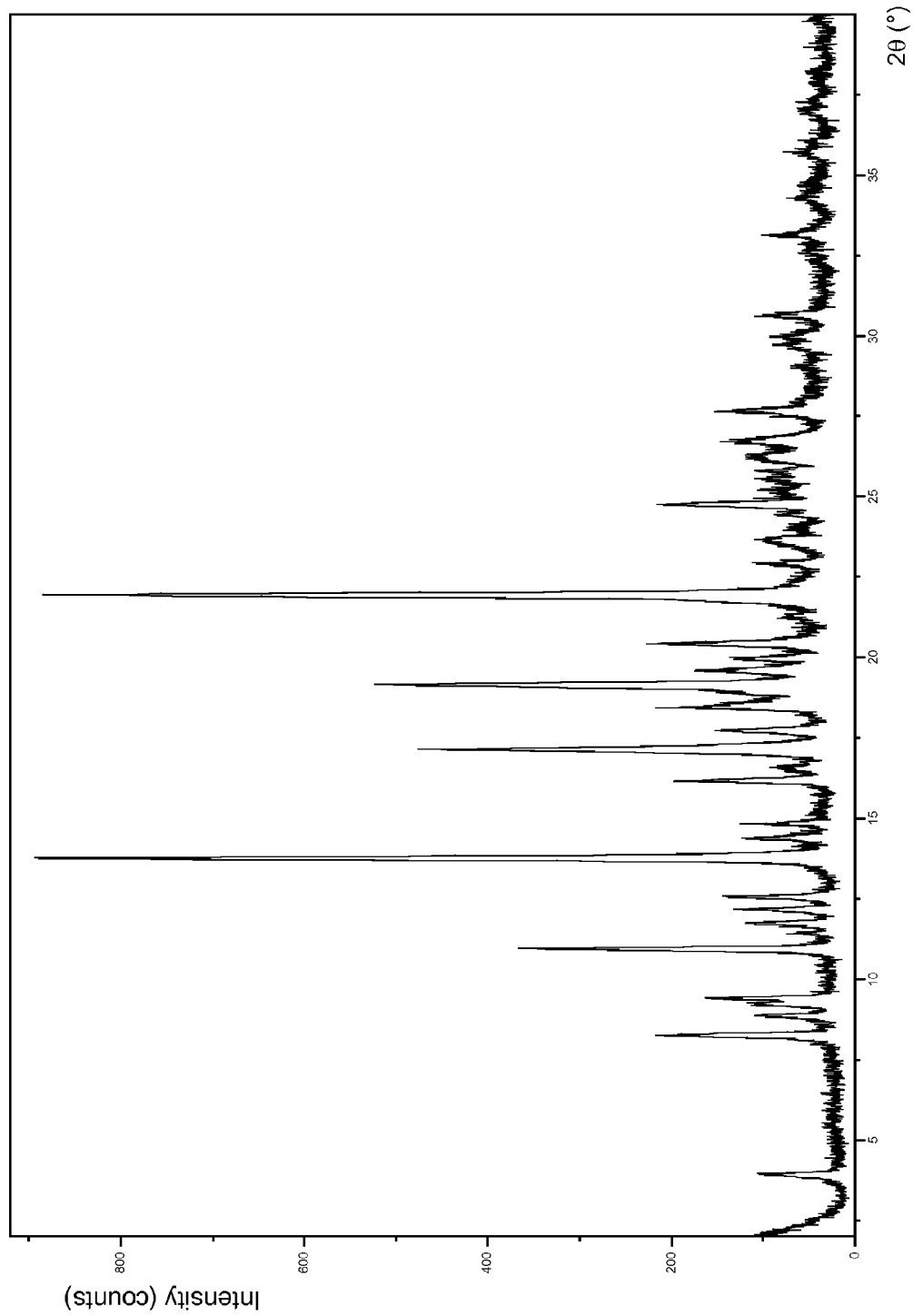
FIG. 22 is an X-ray powder diffraction pattern of Compound I Form IX.

Compound I Form IX is characterized by an X-ray powder diffractogram comprising peaks at 13.8, 19.2, and 22.0° 2θ±0.2° 2θ, as determined on a diffractometer using Cu-Kα radiation at a wavelength of 1.54178 Å. The diffractogram further comprises peaks at 8.2, 11.0, and 17.1° 2θ±0.2° 2θ. Compound I Form IX is further characterized by an XRPD diffractogram substantially as shown in FIG. 22.

Figure 23:
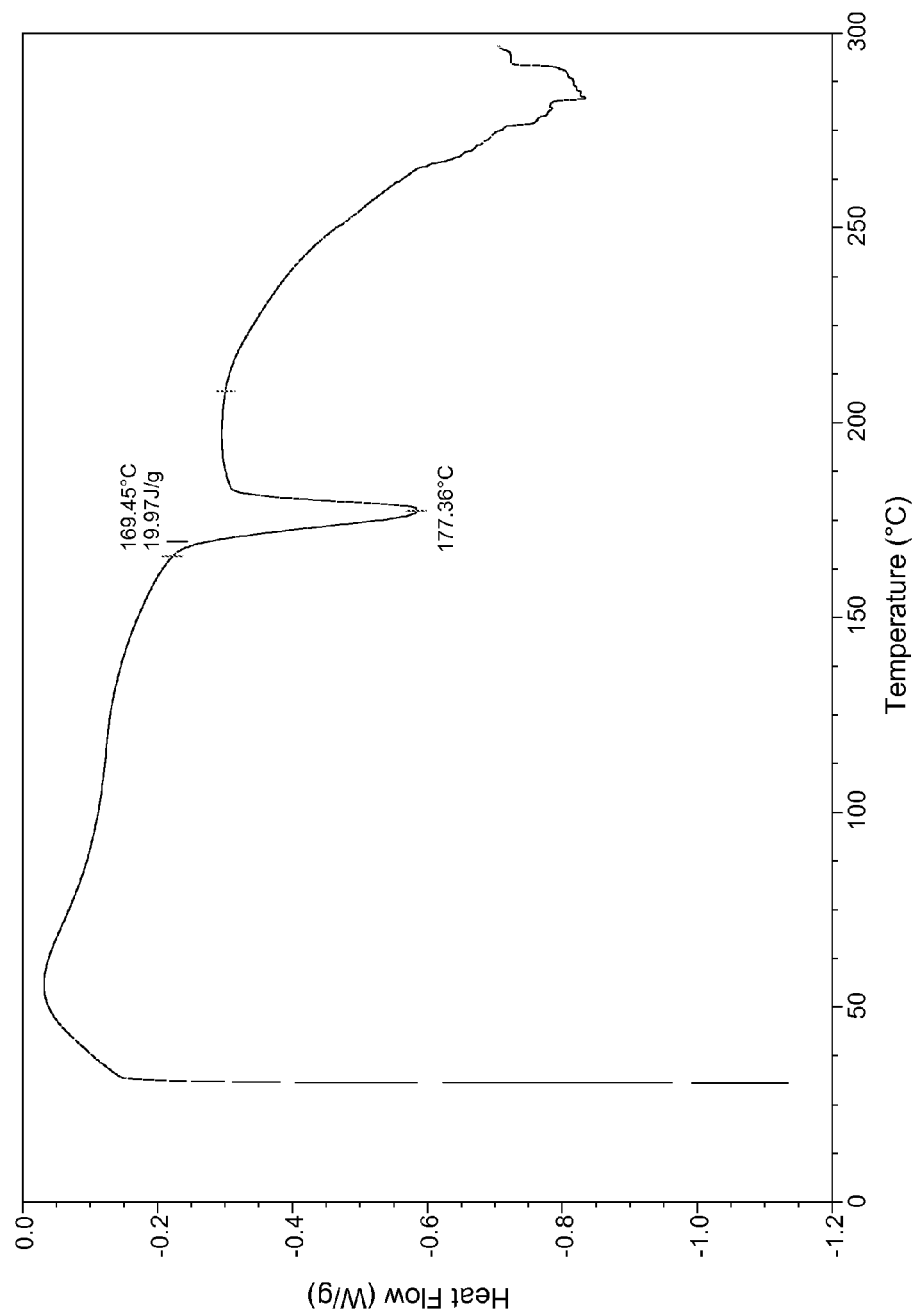
FIG. 23 is differential scanning calorimetry (DSC) curve of Compound I Form IX.

Alternatively, Compound I Form IX is characterized by a differential scanning calorimetry (DSC) curve that comprises an endotherm at about 177° C. Form IX also is characterized by a DSC curve substantially as shown in FIG. 23.

Figure 24:
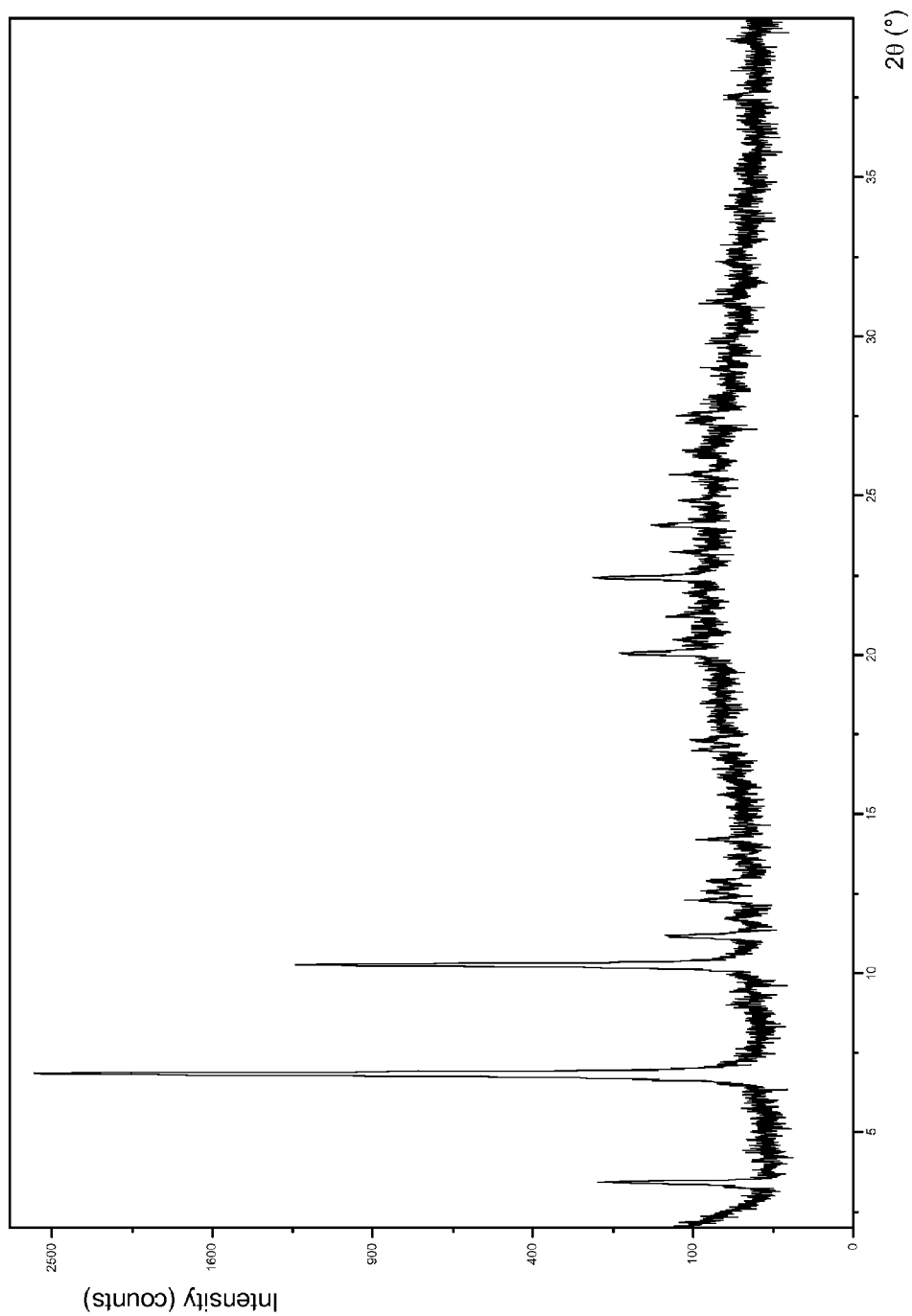
FIG. 24 is an X-ray powder diffraction pattern of Compound I Form X.

Compound I Form X is characterized by an X-ray powder diffractogram comprising peaks at 3.4, 6.9, and 10.3° 2θ±0.2° 2θ, as determined on a diffractometer using Cu-Kα radiation at a wavelength of 1.54178 Å. The diffractogram further comprises peaks at 11.2, 20.0, and 22.4° 2θ±0.2° 2θ. Compound I Form X is additionally characterized by an XRPD diffractogram substantially as shown in FIG. 24.

Figure 25:
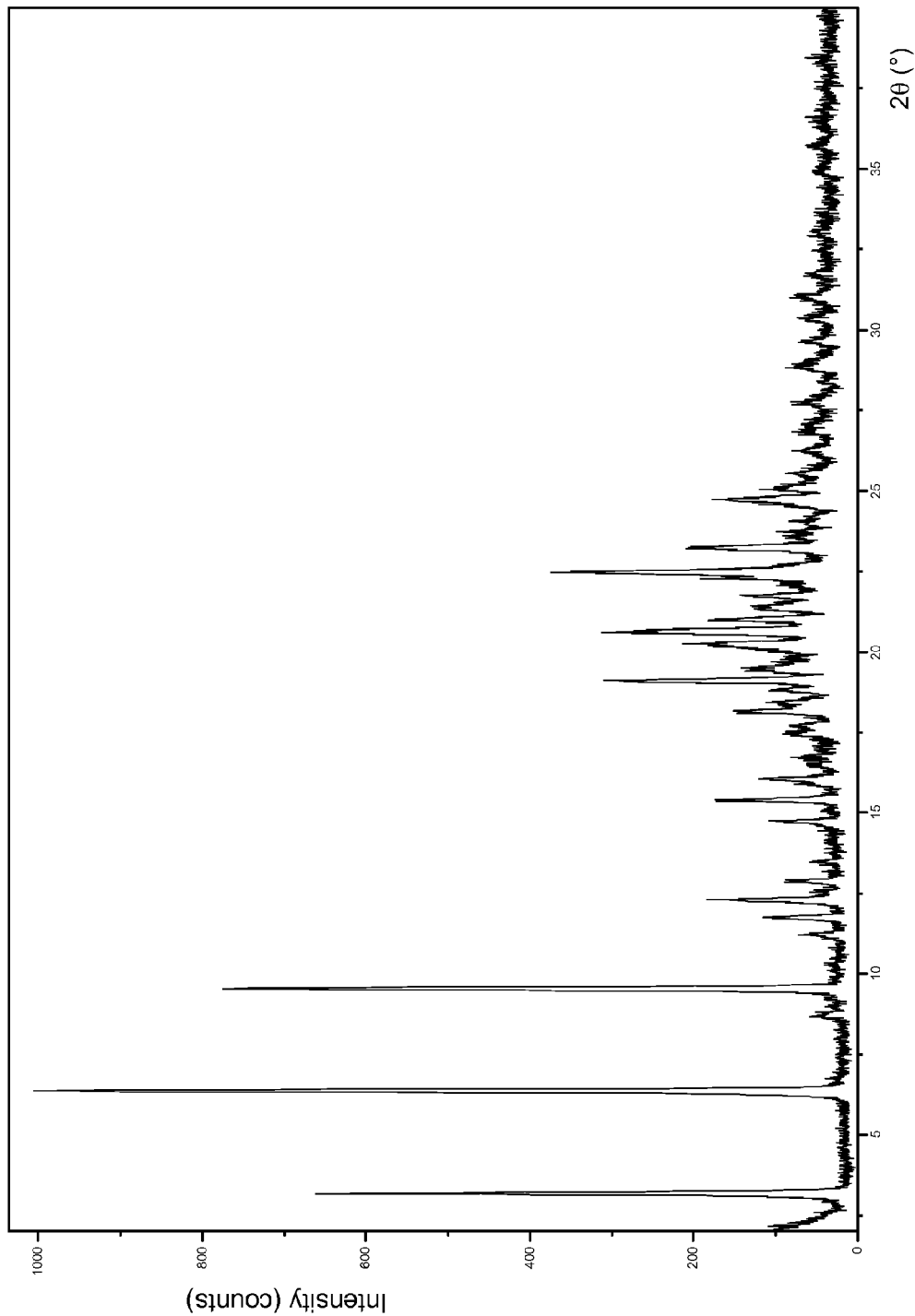
FIG. 25 is an X-ray powder diffraction pattern of Compound I Form XI.

Compound I Form XI is characterized by an X-ray powder diffractogram comprising peaks at 3.2, 6.3, and 9.5° 2θ±0.2° 2θ, as determined on a diffractometer using Cu-Kα radiation at a wavelength of 1.54178 Å. The diffractogram further comprises peaks at 19.1, 20.6, and 22.5°2θ±0.2° 2θ. Compound I Form XI also is characterized by an XRPD diffractogram substantially as shown in FIG. 25.

Figure 26:
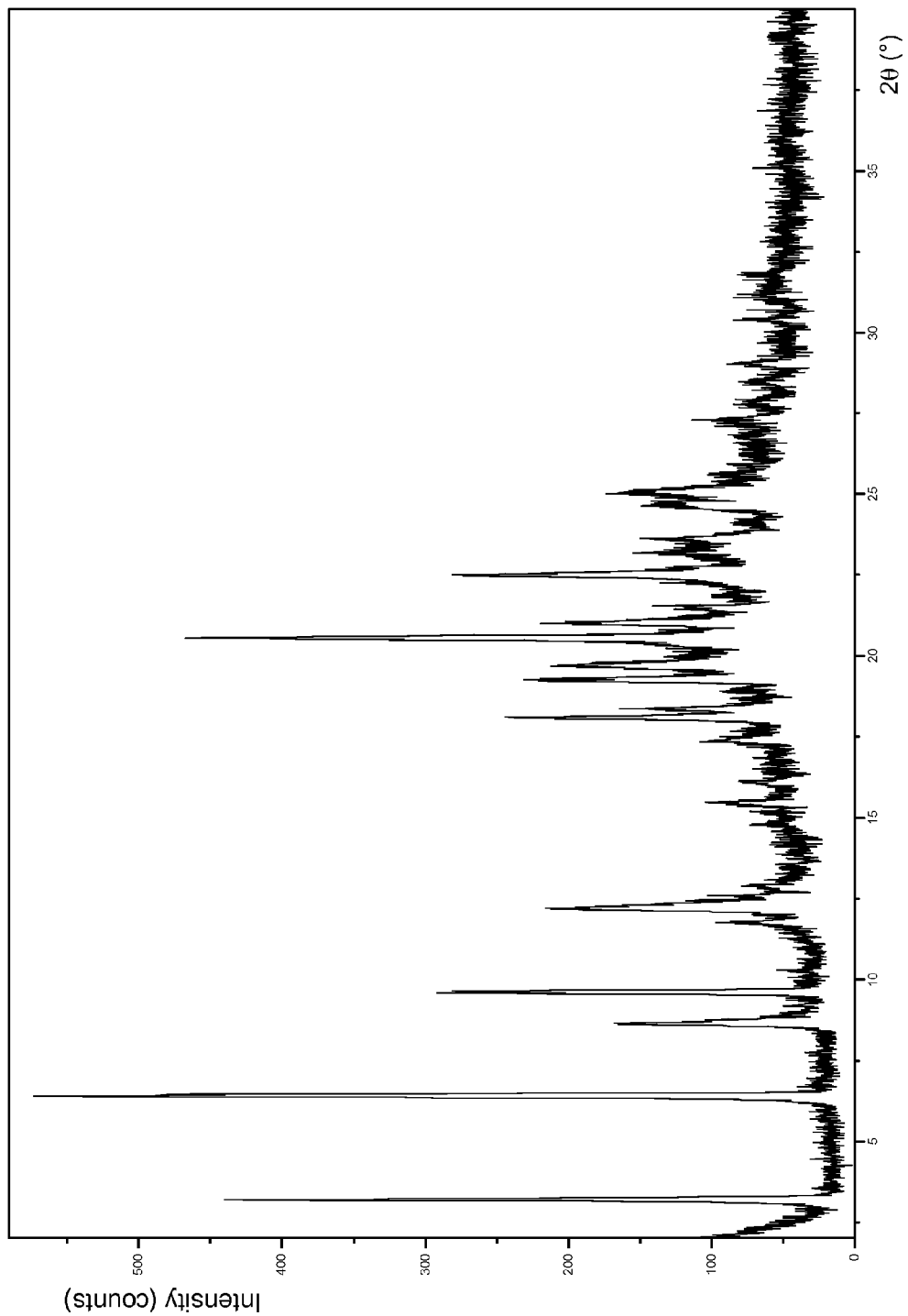
FIG. 26 is an X-ray powder diffraction pattern of Compound I Form XII.

Compound I Form XII is characterized by an X-ray powder diffractogram comprising peaks at 3.2, 6.4, and 20.6° 2θ±0.2° 2θ, as determined on a diffractometer using Cu-Kα radiation at a wavelength of 1.54178 Å. The diffractogram further comprises peaks at 9.6, 18.1, and 22.5° 2θ±0.2° 2θ. Compound I Form XII also is characterized by an XRPD diffractogram substantially as shown in FIG. 26.

Figure 27:
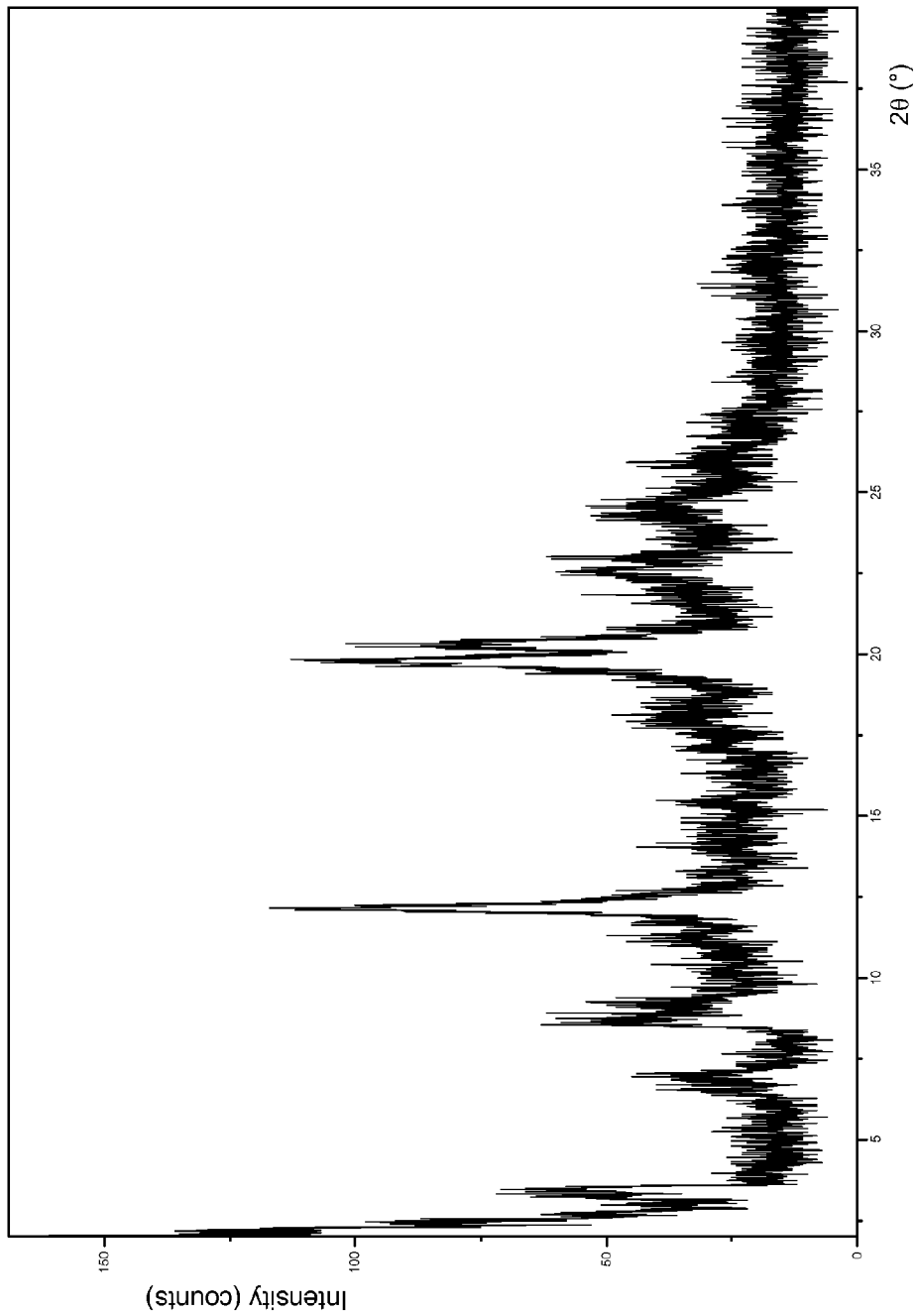
FIG. 27 is an X-ray powder diffraction pattern of Compound I Form XIII-THF.

Compound I Form XIII-THF is characterized by an X-ray powder diffractogram comprising peaks at 3.2, 3.5, and 7.0° 2θ±0.2° 2θ, as determined on a diffractometer using Cu-Kα radiation at a wavelength of 1.54178 Å. The diffractogram further comprises peaks at 8.6, 12.1, and 19.8° 2θ±0.2° 2θ. Compound I Form XIII-THF also is characterized by an XRPD diffractogram substantially as shown in FIG. 27.

Figure 28:
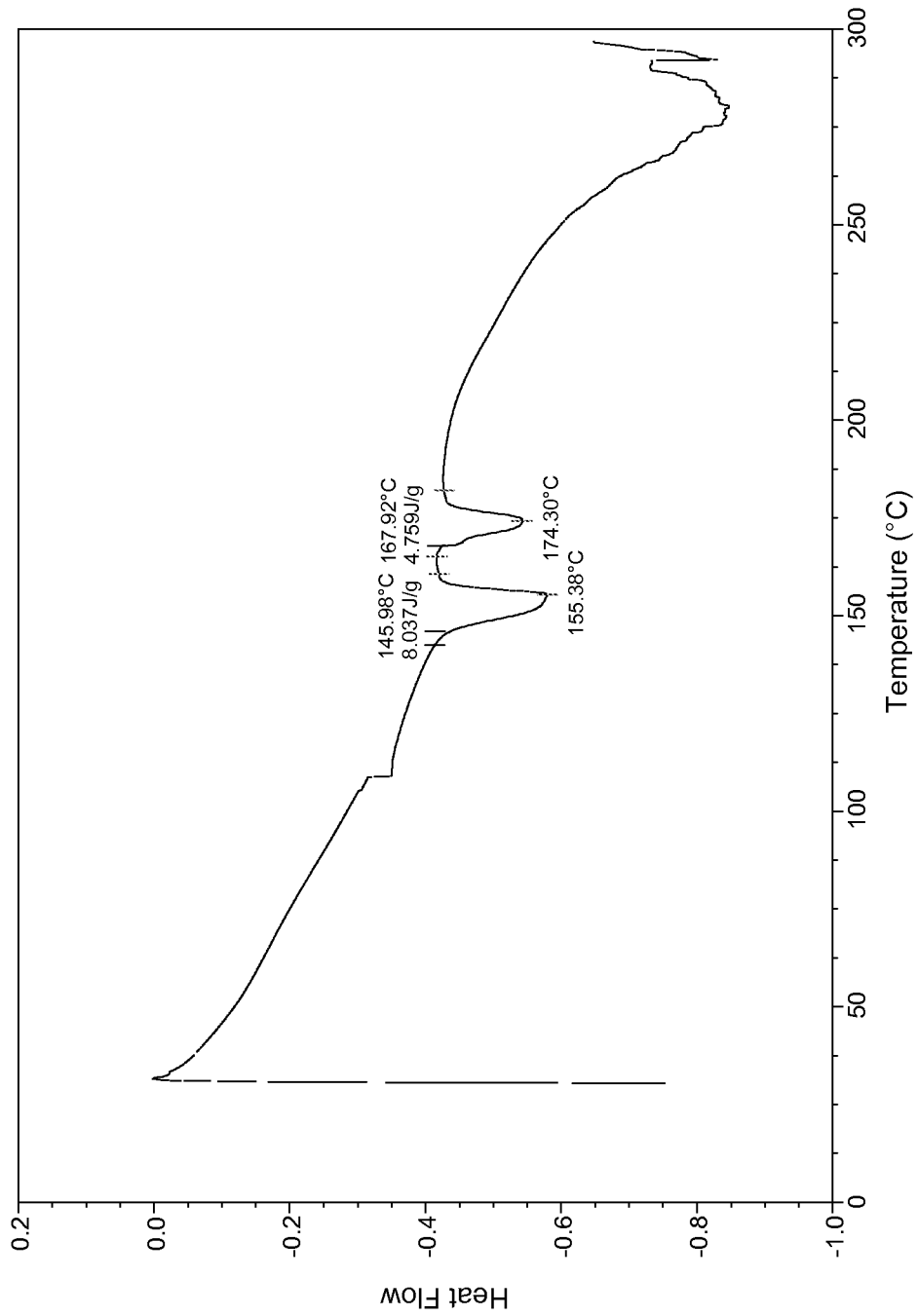
FIG. 28 is differential scanning calorimetry (DSC) curve of Compound I Form XIII-THF.

Alternatively, Compound I Form XIII-THF is characterized by a differential scanning calorimetry (DSC) curve that comprises endotherms at about 155° C. and 173° C. Form XIII-THF also is characterized by its DSC curve substantially as shown in FIG. 28.

Figure 29:
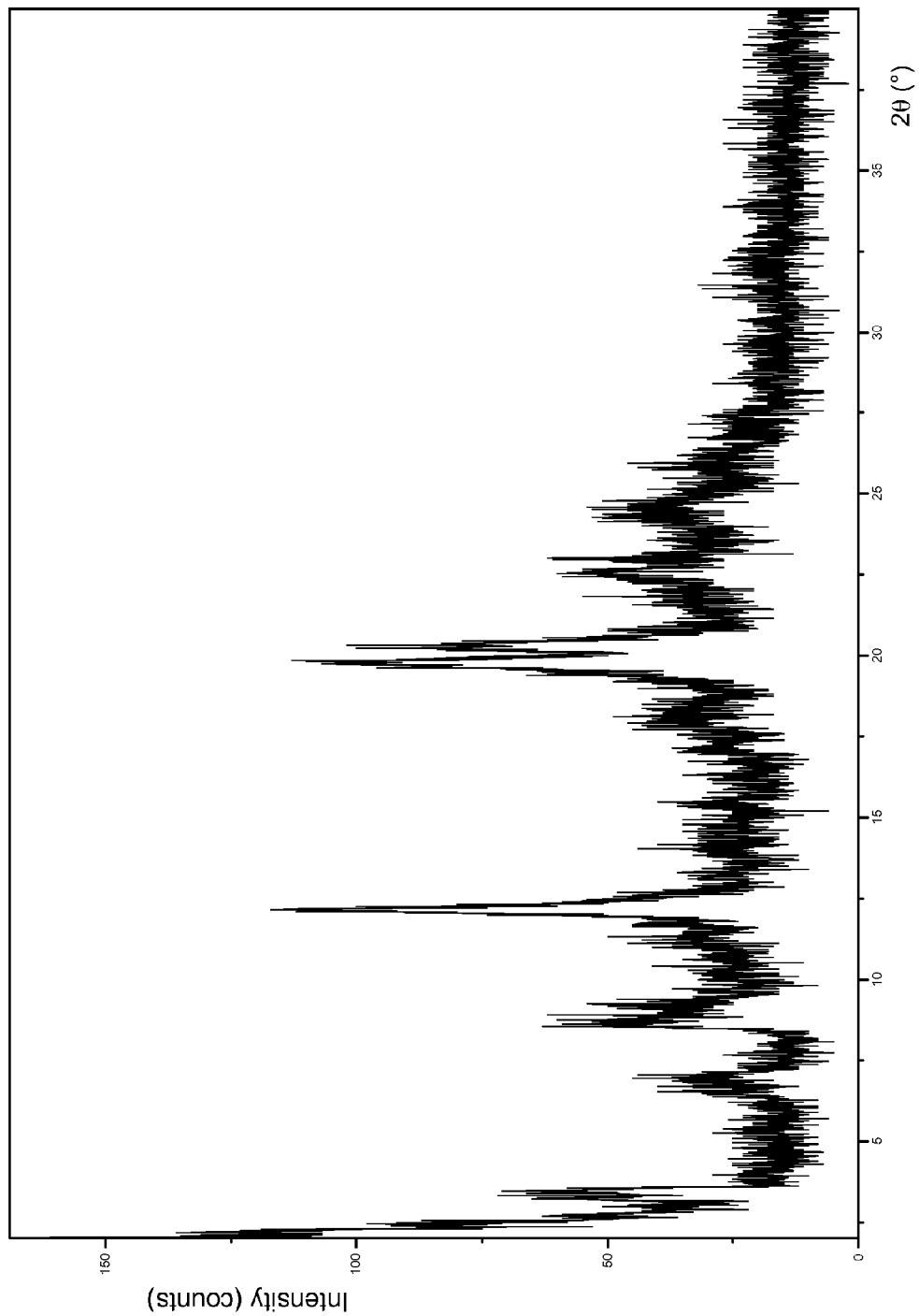
FIG. 29 is an X-ray powder diffraction pattern of Compound I Form XIII-MEK.

Compound I Form XIII-MEK is characterized by an X-ray powder diffractogram comprising peaks at 3.2, 3.5, and 7.0° 2θ±0.2° 2θ, as determined on a diffractometer using Cu-Kα radiation at a wavelength of 1.54178 Å. The diffractogram further comprises peaks at 8.6, 12.1, and 19.8° 2θ±0.2° 2θ. Compound I Form XIII-MEK is additionally characterized by an XRPD diffractogram substantially as shown in FIG. 29.

Figure 30:
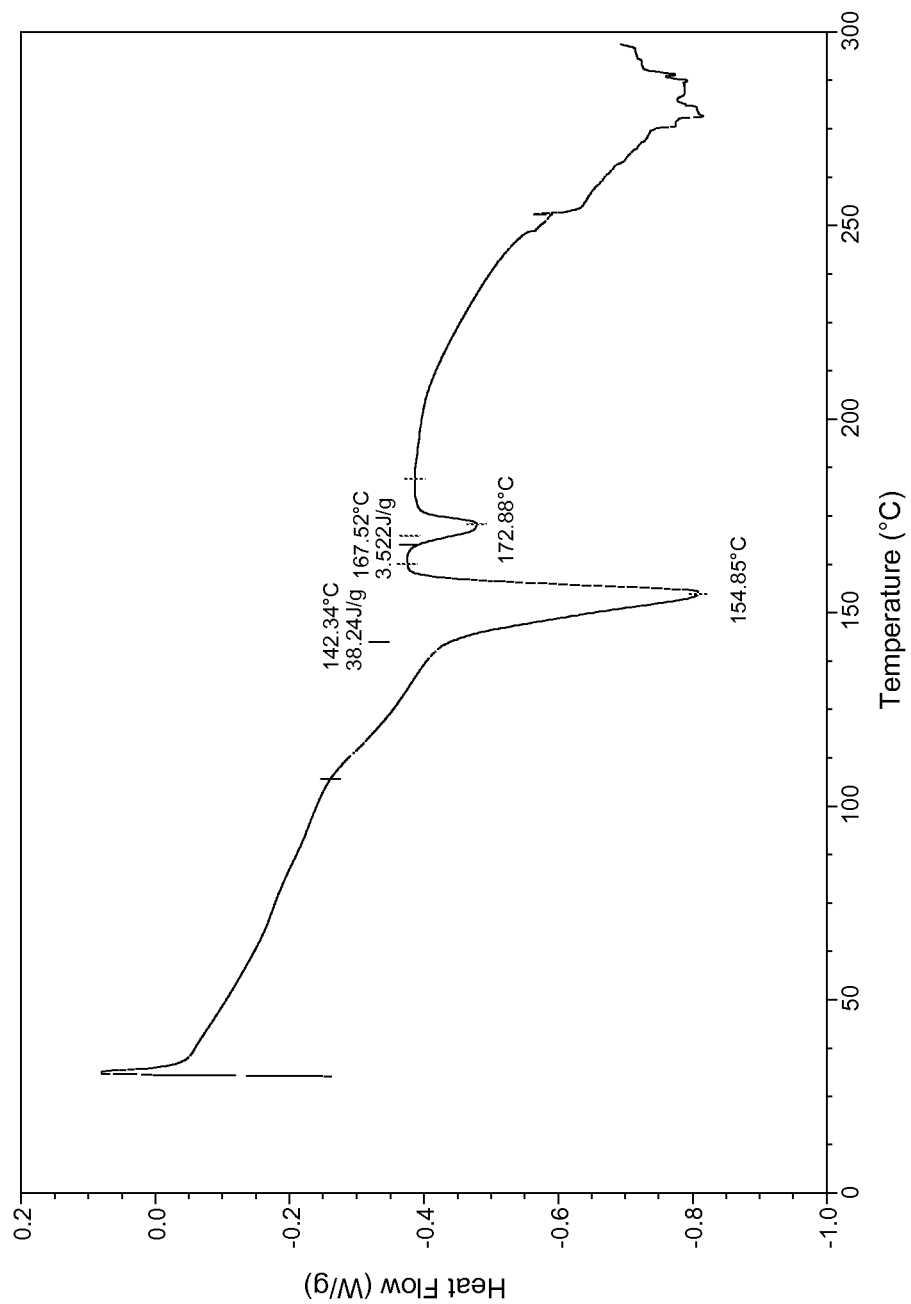
FIG. 30 is differential scanning calorimetry (DSC) curve of Compound I Form XIII-MEK.

Alternatively, Compound I Form XIII-MEK is characterized by a differential scanning calorimetry (DSC) curve that comprises endotherms at about 155° C. and 173° C. Form XIII-MEK also is characterized by its DSC curve substantially as shown in FIG. 30.

Figure 31:
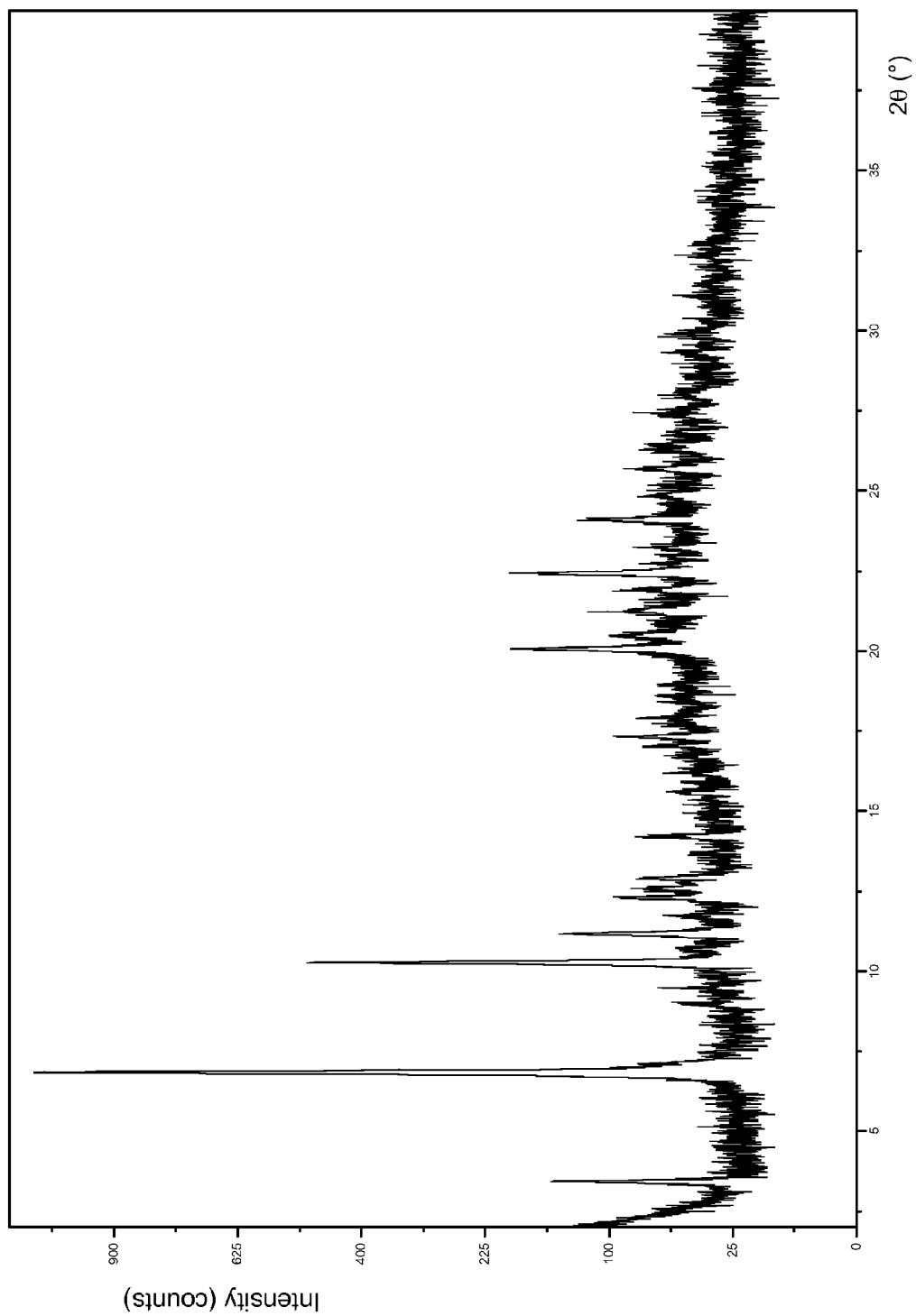
FIG. 31 is an X-ray powder diffraction pattern of Compound I Form XIV.

Compound I Form XIV is characterized by an X-ray powder diffractogram comprising peaks at 6.9, 10.3, and 22.4° 2θ±0.2° 2θ, as determined on a diffractometer using Cu-Kα radiation at a wavelength of 1.54178 Å. The diffractogram further comprises peaks at 3.4, 11.2, and 20.1° 2θ±0.2° 2θ. Compound I Form XIV also is characterized by an XRPD diffractogram substantially as shown in FIG. 31.

Figure 32:
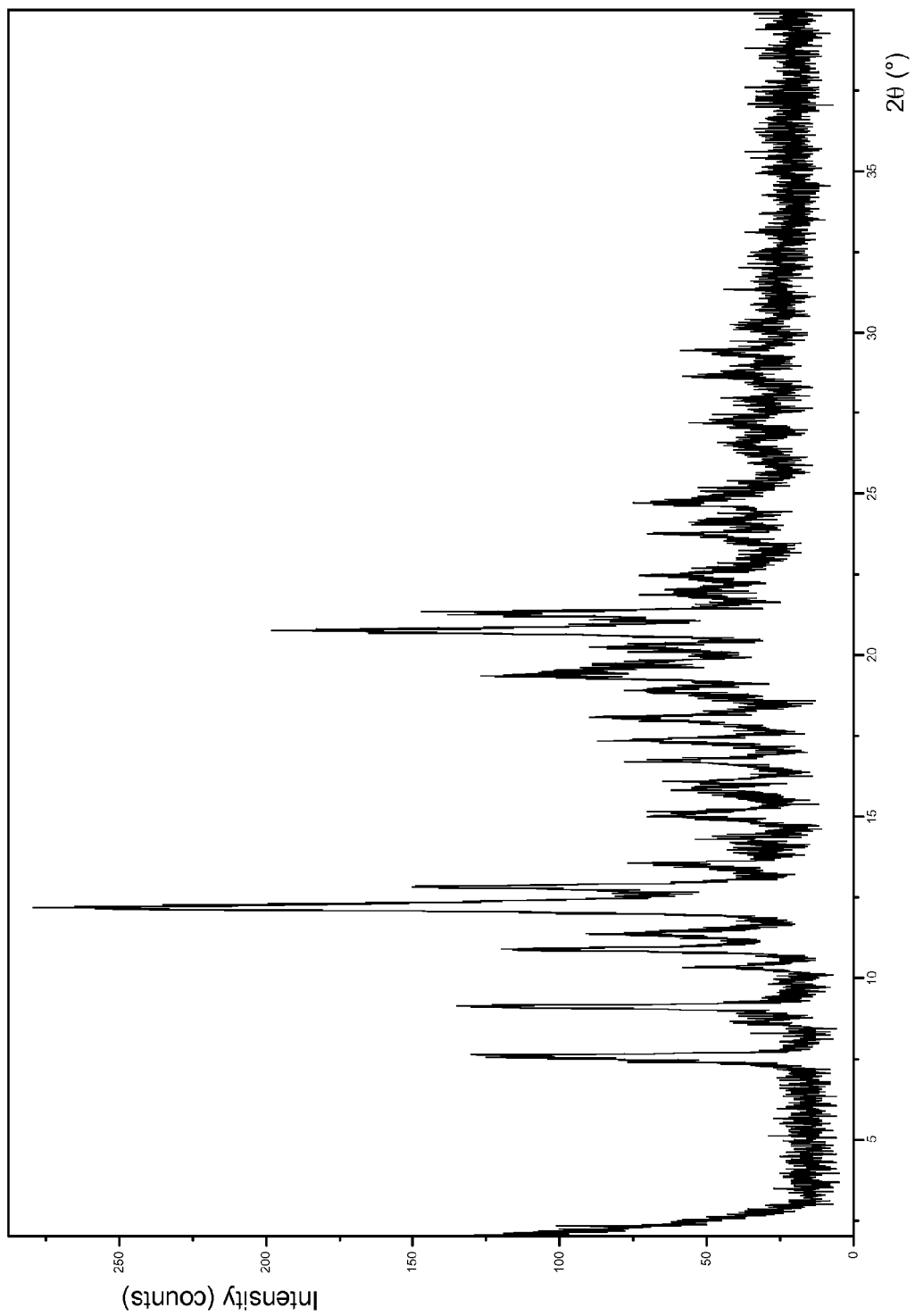
FIG. 32 is an X-ray powder diffraction pattern of Compound I Form XV.

Compound I Form XV is characterized by an X-ray powder diffractogram comprising peaks at 12.1, 12.8, and 20.8° 2θ±0.2° 2θ, as determined on a diffractometer using Cu-Kα radiation at a wavelength of 1.54178 Å. The diffractogram further comprises peaks at 9.1, 10.9, and 21.3° 2θ±0.2° 2θ. Form XV additionally is characterized by an XRPD diffractogram substantially as shown in FIG. 32.

Figure 33:
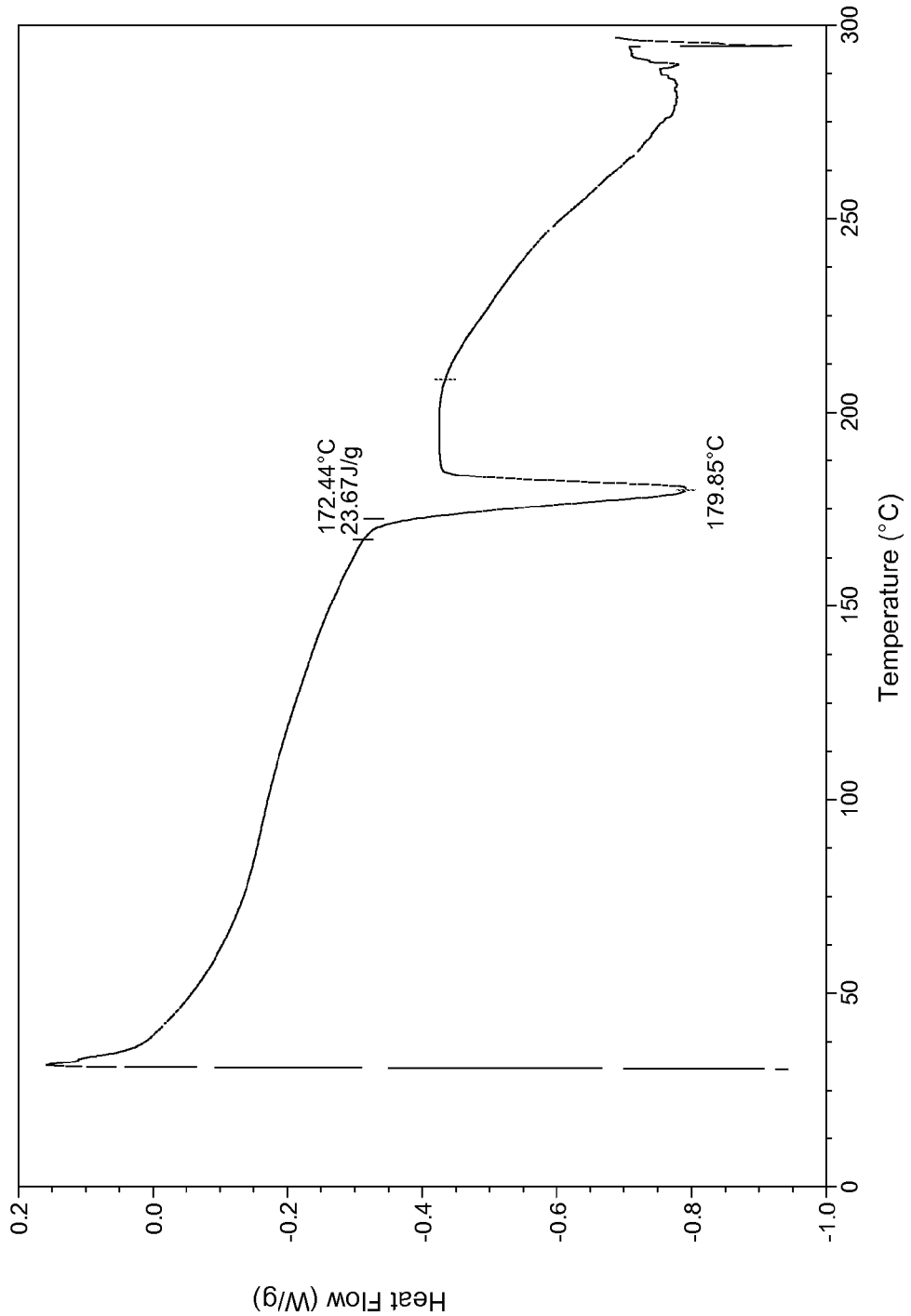
FIG. 33 is differential scanning calorimetry (DSC) curve of Compound I Form XV.

Alternatively, Compound I Form XV is characterized by a differential scanning calorimetry (DSC) curve that comprises an endotherm at about 180° C. Compound I Form XV is further characterized by its DSC curve substantially as shown in FIG. 33.

The amorphous Compound I is characterized by a glass transition temperature (Tg) of about 160° C. The amorphous Compound I has no defined melting point and the decomposition occurs at temperatures above 200° C. It is hygroscopic as determined by dynamic vapor sorption, showing a maximum weight gain of 5.4% at 90% relative humidity. It does not undergo moisture induced phase transformation at any humidity level.

Figure 34:
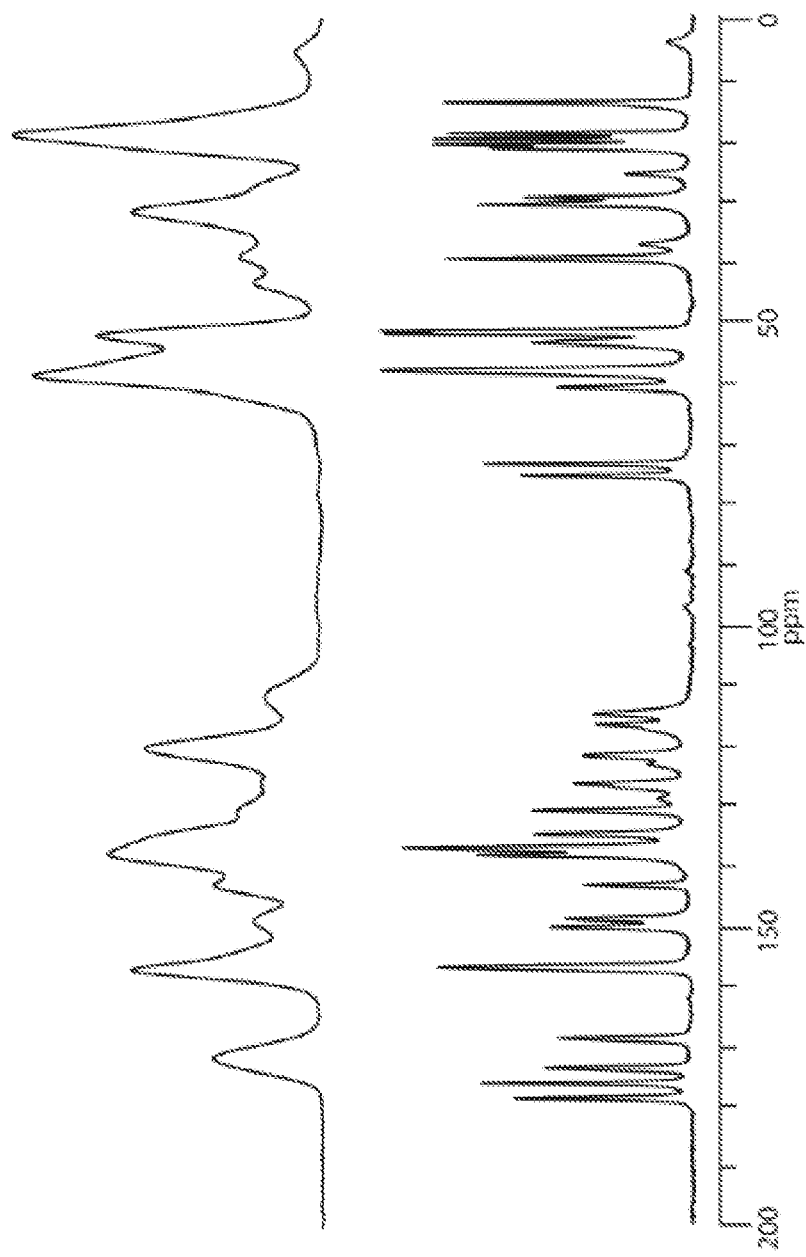
FIG. 34 is a comparison between the $^{13}$C-solid state NMR (ssNMR) spectra of amorphous Compound I (top curve) and Compound I D-tartrate (bottom curve), respectively.

Alternatively, the amorphous Compound I is characterized by $^{13}$C-solid state NMR (ssNMR) spectra as substantially shown by top curve in FIG. 34.

Figure 35:
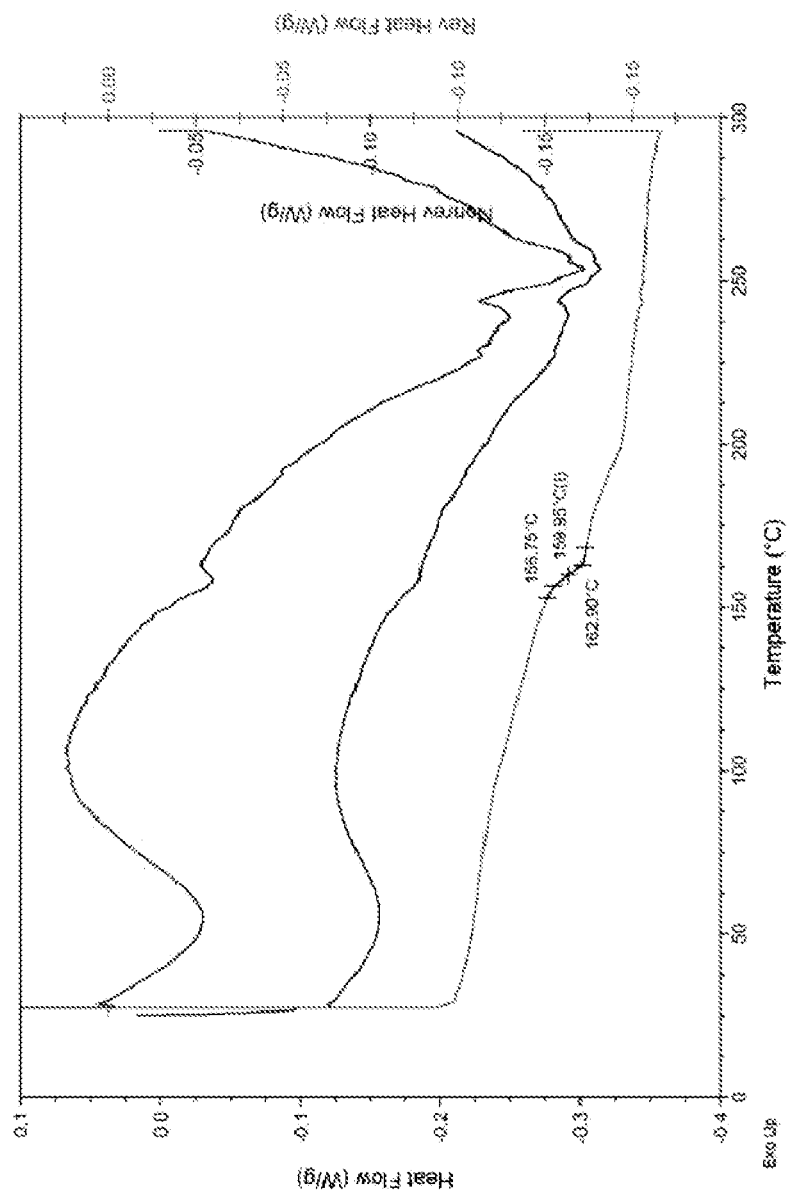
FIG. 35 is modulated differential scanning calorimetry (mDSC) curve of amorphous Compound I.

Alternatively, amorphous Compound I is characterized by a differential scanning calorimetry (DSC) curve that comprises a glass transition temperature of about 160° C. Amorphous Compound I also is characterized by its full DSC curve substantially as shown in FIG. 35.

Figure 36:
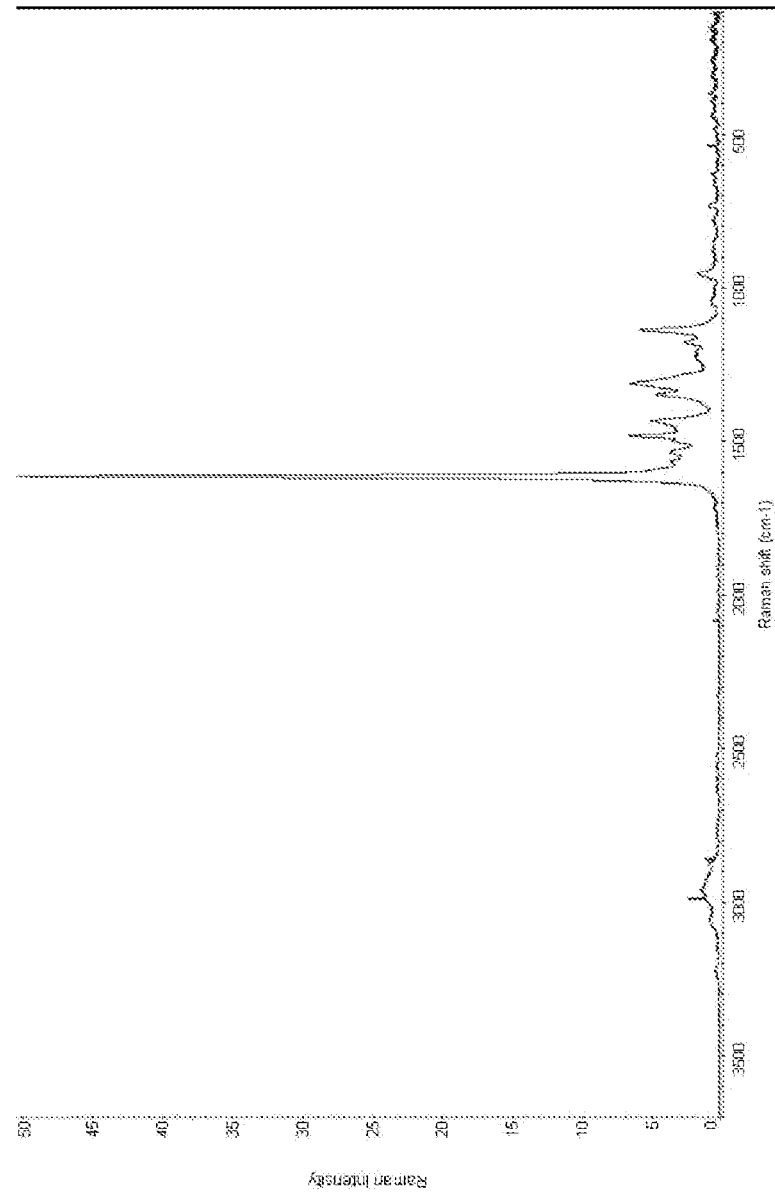
FIG. 36 is Fourier-transformed Raman (FT-Raman) spectra of amorphous Compound I.

Alternatively, amorphous Compound I is characterized by Fourier-transformed Raman (FT-Raman) spectra that comprises peaks at 939 and 1552 cm$^{-1}$. Amorphous Compound I also is characterized by its full FT-Raman spectra substantially as shown in FIG. 36.

Pharmaceutical Formulations

The Compound I forms of this disclosure are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as, for example, those set forth in the Handbook of Pharmaceutical Excipients (1986). Excipients include ascorbic acid and other antioxidants, chelating agents such as, for example, EDTA, carbohydrates such as, for example, dextrin, hydroxyalkylcellulose, hydroxyalkylmethylcellulose, stearic acid and the like. The pH of the formulations ranges from about 3 to about 11, but is ordinarily about 7 to 10. Typically, the Compound I form will be administered in a dose from 0.01 milligrams to 2 grams. In one embodiment, the dose will be from about 10 milligrams to 450 milligrams. It is contemplated that the Compound I form may be administered once, twice or three times a day.

While it is possible for the active ingredients to be administered alone it may be preferable to present them as pharmaceutical formulations. The formulations, both for veterinary and for human use, of the disclosure comprise at least one active ingredient, as above defined, together with one or more acceptable carriers therefore and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present disclosure suitable for oral administration may be presented as discrete units such as, for example, capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as, for example, a powder or granules, optionally mixed with a binder, lubricant, inert diluent, or preservative. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as, for example, 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as, for example, propylene glycol, butane 1,3-diol, mannitol, sorbitol, glycerol and polyethylene glycol (including PEG 400) and mixtures thereof. The topical formulations may desirably include a Compound I form which enhances absorption or penetration of the active ingredient through the skin or other affected areas. Examples of such dermal penetration enhancers include dimethyl sulphoxide and related analogs.

The oily phase of the emulsions of this disclosure may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the disclosure include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as, for example, di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as, for example, white soft paraffin and/or liquid paraffin or other mineral oils are used.

Pharmaceutical formulations according to the present disclosure comprise one or more Compound I forms of the disclosure together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as, for example, calcium or sodium carbonate, lactose, lactose monohydrate, croscarmellose sodium, povidone, calcium or sodium phosphate; granulating and disintegrating agents, such as, for example, maize starch, or alginic acid; binding agents, such as, for example, cellulose, microcrystalline cellulose, starch, gelatin or acacia; and lubricating agents, such as, for example, magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as, for example, glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as, for example, peanut oil, liquid paraffin or olive oil.

Aqueous suspensions of the disclosure contain the active materials in admixture with excipients suitable for the manufacture of aqueous suspensions. Such excipients include a suspending agent, such as, for example, sodium carboxymethylcellulose, methylcellulose, hydroxypropyl methylcellulose, sodium alginate, polyvinylpyrrolidone, gum tragacanth and gum acacia, and dispersing or wetting agents such as, for example, a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as, for example, ethyl or n-propyl p-hydroxy-benzoate, one or more coloring agents, one or more flavoring agents and one or more sweetening agents, such as, for example, sucrose or saccharin.

Oil suspensions may be formulated by suspending the active ingredient in a vegetable oil, such as, for example, arachis oil, olive oil, sesame oil or coconut oil, or in a mineral oil such as, for example, liquid paraffin. The oral suspensions may contain a thickening agent, such as, for example, beeswax, hard paraffin or cetyl alcohol. Sweetening agents, such as, for example, those set forth above, and flavoring agents may be added to provide a palatable oral preparation. These compositions may be preserved by the addition of an antioxidant such as, for example, ascorbic acid.

Granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as, for example, olive oil or arachis oil, a mineral oil, such as, for example, liquid paraffin, or a mixture of these. Suitable emulsifying agents include naturally-occurring gums, such as, for example, gum acacia and gum tragacanth, naturally occurring phosphatides, such as, for example, soybean lecithin, esters or partial esters derived from fatty acids and hexitol anhydrides, such as, for example, sorbitan monooleate, and condensation products of these partial esters with ethylene oxide, such as, for example, polyoxyethylene sorbitan monooleate. The emulsion may also contain sweetening and flavoring agents. Syrups and elixirs may be formulated with sweetening agents, such as, for example, glycerol, sorbitol or sucrose. Such formulations may also contain a demulcent, a preservative, a flavoring or a coloring agent.

The pharmaceutical compositions of the disclosure may be in the form of a sterile injectable preparation, such as, for example, a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as, for example, a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as, for example, oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as, for example, gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as, for example, 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as, for example, compounds heretofore used in the treatment or prophylaxis of conditions associated with HCV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this disclosure may include other agents conventional in the art having regard to the type of formulation in question, for example those suitable for oral administration may include flavoring agents.

The disclosure further provides veterinary compositions comprising at least one active ingredient as above defined together with a veterinary carrier therefore.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compound I forms of the disclosure can also be formulated to provide controlled release of the active ingredient to allow less frequent dosing or to improve the pharmacokinetic or toxicity profile of the active ingredient. Accordingly, the disclosure also provides compositions comprising one or more Compound I forms of the disclosure formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

In one embodiment, the present disclosure provides a pharmaceutical composition comprising a compound selected from the group consisting of Compound I Form I, Compound I Form II, Compound I Form III, Compound I D-tartrate, Compound I Form IV, Compound I Form V, Compound I Form VI, Compound I Form VII, Compound I Form VIII, Compound I Form IX, Compound I Form X, Compound I Form XI, Compound I Form XII, Compound I Form XIII-THF, Compound I Form XIII-MEK, Compound I Form XIV, and Compound I Form XV and a pharmaceutically acceptable excipient.

In another embodiment, the present disclosure provides a pharmaceutical composition comprising amorphous 1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester, characterized by a glass transition temperature (Tg) of about 160° C. and a pharmaceutically acceptable excipient.

Representative examples of pharmaceutical formulations of Compound I forms are discussed in Examples 11 and 12.

Methods of Use

The solid forms of Compound I described herein are administered to a subject suffering from hepatitis C virus (HCV) in either single or multiple doses by any of the accepted modes of administration known to those who are skilled in the art. Administration routes include, for example, those described in any patents and patent applications incorporated by reference, such as rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

Oral administration can be carried out by delivering any of the Compound I forms by capsule or enteric coated tablets, or the like.

The Compound I forms also can be administered by transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992, 445 and 5,001,139. Such patches may be constructed for continuous, pulsatile, or on demand delivery of pharmaceutical agents.

The compounds are preferably formulated in a unit dosage form. The term "unit dosage forms" refers to physically discrete units suitable as unitary dosages for human subjects and other mammals, each unit containing a predetermined quantity of active material calculated to produce the desired therapeutic effect. The compounds are generally administered in a pharmaceutically effective amount.

For oral administration, each dosage unit typically contains from 1 mg to 2 g of a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

Combination Therapy

Subjects being treated by administration of Compound I forms described in the present disclosure can benefit from treatment with additional therapeutic agents that are effective in treating HCV, or enhance the anti-HCV therapeutic effect of Compound forms, in accordance with some embodiments. Additional therapeutic agents that are useful for this purpose include, but are not limited to, ribavirin,

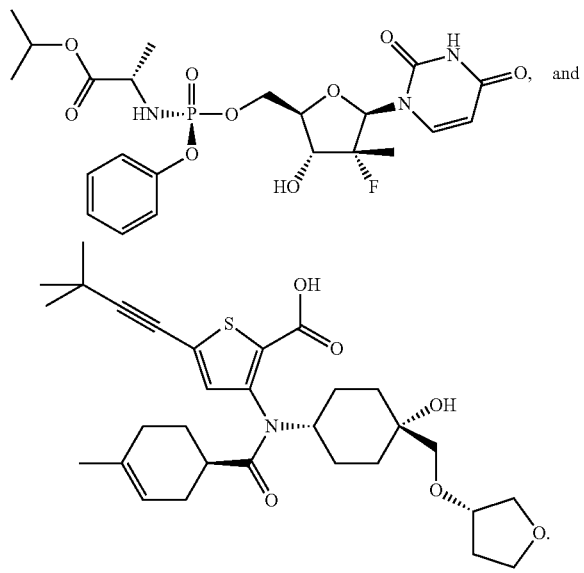

The present disclosure is not to be limited in scope by the specific embodiments disclosed in the examples, which are intended to be illustrations of a few embodiments of the disclosure, nor is the disclosure to be limited by any embodiments that are functionally equivalent within the scope of this disclosure. Indeed, various modifications of the disclosure in addition to those shown and described herein will become apparent to those skilled in the art and are intended to fall within the scope of the appended claims. To this end, it should be noted that one or more hydrogen atoms or methyl groups can be omitted from the drawn structures consistent with accepted shorthand notation of such organic compounds, and that one skilled in the art of organic chemistry would readily appreciate their presence.

EXAMPLES

Example 1

Preparation of (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester diacetone solvate (Compound I Form I)

Approximately 15-60 mg of amorphous (1-{3-[6-(9,9-difluoro-7-{2-[5-(2-methoxycarbonylamino-3-methyl-butyryl)-5-aza-spiro[2.4]kept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester (HPLC purity of 99.3%) were weighed and transferred to a vial equipped with a mini magnetic stir bar. Acetone was added in increments of 200 μL that resulted in the formation of a slurry. The slurry was allowed to stir for two weeks at room temperature (~22° C.) and examined periodically.

After two weeks, a sample of 300 μL, of the slurry was removed from the vial, transferred to a centrifuge filter (Costar, 0.45 micron) and centrifuged at 1000 rpm for 2 minutes. The solid in the wet cake form were analyzed using XRPD analysis (PANalytical X'Pert PRO X-ray powder diffractometer). This diffractometer uses Cu-Kα radiation at a wavelength of 1.54178 Å, and it operates under reflection mode. Scan range is from 2 to 40 degree 2 theta. The step size is 0.008° at a scan speed of 0.13°/s, which gives about 5 min per scan. After air drying the small sample, XRPD analysis was performed again to monitor any change in the diffraction pattern between the wet and dry material. Thermogravimetric analysis (TGA) was run on the saturated solution to determine the solubility of the equilibrating solids in the solvent when the solid appeared to be crystalline.

Figure 2:
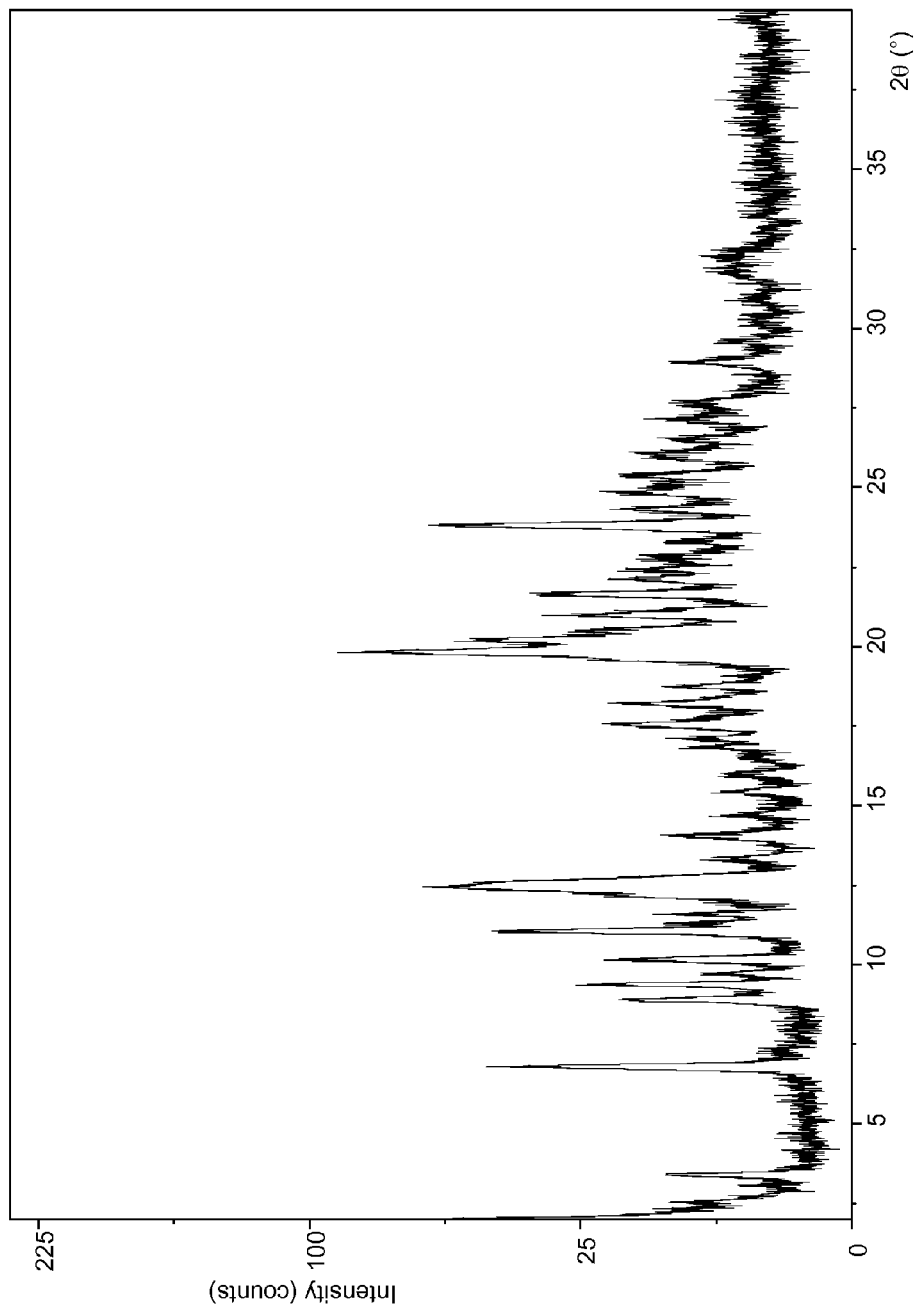
FIG. 2 is an X-ray powder diffraction pattern of Compound I Form I.

The results of these analyses revealed that Compound I transformed from an amorphous solid to a crystalline material after being stirred in acetone for ~11 days. As shown in FIG. 1, the solid material that is in equilibrium with acetone solution, when filtered and dried gently over less than 1 hour, has a distinct XRPD pattern as compared to the broad halo for the amorphous starting material. The XRPD pattern for Compound I Form I is shown in FIG. 2 and major peaks and their related intensities in the XRPD pattern are shown in Table 1 below.

TABLE 1

Major Peaks in the XRPD Pattern for Compound I Form I

| Peak Position (°2θ) | Relative Intensity (%) |
|---|---|
| 3.4 | 53.3 |
| 6.8 | 100.0 |
| 8.8 | 34.4 |
| 9.3 | 37.7 |
| 10.2 | 34.8 |
| 11.0 | 49.7 |
| 12.5 | 76.8 |
| 19.8 | 72.7 |
| 21.6 | 14.4 |
| 23.8 | 41.6 |

Crystallinity of Form I was further confirmed by a Polarized Light Microscopic (PLM) image of the crystals.

HPLC analysis showed that the transformation of Compound I from amorphous to Form I improved the % AN purity from 99.3% to 99.8%. Further investigation showed that the acetone solvate offers significant impurity purging capability in that the reaction mixture with 96-97.5% AN before crystallization was upgraded to ~99.6% AN when Form I was isolated. Accordingly, Form I crystallization was utilized on scale to purify crude Compound I before the final Compound I is produced.

The differential scanning calorimetry (DSC) curve of Form I showed that upon heating this crystalline material has a minor endotherm at 124.20° C., which indicates a desolvation of acetone from the solvate crystal (FIG. 3). Following the desolvation endotherm, there was a major endotherm at 162.43° C., which indicates the melting of the desolvated solid. The thermogravimetric analysis (TGA) curve of Form I showed a 12.20% weight loss over a wide temperature range of 50-130° C., which indicated that Form I likely has some loosely bound acetone mixed with strongly bound acetone. The amount of weight loss also indicated that Form I is a diacetone solvate because the theoretical acetone content for a monoacetone solvate is 6.1%.

Example 2

Preparation of (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester monoacetone solvate (Compound I Form II)

Compound I Form II was prepared by partially desolvating Form I, as described more fully below. Methods of desolvation are well-known to those who are skilled in the art. These include, for instance, application of a vacuum, prolonged exposure to ambient conditions, subjecting Form I to elevated temperature, and subjecting Form I to a flow of gas, such as air or nitrogen, and any combination thereof. In some embodiments, the preparation of Compound I Form I as described above in Example 1 results in the formation of detectable amounts of Compound I Form II. Hence, in these embodiments, it is possible to prepare mixtures of Form I and Form II.

As one example, Compound I Form I crystals were dried under a vacuum at ~21° C. during 5 days, after which Compound I Form II formed. The XRPD pattern for Form II is distinct from that for Form I, as shown in FIG. 4. Major peaks and their related intensities in the XRPD pattern are shown in Table 2 below.

TABLE 2

Major Peaks in the XRPD Pattern for Compound I Form II

| Peak Position (°2θ) | Relative Intensity (%) |
| --- | --- |
| 7.5 | 36.9 |
| 9.3 | 34.8 |
| 11.4 | 55.6 |
| 12.2 | 94.6 |
| 12.7 | 59.0 |
| 13.4 | 35.4 |
| 14.1 | 22.5 |
| 14.9 | 17.2 |
| 17.8 | 29.3 |
| 18.6 | 17.5 |
| 20.0 | 58.7 |
| 20.5 | 100.0 |
| 22.7 | 31.0 |
| 26.2 | 26.5 |

The DSC curve of Form II showed one broad endotherm at 130.27° C., which indicated a desolvation of acetone from the solvated crystal along with melting at the same temperature range (FIG. 5). The TGA curve of Form II showed a 7.7% weight loss over a wide temperature range of 70-150° C., which indicated that Form II has some loosely bound acetone mixed with strongly bound acetone. The amount of weight loss also indicated that Form II is a monoacetone solvate because the theoretical acetone content for a monosolvate of acetone is 6.1%. Both TGA and DSC data show that Form II has a reasonably stable structure toward thermal stress.

Figure 6:
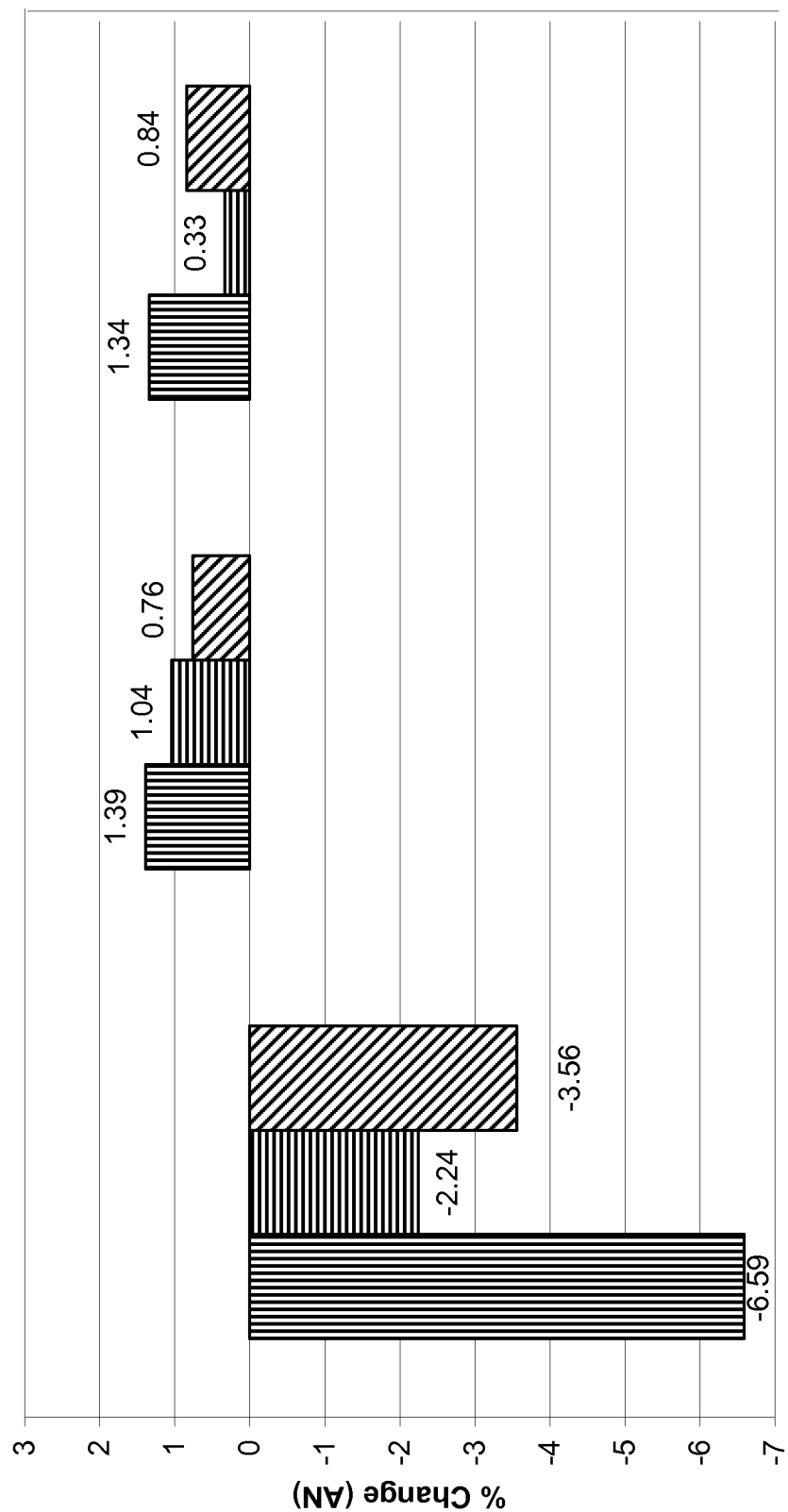
FIG. 6 compares the photodegradation behaviors of amorphous Compound I (vertical stripes), Compound I Form II (horizontal stripes), and a partially amorphous hydrochloride salt of Compound I (diagonal stripes) during photoexposure at 0.9 M Lux-hrs. The leftmost group of bars represents the overall decrease in HPLC % AN of these three forms of Compound I. The middle group of bars represents the formation of a primary photodegradation impurity resulting from each form of Compound I. The rightmost group of bars similarly represents the formation of a secondary photodegradation impurity that eluted on HPLC at relative retention time (RRT) 1.67.

Form II surprisingly exhibits enhanced photostability compared to amorphous Compound I and a partially amorphous HCl salt of Compound I. Thus, separate samples of Form II, amorphous Compound I, and partially amorphous Compound I HCl salt were photoexposed in the amount of 0.9 M Lux-hrs. HPLC analyses of the samples compared the amounts of photodegradation products in each sample. As shown in FIG. 6, the leftmost group of bars depicts the overall decrease in HPLC % AN for Compound I in the three different solid forms mentioned above. For example, Form II of Compound I gave rise to the lowest (2.24% AN) amount of photodegradation in this experiment.

The middle group and rightmost group of bars depict the amounts of two of the major photodegradation impurities formed after the three solid forms of Compound I were photoexposed. These comparisons demonstrate that, overall, Form II exhibited the best photostability among the three forms compared.

Example 3

Preparation of (1-{3-[6-(9,9-difluoro-7-{5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl)-2-aza-bicyclo[2.2.1]heptane-2-carbonyl}-2-methyl-propyl)-carbamic acid methyl ester (Compound I Form III)

Despite the surprising advantages that Form II offers over amorphous Compound I, it still has a significant amount of tightly bound acetone in its structure. The purpose of this example is to break the solvate and generate an anhydrous crystalline form.

Thus, Form II crystals were heated to dry completely or to desolvate at ~115° C., that resulted in the discovery of a third crystalline form, Form III.

The formation of Form III was revealed by a variable temperature XRPD experiment. In this experiment, a sample of Form II was heated at 10° C./min starting from 25° C. After each 10° C. temperature rise, the sample was held at the raised temperature for 20 min to allow a XRPD pattern to be generated at that temperature. This heating and holding period was continued until the temperature reached 205° C. Some XRPD patterns at selected temperatures compared with the reference XRPD patterns for Form I, Form II, and Form III. This comparison showed that Form II starts to exhibit solid-solid transformation, upon heating, at temperatures above 85° C., and achieved significant conversion at 115° C., while conversion to Form III was completed at 145° C. The XPRD pattern of Form III is shown in FIG. 7. Major peaks and their related intensities in the XRPD pattern are shown in Table 3 below.

TABLE 3

Major Peaks in the XRPD Pattern for Compound I Form III

| Peak Position (°2θ) | Relative Intensity (%) |
| --- | --- |
| 8.3 | 53.2 |
| 12.4 | 100.0 |
| 14.2 | 69.3 |
| 15.0 | 47.8 |
| 20.4 | 43.0 |
| 21.6 | 84.7 |
| 23.3 | 26.5 |

Figure 8:
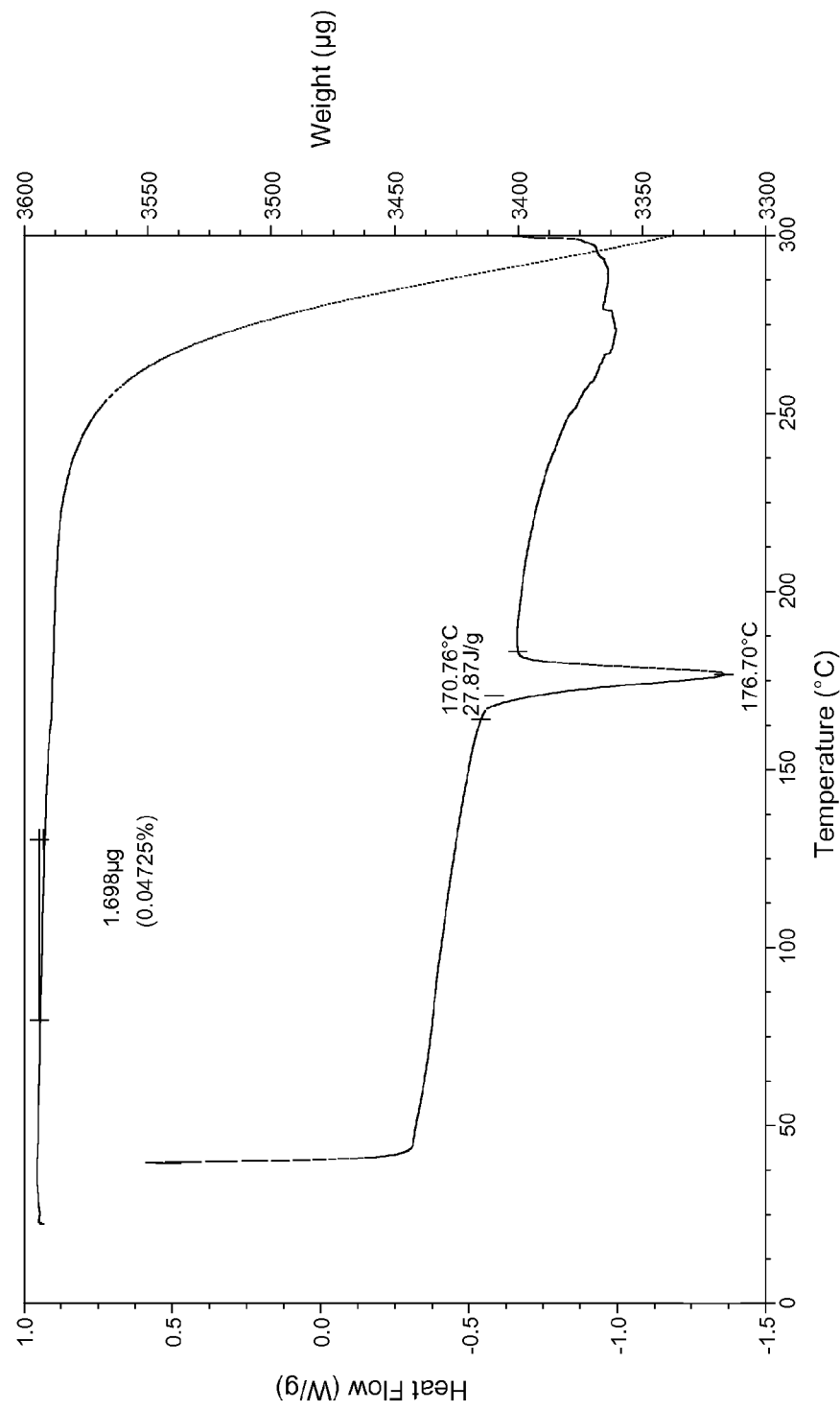
FIG. 8 is a combined differential scanning calorimetry plot (DSC; bottom curve) and thermogravimetric analysis (TGA; top curve) of Compound I Form III.

Form III began to melt at 175° C., which was confirmed by the DSC curve of form III (FIG. 8). The TGA curve of Form III, also shown in FIG. 8, indicates that this crystal form is anhydrous. Dynamic vapor sorption (DVS) data shows that Form III is nonhygroscopic, taking up less than 0.3% moisture at 90% relative humidity, as compared to 5.6% moisture uptake for amorphous Compound I.

Example 4

Preparation of (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester D-tartrate (Compound I D-tartrate)

Approximately 100-500 mg of Compound I Form I was transferred to each of a set of vials containing a magnetic stir bar. To each vial was added approximately 1.0-20 mL of acetonitrile (ACN) or isopropyl alcohol (IPA) until a clear solution was achieved. In a separate set of vials, clear ACN or IPA solutions of the acids listed in Table 4 below were prepared.

Each of the acid solutions was added to a corresponding solution of Compound I in a dropwise fashion until 1 equivalent of acid had been. If resulting suspensions were observed, they were allowed to cool from ambient temperature to ~0° C. If clear solutions were observed, they were allowed to slowly evaporate to assess possible crystallization.

Among the acids screened, L-tartaric acid and HCl separately appeared to react with Compound I Form I and gave weak signs of crystallinity, as determined by PLM. However, the solid products from these two reactions proved to be unstable and lost crystallinity easily upon exposure to ambient atmosphere.

TABLE 4

Salt Screen for Compound I

| Acid | pK$_a$ | Observations |
| --- | --- | --- |
| HCl | −6 | Disordered salt formed |
| Citric acid | triacid, 3.1; 4.8; 6.4 | No product formed |
| Maleic acid | diacid; 1.92; 6.23 | Amorphous product |
| L-tartaric acid | diacid; 3.02; 4.36 | Amorphous product formed |
| D-tartaric acid | diacid; 2.93; 4.23 | Crystalline product formed |
| fumaric acid | diacid, 3.03; 4.38 | No product formed |
| Toluene sulfonic acid monohydrate | −1.34 | No product formed |
| Benzene sulfonic acid | 0.7 | No product formed |
| Sulfuric acid | −3 | No product formed |
| Succinic acid | diacid, 4.2; 5.6 | No product formed |
| L-Malic acid | diacid, 3.46; 5.1 | No product formed |
| D-Malic acid | diacid, 3.46; 5.1 | No product formed |
| Malonic acid | diacid, 2.83; 5.69 | No product formed |
| Oxalic acid | diacid, 1.27; 4.28 | amorphous product |

Even with a thorough crystalline form screen for L-tartrate, no stable crystalline product was successfully produced, as summarized below in Table 5. XRPD characterization of various samples resulting from the stable form screen for L-tartrate showed that the samples remained as amorphous solids in most solvents. In acetone, Compound I reverted back to the acetone solvate Form I as described above.

TABLE 5

Crystalline Form Screen Summary for Compound I L-tartrate

| Solvent | 24 hr XRPD | 2 week XRPD | Observation |
| --- | --- | --- | --- |
| Water | Amorphous solid | Amorphous solid | Suspension |
| IPAc | Amorphous solid | Amorphous solid | Suspension |
| MTBE | Amorphous solid | Amorphous solid | Suspension |
| 2-propanol | Amorphous solid | Amorphous solid | Suspension |
| THF | N/A | N/A | Clear solution |
| Acetone | Compound I Form I | Compound I Form I | Suspension |
| Methanol | N/A | N/A | Clear solution |
| ACN | Amorphous solid | Amorphous solid | Suspension |
| Ethanol | N/A | N/A | Clear solution |
| Ethyl acetate | Amorphous solid | Amorphous solid | Suspension |
| 2-MeTHF | Amorphous solid | Amorphous solid | Suspension |
| MEK | Amorphous solid | Amorphous solid | Suspension |
| MIBK | Amorphous solid | Amorphous solid | Suspension |
| n-heptane | Amorphous solid | Amorphous solid | Suspension |
| Toluene | Amorphous solid | Amorphous solid | Suspension |
| DCM | Amorphous solid | Amorphous solid | Suspension |
| a$_w$ of 0.8 (EtOH/water) | N/A | N/A | Clear solution |

Following these observations, D-tartaric acid was added to the acid list. Thus, when an IPA solution of D-tartaric acid was added to a solution of Compound I in IPA, a white suspension was generated immediately. A sample was filtered and characterized with XRPD, according to parameters described above, that clearly showed a crystalline product, (1-{3-[6-,(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bi-cyclo [2.2.1]heptane-2-carbonyl}-2-methyl-propyl)-carbamic acid methyl ester D-tartrate (Compound I D-tartrate).

Figure 9:
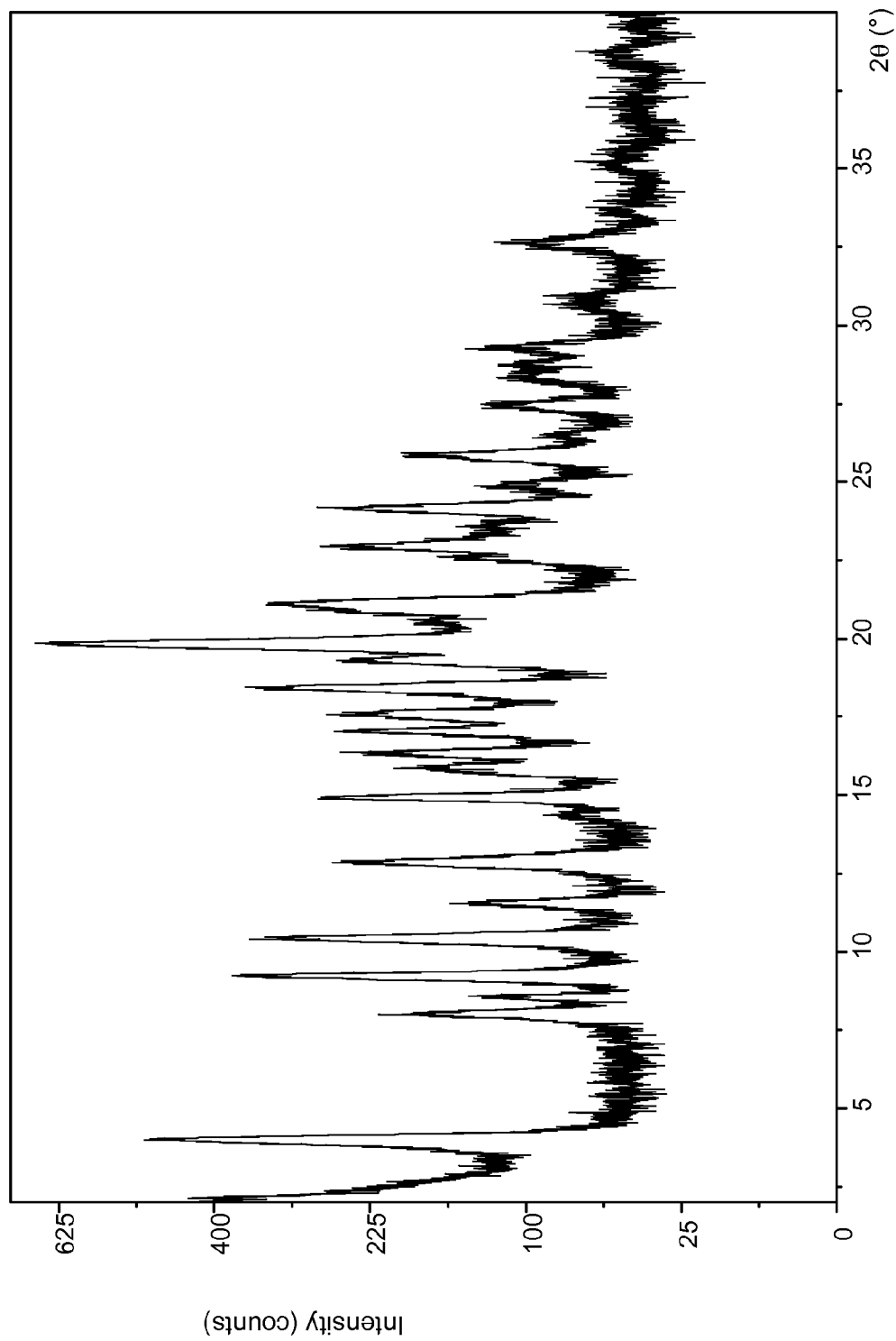
FIG. 9 is an X-ray powder diffraction pattern of Compound I D-tartrate.

FIG. 9 shows the XRPD pattern of Compound I D-tartrate. The major peaks and corresponding relative intensities in the XRPD pattern diagram are listed below in Table 6

TABLE 6

Major XRPD peaks for Compound I D-tartrate

| Position (°2θ) | Relative Intensity |
| --- | --- |
| 4.0 | 87.8% |
| 7.9 | 17.7% |
| 9.1 | 38.9% |
| 10.3 | 47.8% |
| 12.7 | 30.6% |
| 14.8 | 14.9% |
| 15.8 | 13.2% |
| 16.2 | 16.8% |
| 16.9 | 15.4% |
| 17.5 | 18.2% |
| 18.3 | 26.4% |
| 19.2 | 16.4% |
| 19.7 | 100.0% |
| 20.8 | 20.0% |
| 21.0 | 27.2% |
| 22.8 | 19.7% |
| 24.0 | 30.9% |
| 27.4 | 10.6% |
| 28.2 | 5.6% |

The crystallinity of Compound I D-tartrate was further confirmed by a Polarized Light Microscopic (PLM) image of the crystals.

Figure 10:
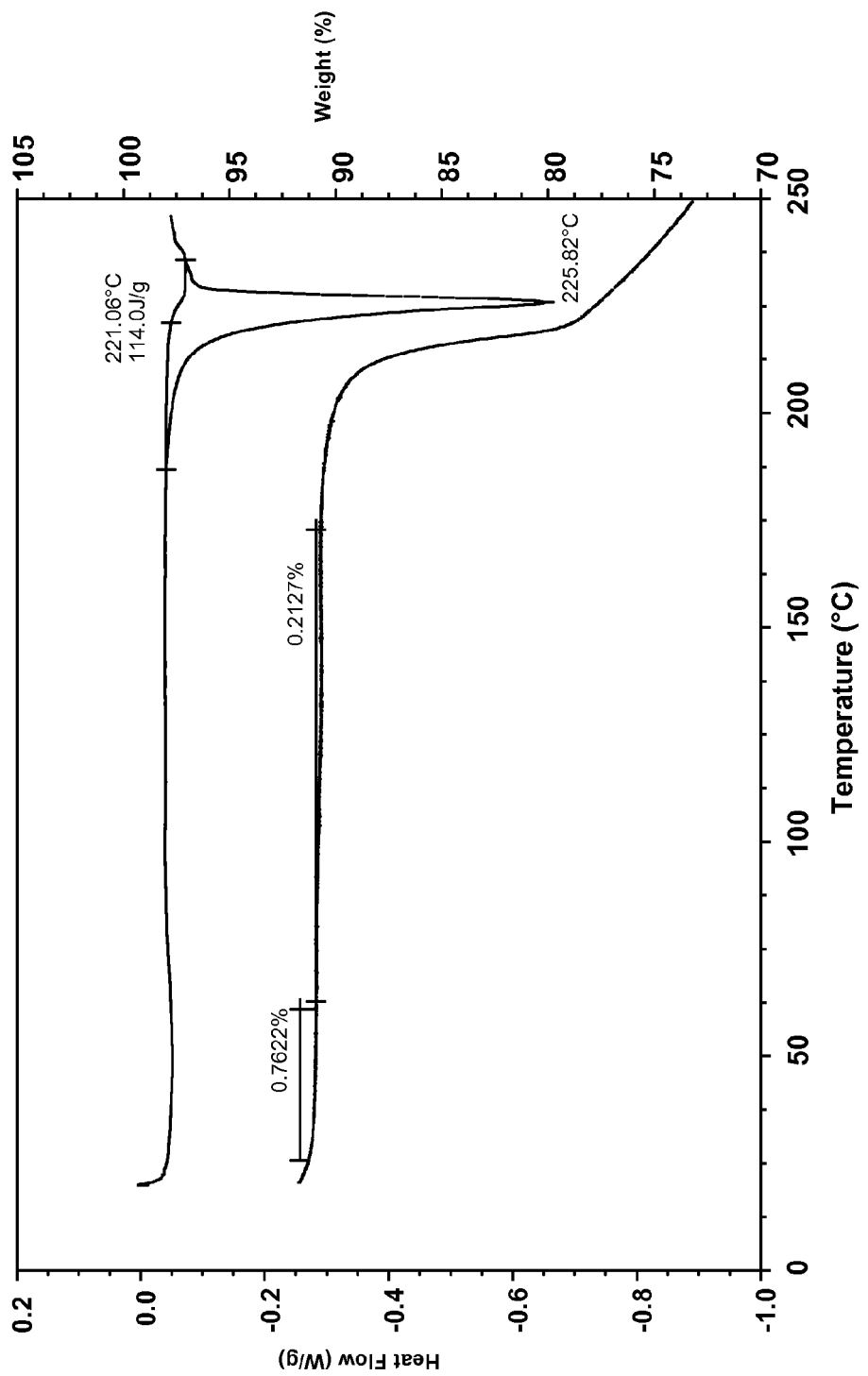
FIG. 10 is a combined differential scanning calorimetry plot (DSC; top curve) and thermogravimetric analysis (TGA; bottom curve) of Compound I D-tartrate.

The DSC curve of Compound I D-tartrate shows that upon heating this crystalline material has one sharp endotherm at 221.08° C., which indicates a clear melting event (FIG. 10). The TGA curve shows minimal weight loss, which indicates that Compound I D-tartrate is anhydrous. Dynamic vapor sorption (DVS) data demonstrated that Compound I D-tartrate takes up less than 3% moisture at 90% RH.

Example 5

Stable Form Screen for Compound I D-tartrate

Samples of Compound I D-tartrate were subjected to a screen in a manner analogous to the procedure described above in Example 1. The results for the stable form screen of Compound I D-tartrate are summarized in Table 7 below. XRPD characterization of various samples after 2 weeks showed that the physical form did not change, and only some crystallinity was lost in the water sample after 2 weeks.

TABLE 7

Stable form screen summary for Compound I D-tartrate

| Solvent | 24 hour XRPD | 2 week XRPD | Observation |
| --- | --- | --- | --- |
| Water | Compound I D-tartrate | Compound I D-tartrate | Suspension |
| IPAc | Compound I D-tartrate | Compound I D-tartrate | Suspension |
| MTBE | Compound I D-tartrate | Compound I D-tartrate | Suspension |
| 2-propanol | Compound I D-tartrate | Compound I D-tartrate | Suspension |
| THF | Compound I D-tartrate | Compound I D-tartrate | Suspension |
| Methanol | Compound I D-tartrate | Compound I D-tartrate | Suspension |
| ACN | Compound I D-tartrate | Compound I D-tartrate | Suspension |
| Ethanol | Compound I D-tartrate | Compound I D-tartrate | Suspension |
| Ethyl acetate | Compound I D-tartrate | Compound I D-tartrate | Suspension |
| 2-MeTHF | Compound I D-tartrate | Compound I D-tartrate | Suspension |
| MEK | Compound I D-tartrate | Compound I D-tartrate | Suspension |
| MIBK | Compound I D-tartrate | Compound I D-tartrate | Suspension |
| n-heptane | Compound I D-tartrate | Compound I D-tartrate | Suspension |
| DCM | Compound I D-tartrate | Compound I D-tartrate | Suspension |
| $a_w$ of 0.8 (EtOH/water) | Compound I D-tartrate | Compound I D-tartrate | Suspension |

Example 6

Figure 11:
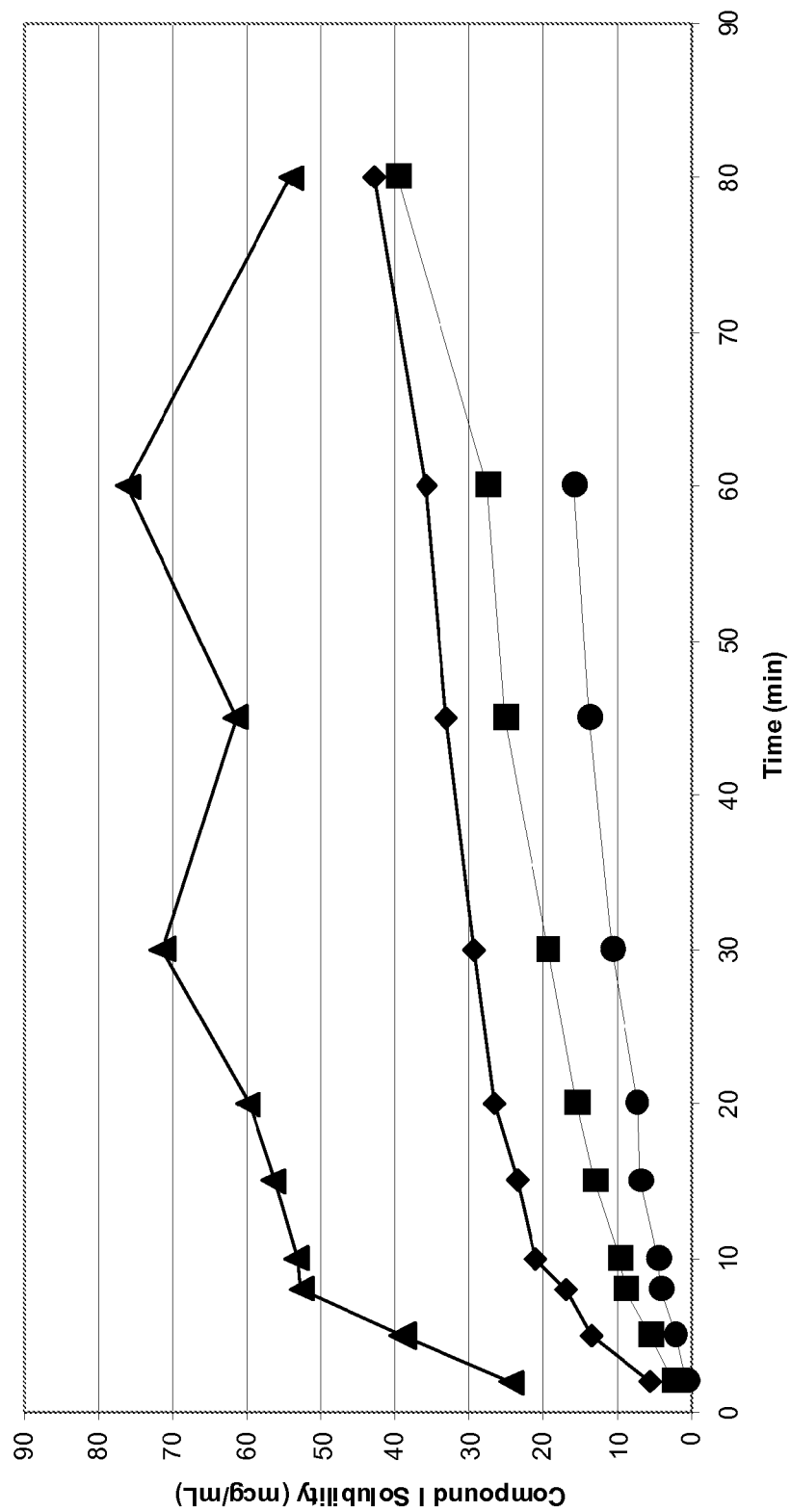
FIG. 11 is a chart that compares dissolution rates between amorphous Compound I (♦), Compound I Form II (●), Compound I Form III (■), and Compound I D-tartrate (▲).

Kinetic Solubility and Photostability Evaluation of Compound I D-tartrate in Comparison to Other Forms The dissolution rate of Compound I D-tartrate in water at pH 3 is 5 to 10 times faster than any other form of Compound I described herein. Compound I D-tartrate also resulted in sustained solubility increases (~2×) for an extended timeframe. In contrast, Compound I Form II resulted in the slowest dissolution rate. These results and others are shown in FIG. 11. These results show that Compound I D-tartrate exhibits improved dissolution properties in moderately acidic aqueous media.

Figure 12:
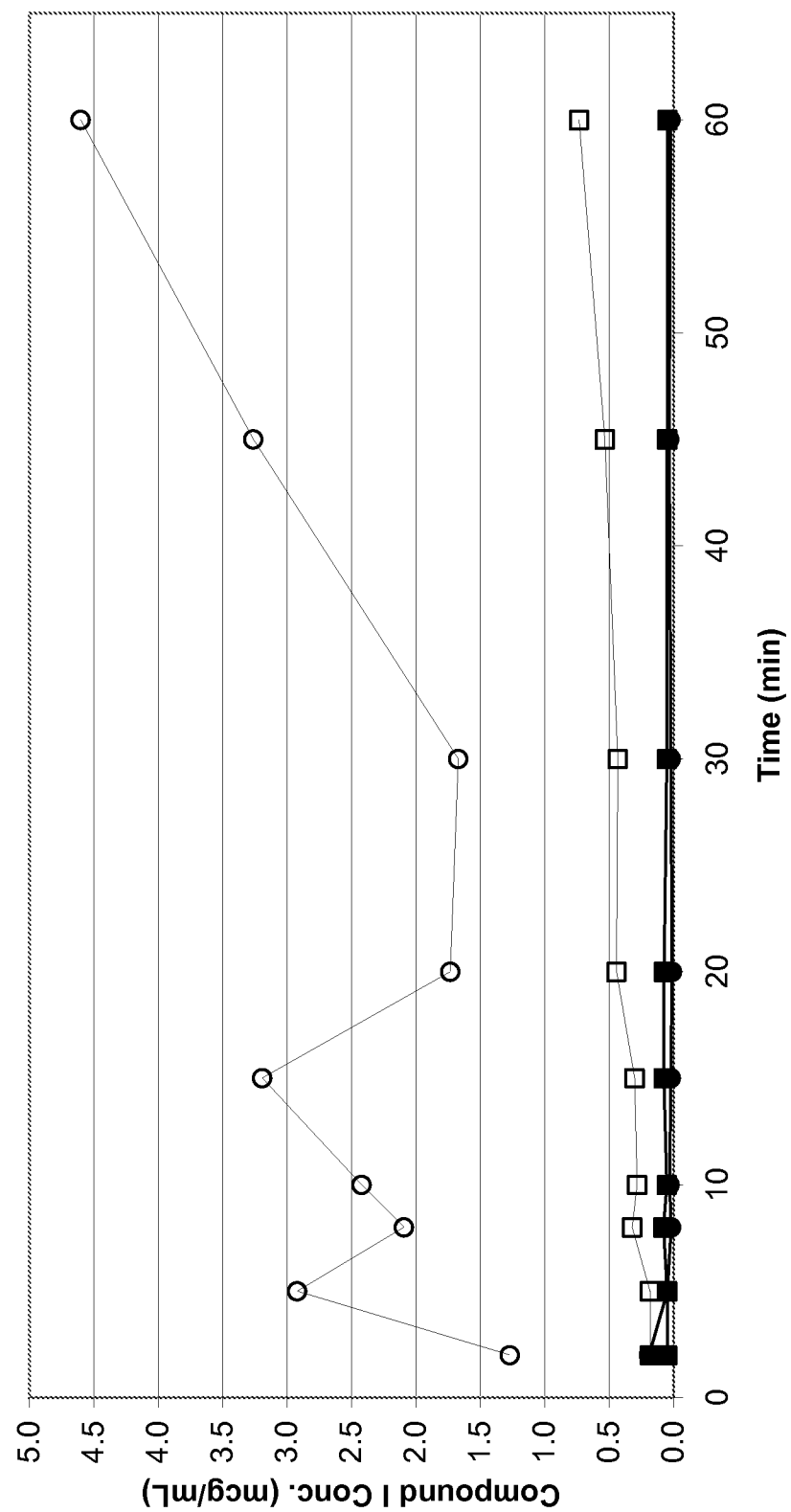
FIG. 12 is a chart that compares dissolution rates between aqueous samples (pH 6) of amorphous Compound I (■), a mixture of amorphous Compound I and 0.1% (w/w) HPMC (□), Compound I D-tartrate (●), and Compound I D-tartrate with 0.1% (w/w) HPMC (○). Plots for Compound I (■) and Compound I D-tartrate (●) essentially are superimposed at the displayed vertical scale.

Because the solubility of Compound I over a greater pH range is less than about 1 µg/mL, a further experiment was conducted to assess kinetic solubility of Compound I at a higher pH, here pH 6. In this experiment, dissolution rates were measured for samples of amorphous Compound I and Compound I D-tartrate, and samples of each form admixed with 0.1% (w/w) hydroxypropylmethyl cellulose (HPMC) in aqueous media at pH 6. As shown in FIG. 12, the presence of HPMC improved dissolution and solubility over a 60 minute period. Specifically, about a 100-fold enhancement was observed for the mixture of Compound I D-tartrate and HPMC (steady-state solubility=0.02 µg/mL). The results demonstrated the potential advantage of the D-tartrate over all freebase forms of Compound I using certain formulation techniques.

Figure 13:
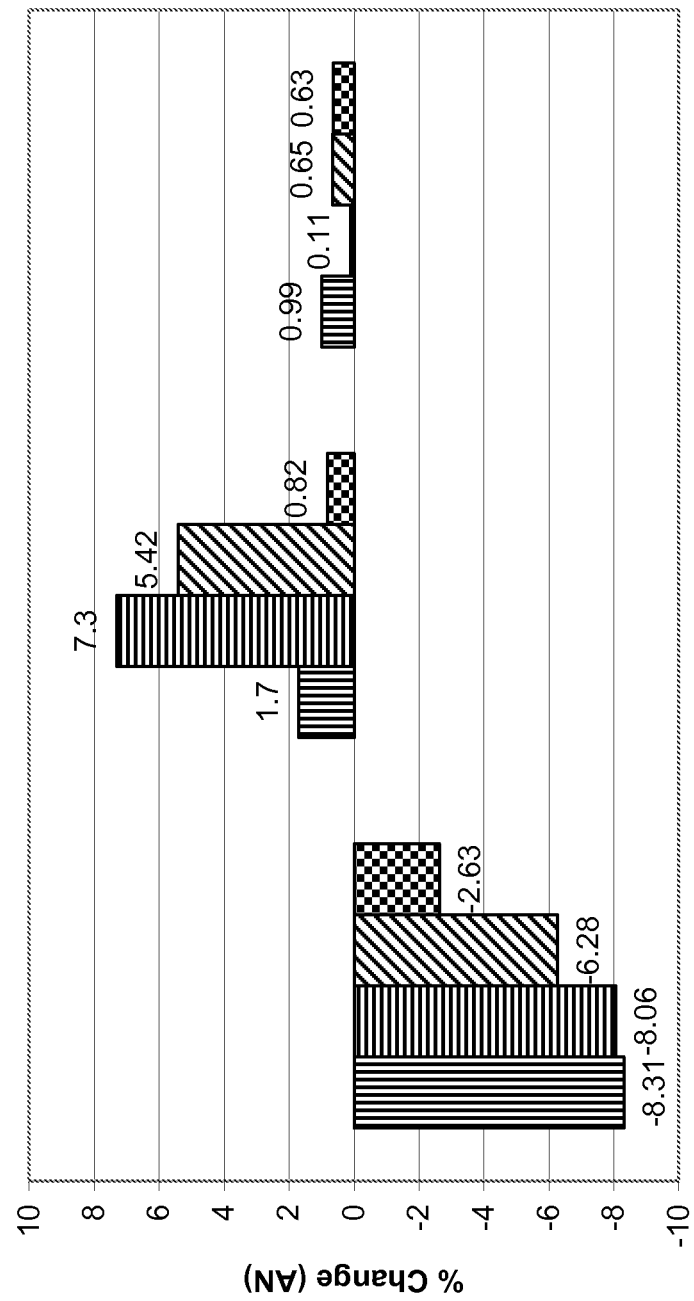
FIG. 13 compares the photodegradation behaviors of amorphous Compound I (vertical stripes), Compound I Form III (horizontal stripes), Compound I Form II (diagonal stripes), and Compound I D-tartrate (checkerboard) during photoexposure at 1.2 M Lux-hrs. The leftmost group of bars represents the overall decrease in HPLC % AN of these four forms of Compound I. The middle group of bars represents the formation of a primary photodegradation impurity, resulting from each form of Compound I. The rightmost group of bars similarly represents the formation of a secondary photodegradation impurity that eluted on HPLC at relative retention time (RRT) 1.67.

Photochemical degradation of Compound I was evaluated in a SUNtest chamber over 8 hours (1.2M lux-hrs). The results showed the presence of a primary photodegradant in solution, and less so as a solid (FIG. 13). A secondary photodegradant at relative retention time (RRT) 1.67 was formed by light exposure or exposure to chemical oxidizers (primary DP degradant). The results showed that crystallization of Compound I results generally in more robust stability in presence of light. In particular, the results demonstrate that Compound I D-tartrate is the most robust form in presence of light relative to other forms of Compound I described herein.

Example 7

Polymorph Screen

The purpose of this example is to illustrate the synthesis and characterization of additional crystalline forms of Compound I. As described in detail below, eleven additional solvate forms and two anhydrous forms of Compound I were discovered in a stable form screen. The two new anhydrous forms were generated by desolvation of the solvate forms. Upon exposure to organic solvents, the anhydrous forms dissolve, become amorphous, or convert to solvate forms.

A. Stable Form Screen

In a manner analogous to that described above in Example 1, the stable form screen was conducted by stirring 100 to 200 mg of Compound I Form III in 2 mL of various solvents at ambient temperature (~22° C.). After a few days, heptane was added as antisolvent to those samples that remained as solutions. In instances where slurries formed, the slurries were sampled and centrifuged for XRPD analysis, as described more fully below. Table 8 summarizes the result of the stable form screen, indicating where applicable the formation of a new form of Compound I.

TABLE 8

Results from Additional Stable Form Screen

| Solvent | Initial form (1 d) | Heptane added? | Final form (2 w) | Notes |
| --- | --- | --- | --- | --- |
| Water | amorphous | N | amorphous | |
| EtOH/water | amorphous | N | amorphous | |
| ACN | amorphous | Y | Form X | ACN solvate |
| MeOH | solution | N | solution | Immiscible with heptane |
| EtOH | solution | Y | amorphous | |
| IPA | solution | Y | solution | |
| MEK | solution | Y | Form XII | MEK solvate, isostructural with THF solvate |
| MIBK | solution | Y | solution | |
| DCM | solution | Y | solution | |
| THF | solution | Y | Form XI | THF solvate, isostructural with MEK solvate |
| 2Me-THF | solution | Y | amorphous | |
| Ethyl | Form IX | N | Form IX | Ethyl formate solvate |
| Methyl | Form VII | N | Form VII | Methyl acetate solvate |
| EtOAc | Form IV | N | Form IV | Ethyl acetate solvate |
| IPAc | Form VI | N | Form VI | Isopropyl acetate solvate |
| n-propyl | solution | Y | amorphous | |
| n-butyl | solution | Y | amorphous | |
| MTBE | amorphous | N | amorphous | |
| Toluene | solution | Y | amorphous | |
| Heptane | amorphous | N | amorphous | |

B. Desolvation of Compound I Solvates

The Compound I solvates that were synthesized from the polymorph screen described above were desolvated under various conditions. As a result, several additional forms of Compound I were found. The experimental conditions and results based on TGA data are summarized below in Table 9, which indicates where applicable the formation of crystalline forms of Compound I.

TABLE 9

Results of Desolvation of Compound I Solvates

| Solvated Form | Description | Desolvated form | Desolvation temperature (° C.) |
|---|---|---|---|
| Form IV | EtOAc solvate | Form V (Partially desolvated) | Room temperature |
| Form V | Partially desolvated | amorphous | 90 |
| Form VI | IPAc solvate | amorphous | 80-125 |
| Form VII | MeOAc solvate | Form VIII | 30-75 |
| Form IX | Ethyl formate solvate | Form VIII | 40-150 |
| Form X | ACN solvate | Form XV | 80-150 |
| Form XI | THF solvate | Form XIII (partially desolvated) | 40 |
| Form XII | MEK solvate | Form XIII (partially desolvated) | 40 |
| Form XIV | MTBE solvate | Form VIII | 30-150 |

C. Compatibility of Anhydrous Compound I Forms with Various Solvents

To explore the possibility of direct crystallization of the solvated forms of Compound I summarized above, desolvated forms of Compound I were individually dispersed into some commonly used solvents. In general, it was observed that the desolvated forms of Compound I were not compatible with those solvents, except for Form VIII in water and heptane.

In addition, Compound I Form VIII converted in MTBE to Compound I Form XIV, which exhibits an XRPD pattern similar to that of Compound I Form X (an ACN solvate). Therefore, it was concluded that the MTBE solvate and ACN solvate are isostructural; however, these two solvates were observed to desolvate to different forms upon drying: Form X desolvates to Form XV and Form XIV desolvates to Form VIII, as described above. Table 10 below summarizes the results of experiments concerning the desolvated forms of Compound I.

TABLE 10

Final forms from experiments in which anhydrous forms of Compound I were stirred in various solvents

| Solvent | Form III | Form V | Form VIII | Form XV |
|---|---|---|---|---|
| Water | amorphous | amorphous | VIII | amorphous |
| EtOH/water | amorphous | amorphous | amorphous | amorphous |
| ACN | amorphous | amorphous | Form X (ACN solvate) | Form X (ACN solvate) |
| ACN/water | Oil out | Oil out | Oil out | Oil out |
| IPA | solution | solution | solution | solution |
| MEK | solution | solution | solution | solution |
| MIBK | solution | solution | solution | solution |
| THF | solution | solution | solution | solution |
| 2Me-THF | solution | solution | solution | solution |
| Methyl acetate | Form VII | Form VII | Form VII | Form VII |
| EtOAc | Form IV | Form IV | From IV | From IV |
| MTBE | amorphous | amorphous | Form XIV (MTBE solvate) | solution |
| Toluene | solution | amorphous | amorphous | solution |
| Heptane | amorphous | amorphous | VIII + VII (sticky) | amorphous |

Example 8

Characterization of Compound I Forms IV-XV

This example presents details on characterizing data for Compound I Forms IV-XV that were synthesized as described above.

A. Forms IV and V

Single crystals of Compound I Form IV were subjected to single crystal X-ray diffraction analysis, the results of which are summarized in Table 11 below.

TABLE 11

Summary of Single Crystal X-ray Diffraction Analysis of Compound I Form IV

| Crystal system | Monoclinic | |
|---|---|---|
| Space group | P2(1) | |
| Unit cell dimensions | a = 15.7470(5) Å | $\alpha = 90°$. |
| | b = 10.6245(4) Å | $\beta = 95.149(2)°$. |
| | c = 18.3114(6) Å | $\gamma = 90°$. |
| Density (calculated) | 1.255 Mg/m$^3$ | |

Compound I Form IV is a tri-ethyl acetate solvate according to the single crystal XRD and it easily loses EtOAc during drying. Thus, Compound I Form V was obtained when form IV was partially desolvated at 40-50° C. under vacuum. TGA analysis showed that Form V lost 2.7% mass when heated to 110° C., indicating that Form V likely is a partial ethyl acetate solvate. Form V became amorphous upon drying at 110° C. The melting point of Form V is about 160° C.

Figure 14:
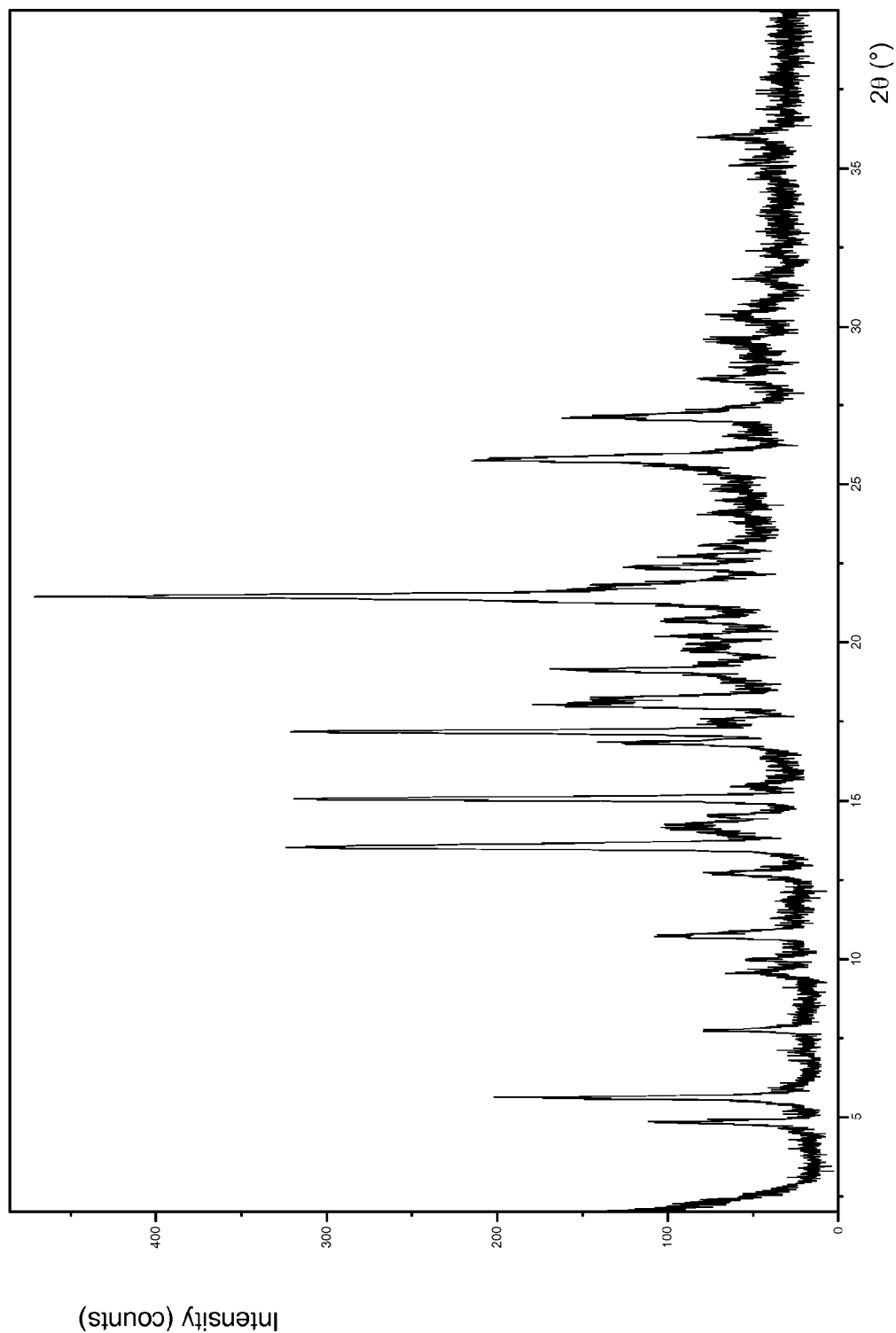
FIG. 14 is an X-ray powder diffraction pattern of Compound I Form IV.
Figure 16:
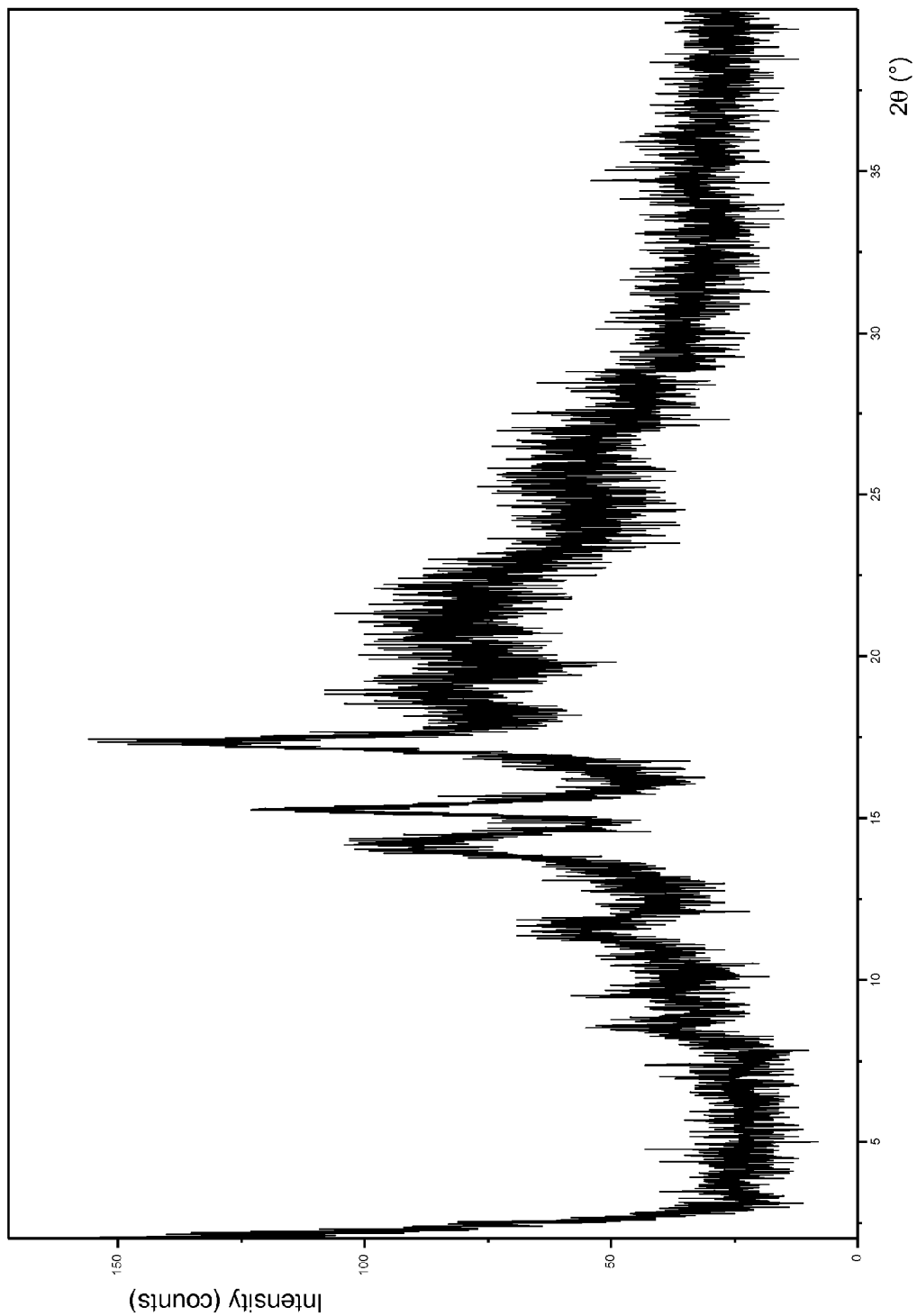
FIG. 16 is an X-ray powder diffraction pattern of Compound I Form V.

The XRPD patterns of Forms IV and V are shown in FIGS. 14 and 16, respectively. XRPD peak listings and relative intensities are tabulated below in Tables 12 and 13, respectively.

TABLE 12

XRPD Peaks and Relative Intensities for Compound I Form IV

| Position (° 2θ) | Relative Intensity (%) |
|---|---|
| 4.8 | 18.3 |
| 5.6 | 37.1 |
| 7.7 | 13.0 |
| 9.6 | 7.5 |
| 10.7 | 19.9 |
| 12.7 | 11.7 |
| 13.5 | 64.1 |
| 14.2 | 14.2 |
| 15.1 | 67.85 |
| 16.8 | 22.1 |
| 17.2 | 65.9 |
| 18.0 | 29.6 |
| 19.2 | 27.8 |
| 20.7 | 13.2 |
| 21.5 | 100 |
| 22.4 | 17.0 |
| 25.8 | 37.8 |
| 27.1 | 21.8 |

TABLE 13

XRPD Peaks and Relative Intensities for Compound I Form V

| Position (° 2θ) | Relative Intensity (%) |
|---|---|
| 8.6 | 11.6 |
| 11.8 | 20.0 |

TABLE 13-continued

XRPD Peaks and Relative Intensities for Compound I Form V

| Position (° 2θ) | Relative Intensity (%) |
|---|---|
| 14.4 | 58.9 |
| 15.3 | 97.3 |
| 17.4 | 100.0 |
| 18.9 | 9.2 |

Figure 15:
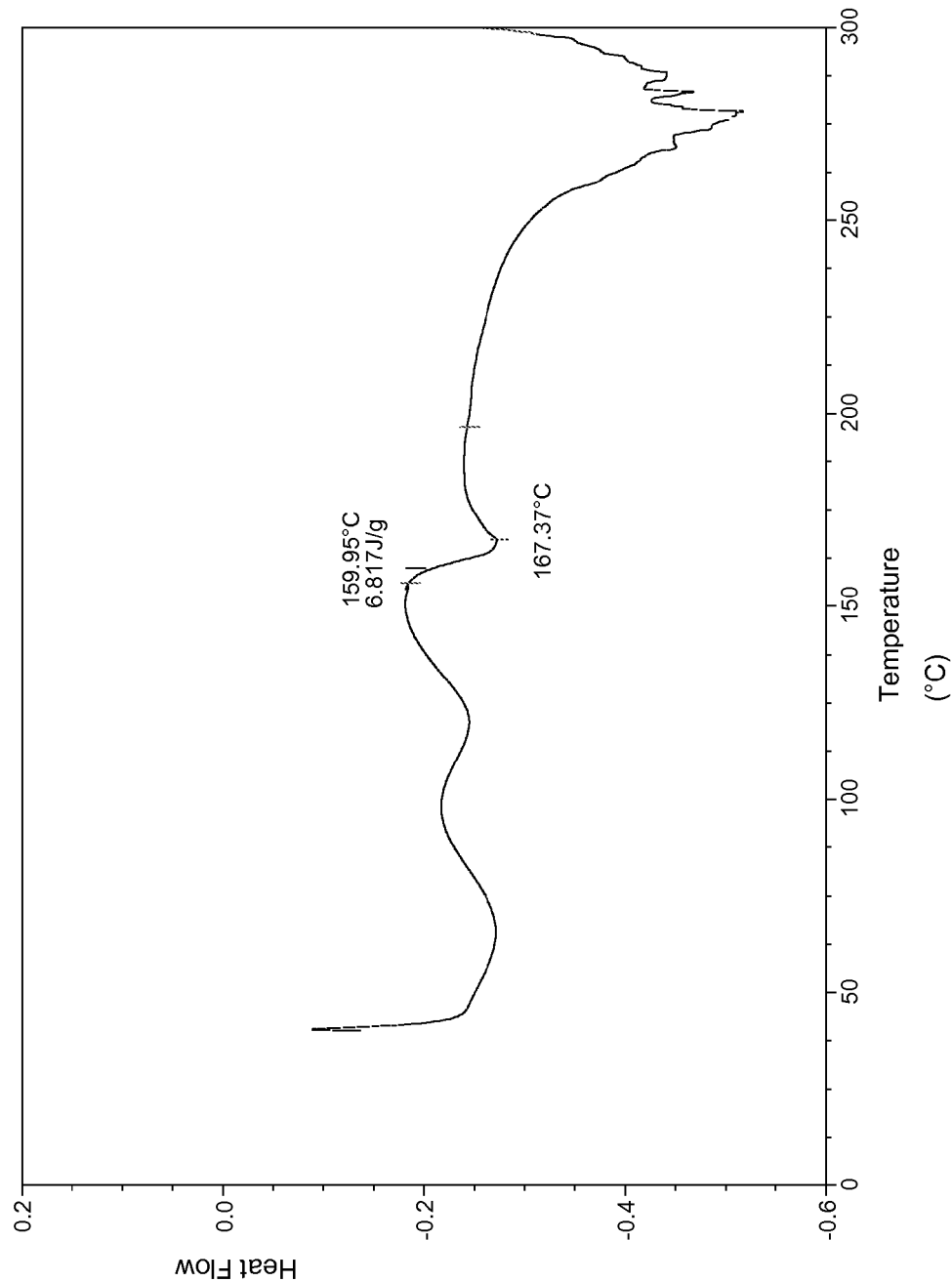
FIG. 15 is differential scanning calorimetry (DSC) curve of Compound I Form IV.

The DSC curve for Form IV is shown in FIG. 15. In addition, DVS data showed that Form V is non-hygroscopic.

B. Form VI

Form VI was obtained from IPAc following the general procedure outlined above. TGA data showed Form VI is a solvated form (22.8% weight loss at 135° C.). When Form VI was heated, the XRPD peaks broadened but no new peaks appeared, suggesting there were no new forms generated upon heating. The XRPD diffractogram is shown in FIG. 17; peaks and relative intensities are tabulated in Table 14 below. The DSC curve is shown in FIG. 18.

TABLE 14

XRPD Peaks and Relative Intensities for Compound I Form VI

| Position (° 2θ) | Relative Intensity (%) |
|---|---|
| 4.8 | 12.8 |
| 5.6 | 100.0 |
| 7.8 | 10.2 |
| 10.5 | 11.9 |
| 13.3 | 53.1 |
| 13.8 | 17.3 |
| 14.2 | 13.1 |
| 14.8 | 24.4 |
| 16.7 | 16.8 |
| 16.9 | 17.8 |
| 18.0 | 12.4 |
| 18.2 | 14.3 |
| 19.1 | 12.3 |
| 21.1 | 60.1 |

C. Forms VII and VIII

Compound I Form VII was obtained from a methyl acetate solution of Compound I. Form [[VIII]] VII is a methyl acetate solvate, and it desolvates to become Form VIII, an anhydrous form. The XRPD patterns of these two forms are shown in FIGS. 19 and 20, respectively. Tables 15 and 16 below tabulate XRPD peaks and relative intensities. In addition, FIG. 18 shows the DSC curve for Form VIII.

TABLE 15

XRPD Peaks and Relative Intensities for Compound I Form VII

| Position (° 2θ) | Relative Intensity (%) |
|---|---|
| 8.1 | 25.7 |
| 8.8 | 16.0 |
| 9.3 | 30.8 |
| 11.0 | 43.5 |
| 13.8 | 100.0 |
| 14.1 | 33.0 |
| 16.4 | 33.8 |
| 17.0 | 41.6 |
| 18.2 | 30.8 |
| 19.0 | 43.4 |
| 19.5 | 39.7 |
| 20.2 | 28.1 |

TABLE 15-continued

XRPD Peaks and Relative Intensities for Compound I Form VII

| Position (° 2θ) | Relative Intensity (%) |
|---|---|
| 22.2 | 88.4 |
| 25.2 | 38.2 |
| 26.5 | 19.8 |

TABLE 16

XRPD Peaks and Relative Intensities for Compound I Form VIII

| Position (° 2θ) | Relative Intensity (%) |
|---|---|
| 9.4 | 100.0 |
| 11.8 | 12.0 |
| 12.2 | 31.4 |
| 12.7 | 20.8 |
| 14.6 | 67.1 |
| 15.5 | 83.7 |
| 16.8 | 20.1 |
| 17.2 | 25.9 |
| 17.5 | 89.1 |
| 18.4 | 15.6 |
| 18.8 | 45.0 |
| 20.3 | 16.3 |
| 20.9 | 21.2 |
| 21.6 | 23.2 |
| 22.6 | 11.8 |

TGA data for Form VIII showed a small weight loss below 50° C. even if Form VIII was dried at 50° C. under vacuum. Karl Fischer analysis showed a water content of 1.8% after drying in a vacuum oven at 50° C., confirming that the weight loss was caused by loss of water. The source of water is believed to be moisture in the air during material transfer. A slurry test in water showed that Form VIII is stable in water. DVS data showed that Form VIII absorbs roughly one equivalent of water, suggesting that Form VIII exists as a monohydrate in water. Hence, an advantage of Form VIII is that it can be obtained by desolvating form VII at lower temperature, even at room temperature under vacuum conditions.

D. Form IX

Compound I Form IX is solvate form that is obtained in ethyl formate. The XRPD diffractogram is shown in FIG. 22; Table 17 below tabulates XRPD peaks and relative intensities.

TABLE 17

XRPD Peaks and Relative Intensities for Compound I Form IX

| Position (° 2θ) | Relative Intensity (%) |
|---|---|
| 8.2 | 21.7 |
| 9.4 | 13.3 |
| 11.0 | 37.4 |
| 12.6 | 12.5 |
| 13.8 | 100.0 |
| 16.1 | 17.2 |
| 17.1 | 50.8 |
| 17.7 | 13.7 |
| 18.4 | 18.7 |
| 19.2 | 54.5 |
| 19.6 | 15.1 |
| 20.4 | 21.5 |
| 21.9 | 98.4 |
| 24.7 | 20.1 |

TGA data shows Form IX loses 5.9% mass before melting; the DSC curve is shown in FIG. 23. XRPD (FIG. 27) shows that this form desolvates to become Form VIII.

E. Forms X and XIV

Compound I Form X is an acetonitrile solvate and Form XIV is an MTBE solvate. Forms X and XIV exhibit very similar XRPD patterns, as shown in FIGS. 24 and 31, respectively. TGA data for these forms, however, are quite different. Upon drying, Form X became Form XV, an anhydrous form of Compound I as described more fully below, and Form XIV became Form VIII as described above. Tables 18 and 19 below tabulate XRPD peaks and relative intensities for Forms X and XIV, respectively.

TABLE 18

XRPD Peaks and Relative Intensities for Compound I Form X

| Position (° 2θ) | Relative Intensity (%) |
|---|---|
| 3.4 | 7.8 |
| 6.9 | 100.0 |
| 10.3 | 46.5 |
| 11.2 | 3.6 |
| 20.0 | 5.6 |
| 22.4 | 7.3 |

TABLE 19

XRPD Peaks and Relative Intensities for Compound I Form XIV

| Position (° 2θ) | Relative Intensity (%) |
|---|---|
| 3.4 | 10.8 |
| 6.9 | 100.0 |
| 10.3 | 40.6 |
| 11.2 | 9.4 |
| 12.3 | 5.3 |
| 12.6 | 3.9 |
| 12.9 | 4.1 |
| 14.2 | 3.2 |
| 17.3 | 4.2 |
| 20.1 | 11.6 |
| 21.3 | 4.1 |
| 22.4 | 11.7 |
| 24.1 | 6.1 |

F. Forms XI, XII, and XIII

Form XI is a THF solvate and form XII is an MEK solvate. The two forms have very similar XRPD patterns, as shown in FIGS. 24 and 25, respectively. Tables 20 and 21 below tabulate XRPD peaks and relative intensities for Forms XI and XII, respectively.

TABLE 20

XRPD Peaks and Relative Intensities for Compound I Form XI

| Position (° 2θ) | Relative Intensity (%) |
|---|---|
| 3.2 | 66.2 |
| 6.3 | 100.0 |
| 9.5 | 78.4 |
| 11.8 | 9.1 |
| 12.3 | 15.9 |
| 12.9 | 6.4 |
| 14.7 | 7.2 |
| 15.4 | 14.7 |
| 16.1 | 9.2 |
| 18.2 | 12.7 |
| 19.1 | 25.8 |
| 20.3 | 17.5 |
| 20.6 | 26.7 |
| 21.0 | 14.2 |
| 22.5 | 32.8 |
| 23.2 | 16.9 |
| 24.7 | 14.6 |

TABLE 21

XRPD Peaks and Relative Intensities for Compound I Form XII

| Position (° 2θ) | Relative Intensity (%) |
|---|---|
| 3.2 | 88.9 |
| 6.4 | 100.0 |
| 8.6 | 29.0 |
| 9.6 | 47.5 |
| 12.2 | 35.6 |
| 18.1 | 40.8 |
| 18.4 | 22.1 |
| 19.3 | 33.5 |
| 19.7 | 32.5 |
| 20.6 | 84.3 |
| 21.0 | 32.5 |
| 22.5 | 47.2 |

Upon drying in a vacuum oven at room temperature, Forms XI and XII partially lost their solvents and became Form XIII-THF and Form XIII-MEK, respectively. NMR analysis of vacuum oven dried samples of Form XIII-THF and Form XIII-MEK showed the existence of solvents in these forms, ~0.9 and ~1.1 molar equivalent, respectively. In addition, DSC curves for Form XIII-THF and Form XIII-MEK are different, as shown in FIGS. 28 and 30, respectively. Therefore, it was concluded that Forms XIII-THF and XIII-MEK are partial solvates of THF and MEK, respectively. XRPD analyses demonstrated that the THF and MEK partial solvates are identical, as shown in FIGS. 27 and 29, respectively. XRPD peaks and relative intensities for Forms XIII-THF and XIII-MEK are tabulated below in table 22.

TABLE 22

XRPD Peaks and Relative Intensities for Compound I Forms XIII-THF and XIII-MEK

| Position (° 2θ) | Relative Intensity (%) |
|---|---|
| 3.2 | 44.1 |
| 3.5 | 46.5 |
| 7.0 | 19.0 |
| 8.6 | 36.3 |
| 12.1 | 100.0 |
| 19.8 | 92.9 |
| 20.2 | 69.3 |
| 22.6 | 34.2 |
| 24.4 | 20.7 |

F. Form XV

As mentioned above, Compound I Form X became Form XV upon drying at room temperature under vacuum. Form XV is an anhydrous and non-hygroscopic crystalline form of Compound I, as shown by TGA and DVS experiments. FIG. 32 depicts the XRPD diffractogram and Table 23 below summarizes major peaks and their relative intensities.

TABLE 23

XRPD Peaks and Relative Intensities for Compound I Form XV

| Position (° 2θ) | Relative Intensity (%) |
|---|---|
| 7.6 | 34.7 |
| 9.1 | 45.1 |
| 10.9 | 38.4 |
| 11.4 | 27.2 |
| 12.1 | 100.0 |
| 12.8 | 53.0 |
| 13.5 | 19.4 |
| 15.1 | 17.0 |
| 16.7 | 18.2 |
| 17.4 | 22.9 |
| 18.0 | 23.5 |
| 19.4 | 34.4 |
| 20.8 | 70.8 |
| 21.3 | 43.1 |

Form XV exhibits a slightly higher melting point than other Forms of Compound I described herein, according to DSC data (FIG. 38).

Example 9

Comparison of Compound I Forms I-XV

In Table 24 below, TGA and DSC data are compiled for all crystalline forms of Compound I as disclosed herein. The melting point of the anhydrous forms, III, V, VIII, XIV are all in the range 160-172° C. The desolvation temperatures differ greatly.

TABLE 24

Comparison of Thermal Data for Compound I Forms I-XV

| Form | Description | Melting point (° C.) | Weight Loss (%) | Desolvated Form |
|---|---|---|---|---|
| I | Diacetone solvate | | 12.2% @ 160° C. | II |
| II | Monoacetone solvate | | 7.7% @150° C. | III |
| III | Anhydrous | 170.7 | | — |
| IV | EtOAc solvate | | 15% 100° C. | V |
| V | Partial EtOAc solvate | 160.7 | 2.7 @115° C. | amorphous |
| VI | IPAc solvate | | 22.80% @ 135° C. | amorphous |
| VII | MeOAc solvate | | 8.8% @ 100° C. | VIII |
| VIII | Anhydrous | 164~169 | 1.11% @75° C. | — |
| IX | Ethyl formate solvate | | 7% @110° C. | VIII |
| X | ACN solvate | | 2.9% @ 90° C., 13% @ 170° C. (ACN) | XV |
| XI | THF solvate | 142.3 | 11.6% at 150° C. (THF) | Form XIII |
| XII | MEK solvate | 146 | 9.7% at 150° C. (MEK) | |
| XIII | Partial solvate of THF or MEK | | | |
| XIV | MTBE solvate | | 5.9% @ 160° C. (MTBE) | VIII |
| XV | Anhydrous | 168~172 | | — |

Example 10

Synthesis of Amorphous Compound I

The following steps discuss the synthesis of amorphous Compound I. The synthesis of acetone solvate of Compound I is also described in U.S. Application Ser. No. 61/655,935 filed on Jun. 5, 2012, which is incorporated herein by reference.

I. Synthesis of Starting Materials

A. Iodination of Diol 6 to Prepare 7a

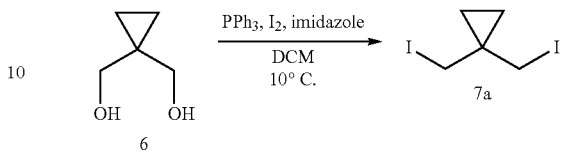

Triphenylphospine (257.2 g) and imidazole (66.7 g) were charged to a reactor. DCM (490 mL) was charged, agitation was initiated and the solution was cooled to 0° C. Iodine (249.2 g) was added as a solid portion-wise over 1 h while maintaining the internal temperature below 10° C. Upon completion of the addition, a solution of 6 (50 g) in DCM (113 mL) was slowly charged to the reactor over 0.5 h while maintaining the internal temperature below 10° C. After stirring for 2.5 h, an aqueous solution of NaCl (25 g) in water (225 mL) was charged to the reactor. Following phase separation, the bottom organic layer was diluted with n-heptane (550 mL). The organic phase was washed with an aqueous solution of sodium sulfite (21 g) in water (190 mL). Following layer separation, the organic phase was concentrated to 600 mL via vacuum distillation. Additional n-heptane (550 mL) was charged, and the mixture was again concentrated to 600 mL via vacuum distillation. The resulting slurry was filtered over a silica gel plug (85 g) that had been slurry packed with n-heptane. The silica gel plug was rinsed with additional n-heptane (1 L), and the filtrate was then concentrated via vacuum distillation to provide the desired product 7a as a colorless liquid (114 g, 70%). $^1$H NMR (400 MHz, CDCl$_3$) δ 3.33 (s, 2H), 0.95 (s, 2H). $^{13}$C NMR (75 MHz, CDCl$_3$): 19.1, 22.7, 26.0.

B. Alkylation of 8 to Prepare 9

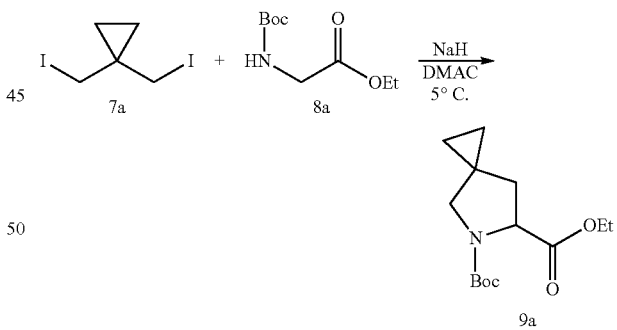

Sodium hydride (60.0 g, 3 equivalents, 60% dispersion in mineral oil) and dimethylacetamide (600 mL) were charged to a flask and the reaction temperature was lowered to 0-10° C. Compound 7a (191.6 g, 1 equivalent) was charged to the NaH solution once the internal temperature was approximately 5° C. A solution of compound 8a (121.0 g, 1 equivalent) in DMAC (600 mL) was added over 3.5 h, keeping the internal temperature between 0-11° C. The solution was stirred at 0-10° C. and sampled for reaction completion after 1 h. The reaction was considered complete when the remaining amount of 8a was less than 3%. Upon completion, AcOH (50 mL, 1.5 equivalents) was slowly added over 2-3 h while keeping the temperature between 4-9° C. The solution was stirred for 12 h at 0-10° C. MTBE (1000 mL) and water (700 mL) were added to the quenched solution. The layers were separated and the aqueous layer was extracted with MTBE (400 mL). The organic layers were combined and washed once with a 15% NaCl solution (1000 mL), once with a 5% sodium bicarbonate solution (900 mL) and once with a brine solution (600 mL). The MTBE solution was concentrated to a minimum volume. The oil was re-dissolved in ACN (400 mL) and washed with hexanes (200 mL). The phases were separated, the ACN layer was concentrated to a minimum volume and the hexanes layer was discarded. The product 9a was isolated as a yellow oil (98 g, 61%). $^1$H NMR (400 MHz, CDCl$_3$) δ 4.45 (dd, J=8.5, 3.7 Hz, 0.5H rotamer 1), 4.35 (dd, J=8.4, 4.4 Hz, 0.5H rotamer 2), 4.27-4.11 (m, 2H), 3.44-3.29 (m, 2H), 2.26 (ddd, J=12.7, 8.4, 4.1 Hz, 1H), 1.80 (ddd, J=23.5, 12.6, 4.0 Hz, 1H), 1.58, 1.48-1.40 (m, 9H), 1.32-1.21 (m, 3H), 0.68-0.44 (m, 4H).

C. Hydrolysis of Ethyl Ester 9a

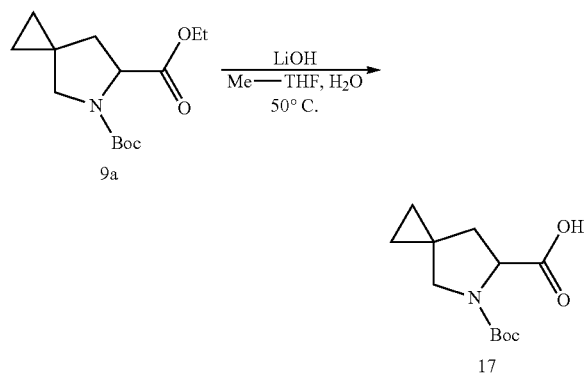

Water (910 mL), lithium hydroxide (284 g, 2.0 eq) and 2-MeTHF (2.0 L) were added to a flask equipped with overhead stirring, an internal thermometer and a nitrogen line. A solution of compound 9a (911 g) in 2-MeTHF (1.0 L) was transferred into the flask containing the lithium hydroxide. The reaction was heated to 50° C. until the reaction was deemed complete as determined by HPLC analysis. The reaction was cooled to 22° C. and water (3.6 L) was added to the reaction. The layers were split and the bottom aqueous layer was retained while the upper organic layer was eliminated. 2-MeTHF (4 L) and concentrated HCl (420 mL) were added to the aqueous layer. The layers were separated and the bottom aqueous layer removed. The upper organic layer was concentrated and the product 17 isolated as a white solid (596 g, 71%). Characterization data for 17 is the same as for compound 4 described above.

D. Classical Resolution

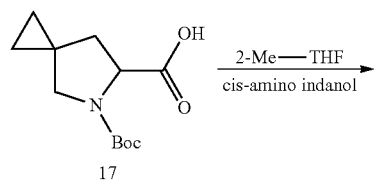

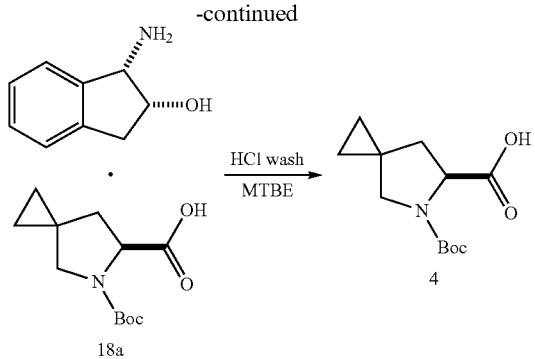

Racemic carboxylic acid 17 (596 g) was dissolved in 2-Me-THF (6 L) and then the homogenous solution was heated to 55° C. (1S,2R)-amino-indanol (221 g, 0.6 eq) was added to the reaction in 3 equal portions 10 minutes apart. The solution was seeded with salt 18a (0.6 g) after the first portion had been added. After the last portion of amine was added the solution was aged at 55° C. for 1 h. The slurry was then cooled to 22° C. at a rate of ~15 degrees per hour. Once the slurry had reached room temperature it was filtered and the cake was washed once with 2-Me-THF (1.2 L). The solids were dried at 45° C. in a vacuum oven for 24 h. Compound 18a was isolated as a white solid (320 g, 33%).

The solids 18a were dissolved in MeTHF (1.5 L), 1M HCl (1.0 L) was added and the biphasic mixture stirred 30 min until the solids were dissolved. The lower aqueous layer was removed and the organic layer was washed with 1M HCl (1 L) and then H$_2$O (500 mL). The organic layer was dried over MgSO$_4$ (250 g each) for 20 min, filtered and the cake was washed with MeTHF. This same drying procedure was repeated a second time and then the solution was concentrated to an oil to yield 4 (197 g, 100%).

E. Potassium Salt Formation

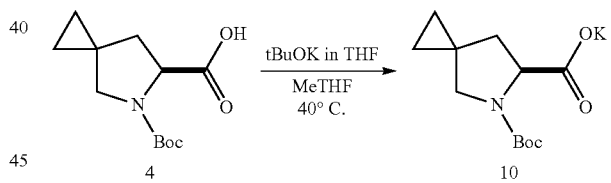

Carboxylic acid 4 (219 g) was dissolved in 2-MeTHF (880 mL) and then the solution was heated to about 35° C. 1.0 M tBuOK solution in THF (1.05 L) was slowly added such that the internal temperature did not exceed 40° C. The slurry was agitated for about 30 minutes and then slowly cooled to about 20° C. over about 2 hours. The slurry was aged at 20° C. for 1 h and then filtered. The cake was washed with 2-MeTHF (715 mL). The solids were dried in a vacuum oven for 24 h at 40° C. The final product 10 was isolated as a white solid (212 g, 86%). $^1$H NMR (400 MHz, CDCl$_3$) δ 4.07 (t, J=7.3 Hz, 1H), 3.44 (d, J=10.4 Hz, 1H), 3.35 (s, 1H), 3.10 (d, J=10.4 Hz, 1H), 2.03 (dd, J=12.3, 6.9 Hz, 1H), 1.89 (dd, J=12.3, 8.0 Hz, 1H), 1.38 (s, 9H), 0.71-0.27 (m, 4H). $^1$H NMR (400 MHz, d$_6$-DMSO, δ): 3.89 (dd, J=8.6, 4.1 Hz, 0.4H rotamer 1), 3.85 (dd, J=8.6, 4.3 Hz, 0.6H rotamer 2), 3.21-3.07 (m, 2H), 2.00-1.92 (m, 1H), 1.75-1.71 (m, 1H) 1.36 (s, 4H rotamer 1), 1.32 (s, 5H rotamer 2), 0.46-0.37 (m, 4H). $^{13}$C NMR (100 MHz, d$_6$-DMSO) δ 174.5, 174.4, 154.1, 153.4, 77.2, 76.9, 62.3, 62.0, 54.1, 53.8, 38.7, 28.4, 28.3, 20.6, 19.9, 11.8, 11.6, 10.5, 10.2.

II. Route to Intermediate 22

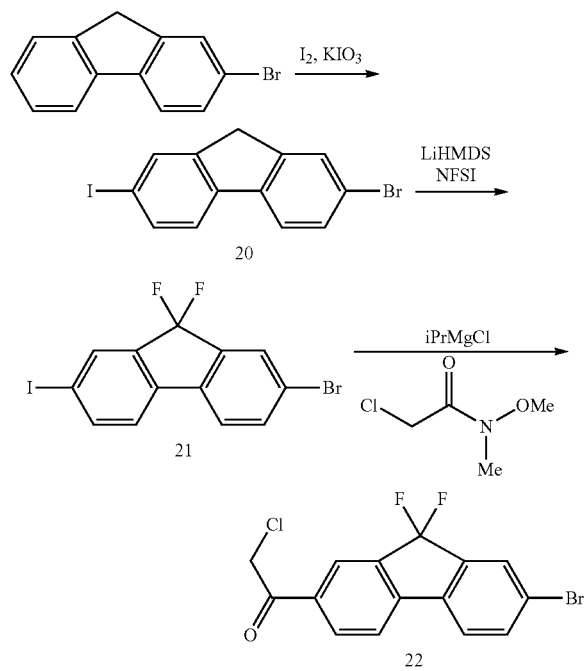

A. Synthesis of Intermediate 20

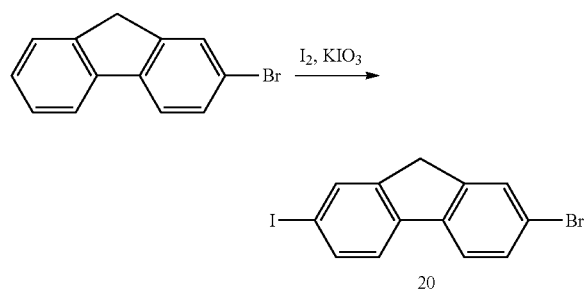 [SMILES: Brc1ccc2c(c1)Cc1ccccc1-2 ; Brc1ccc2c(c1)Cc1cc(I)ccc1-2]

A 3-neck flask was charged with 2-bromofluorene (100 g) and acetic acid (2100 g). The contents were heated to 40-45° C. and agitated for approximately 30 minutes to obtain a clear solution. After adjusting the internal temperature to 20-30° C., 20% (v/v) aq. $H_2SO_4$ (200 g, prepared with 64.0 g of $H_2SO_4$ and 136 g of water) was added, followed by $I_2$ (53.0 g, 0.512 mole equiv) followed by $KIO_3$ (17.5 g, 0.200 mole equiv). The slurry was heated at 58° C. (56-60° C.) for about 4 hours. The slurry was then cooled to 20-25° C. and a 9% $Na_2SO_3$ solution ($Na_2SO_3$, 47.0 g; water, 500 g) was charged to the reaction mixture while maintaining the internal temperature at 20-30° C. The slurry was agitated at 25° C. for 1 hour and filtered. The filter cake was rinsed with 85 wt % HOAc (200 g, prepared with 170 g of HOAc and 30 g of water), followed by water (200 g, 2.0 wt equiv). The filter cake was discharged and slurry-washed in water (1500 g) for about 1 hour, then filtered and rinsed with water until pH of the rinse is 6-7, and further rinsed with heptanes (200 g). The solids were dried under vacuum producing 143 g (95% yield, 96% AN purity by HPLC) of the product 20 as a white solid.

B. Synthesis of Intermediate 21

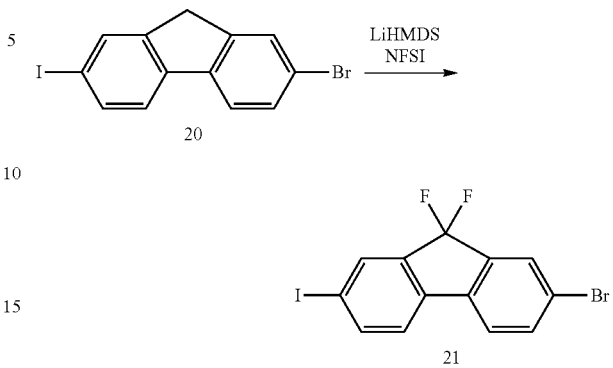

The starting material (20, 100 g) and N-fluorobenzenesulfonimide (NFSI, 251 g, 2.95 mole equiv) were added as solids to a flask. To the mixture was added THF (1000 g) and with stirring the solids dissolved. The solution was degassed three times by slowly applying vacuum, followed by breaking vacuum with nitrogen. The solution was cooled in a −78° C. bath to an internal temp of −68° C. Upon cooling, a white to off-white slurry was formed. A solution of the base (1.0M LiHMDS in THF, 720 g, 3.00 mole equiv) was added at such a rate that the internal temperature was kept below −55° C. The internal temp was <−60° C. for the majority of the addition, total addition time was about 1 h. The reaction completion was monitored by HPLC analysis. The reaction was quenched by the addition of $NH_3$/MeOH (7N $NH_3$ in MeOH, 8 g) and the cold bath was removed. After the internal temperature had warmed to −20° C., HPLC analysis showed complete consumption of the excess N-fluorobenzenesulfonimide. The internal temperature was adjusted to 0° C. Heptanes (342 g) was added and the solution stirred for 10 minutes. If necessary, the temperature was adjusted to 20-25° C. The slurry was filtered and the solids rinsed with a mixture of THF/heptanes twice (for each rinse: THF, 89.0 g; heptanes: 205 g). The filtrate was stored at 5° C. (2-8° C.) for ca. 20 hours. The solution was then filtered into a flask and concentrated to 2.5-3.0 volumes under vacuum at maximum internal temperature of 35° C. $CH_2Cl_2$ (1500 g) was charged and the slurry agitated at reflux (ca. 40° C.) for 30 minutes. After adjusting the internal temperature to 20-25° C., the slurry was filtered through a pad of celite, and the filter cake was rinsed with DCM (400 g, 4.0 wt equiv). The filtrate was concentrated to about 3.0 volumes under vacuum. Methanol (600 g,) was added and the mixture was concentrated to about 4.0 volumes, additional methanol (300 g) was added and the mixture was concentrated again to about 4.0 volumes (300 volumes). The slurry was filtered and rinsed with methanol twice (for each rinse, 100 g). The product 21 was dried under vacuum producing 90 g (82% yield, 97-98% AN purity by HPLC) of the product as an off-white to pale yellow solid. $^1$H NMR (400 MHz, $CDCl_3$, δ): 7.94 (d, J=1.2 Hz, 1H), 7.81 (d, J=7.8 Hz, 1H), 7.74 (d, J=1.4 Hz, 1H), 7.60 (d, J=8.3 Hz, 1H), 7.41 (d, J=8.1 Hz, 1H), 7.29 (d, J=8.0 Hz, 1H). $^{19}$F NMR (376 MHz, $CDCl_3$) δ −111.0 (s, 2F).

C. Synthesis of Intermediate 22

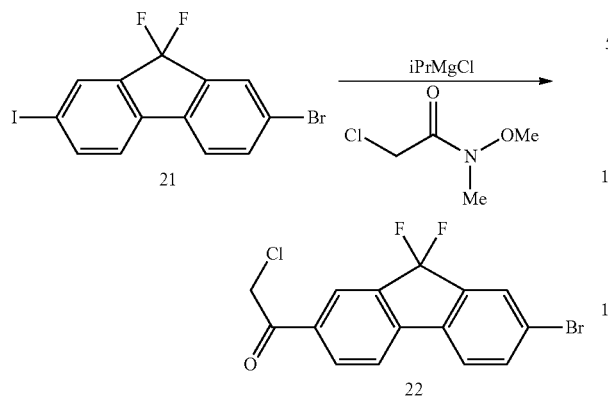

A 3-neck flask was charged with 21 (100 g) and THF (800 mL). The solution was degassed three times by slowly applying vacuum, followed by breaking vacuum with nitrogen. The solution was cooled to −10° C. internal temperature. A solution of 2N i-PrMgCl solution in THF (125 g, 1.04 mole equiv) was added slowly while maintaining internal temperature at −10° C. to 0° C. The resulting mixture was then stirred for 30 minutes at −10° C. until reaction was complete. 2-Chloro-N-methoxy-N-methylacetamide (40.6 g, 1.20 mole equiv) was dissolved in MTBE (122 g, 1.22 wt equiv) and filtered through a 1 µm filter. The MTBE solution of the acetamide was then added slowly to the flask maintaining internal temperature at −10° C. to 0° C. Upon completion of the addition, the internal temperature was adjusted to 0° C. and agitated for 2 hours. After the reaction is complete, 1N HCl (750 g) was added slowly so that the internal temperature did not exceed 20° C. If necessary, the internal temperature was adjusted to 20° C. The layers were separated and the aqueous layer was extracted with MTBE (410 g). The organic layers were combined and dried over MgSO$_4$. The MgSO$_4$ was filtered off and rinsed with THF (200 g). The filtrate and rinse were concentrated under vacuum 10 volumes (1000 mL). Isopropanol (785 g) was added and small amounts of crystals began to form. This slurry was again concentrated under vacuum to 10 volumes (1000 mL). Isopropanol (785 g) was once again added and the slurry was concentrated under vacuum to 10 volumes (1000 mL). The internal temperature was adjusted to 20-25° C. and agitated for ca. 30 minutes. The slurry was filtered and rinsed with isopropanol (100 g) then dried under vacuum to provide 62.28 g (70.8%, 98% purity by HPLC) of the product 22 as an off-white to pale yellow solid. $^1$H NMR (400 MHz, CDCl$_3$, δ): 8.19 (s, 1H), 8.12 (d, J=7.8 Hz, 1H), 7.82 (s, 1H), 7.67 (d, J=8.0 Hz, 2H), 7.52 (d, J=7.8 Hz, 1H), 4.71 (s, 2H). $^{19}$F NMR (376 MHz, CDCl$_3$) δ −111.4 (s, 2F).

III. Synthesis of Intermediate 24

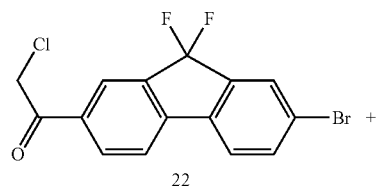

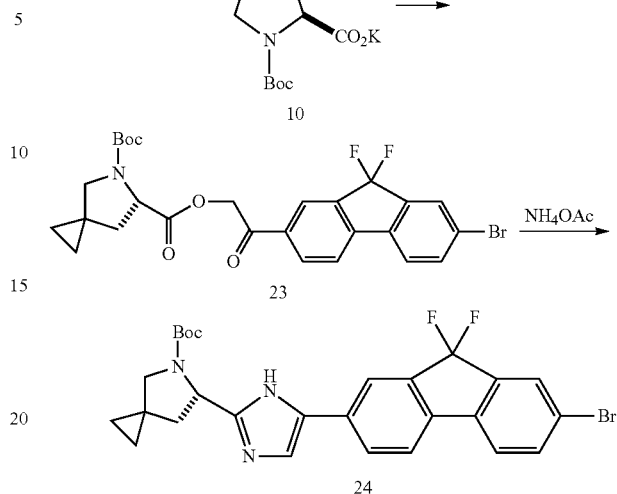

A. Preparation of 23

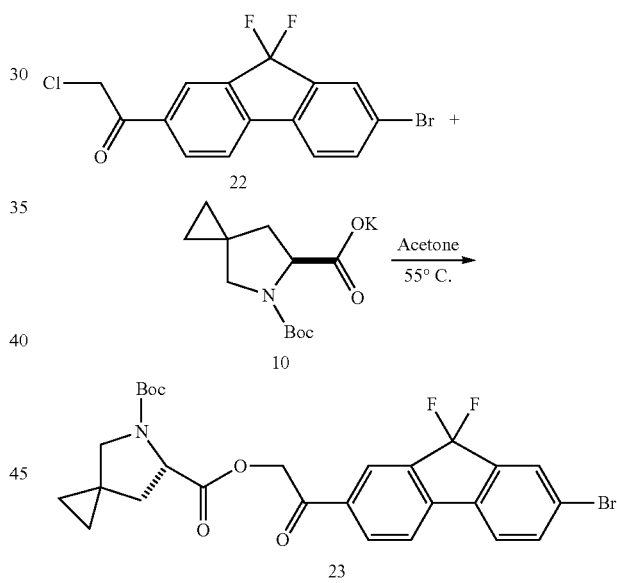

Compound 22 (10.8 g, 1.05 eq) and compound 10 (8.0 g, 1.0 eq) were dissolved in acetone (106 mL). The heterogeneous mixture was heated to 55° C. and aged until the reaction was deemed complete as determined by HPLC analysis. Water (22 mL) was added slowly and the solution was held at 55° C. for 30 minutes. The solution was cooled to 50° C. and seed crystals of 23 were added. Another portion of water (11 mL) was slowly added. The solution was aged at 50° C. for 1 h and then cooled to 20° C. (15-25° C.) over a period of 2 hours. The slurry was filtered at 20° C. (15-25° C.) and the filter cake was washed with a mixture of acetone (18 mL) and water (6 mL). The product was dried to afford 23 as a yellow solid (12.8 g, 95%). $^1$H NMR (400 MHz, CDCl$_3$, mixture of rotamers, δ): 8.13 (s, 1H), 8.07-7.97 (m, 1H), 7.79 (s, 1H), 7.67-7.56 (m, 2H), 7.53-7.44 (m, 1H), 5.61 (d, J=16.3 Hz, 0.5H), 5.47 (d, J=16.2 Hz, 0.5H), 5.29 (d, J=16.2 Hz, 0.5H), 5.15 (d, J=16.3 Hz, 0.5H), 4.62 (dd, J=8.7, 3.5 Hz, 0.5H), 4.55 (dd, J=8.7, 4.0 Hz, 0.5H), 3.48-3.28 (m, 2H), 2.43-2.35 (m, 1H), 2.17-2.07 (m, 1H), 1.48 (s, 9H) 0.77-0.55 (m, 4H); $^{13}$C NMR (100 MHz, CDCl$_3$) δ 190.8, 190.3, 172.2, 172.0, 154.4, 153.7, 143.7-143.4 (m), 140.3 (t, J=25.9 Hz), 138.2 (t, J=25.4 Hz), 136.9-136.5 (m), 135.5, 135.4, 134.7, 134.6, 132.4, 127.7, 124.2, 124.1, 123.2, 123.2, 122.7, 121.6 (t, J=244 Hz), 120.8, 120.8, 80.1, 80.0, 66.0, 65.9, 59.4, 59.0, 54.3, 53.7, 38.9, 38.0, 28.4, 28.3, 20.7, 20.0, 12.9, 12.3, 8.8, 8.3. $^{19}$F NMR (376 MHz, CDCl$_3$) δ −111.41 (s), −111.43 (s).

B. Imidazole 24 Formation

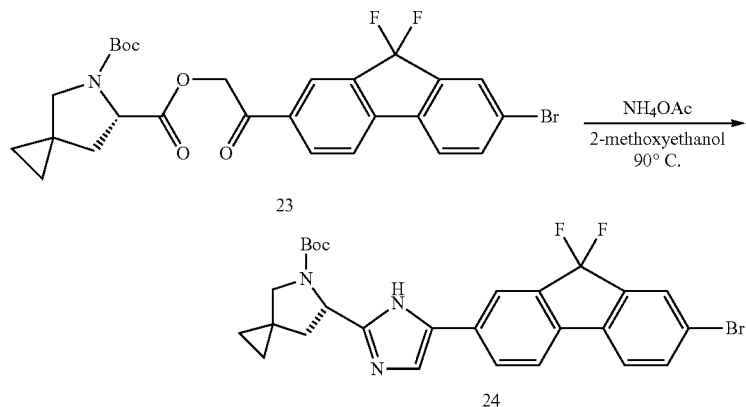

To compound 23 (7.0 g) and ammonium acetate (4.8 g, 5.0 eq) were added toluene (62 mL) and 2-methoxyethanol (3.5 mL). The heterogeneous/biphasic mixture was heated to 90° C. and aged until the reaction was deemed complete as determined by HPLC analysis. The solution was cooled to 55° C. and stirred until a slurry of 24 had formed (seeds can be added if necessary). Heptane (104 mL) was charged at 55° C. over 1 h and then the slurry was cooled to 22° C. over 3 h. Once the slurry had reached room temperature it was aged for 1 h. The slurry was filtered and washed with heptane (15 mL). The solids were then dissolved in DMAc (42 mL). The solution was heated to 45° C. and water (7 mL) was charged to the solution. The temperature of the solution was increased to 50° C. and seed crystals of 24 were charged. The slurry was aged for 30 min and then a second portion of water (9.1 mL) was charged over 1 h. Upon completion the slurry was cooled to 22° C. over 3 h and aged at room temperature for 1 h. The solids were filtered and washed with a DMAc (5 mL) and water (2 mL) solution. A final heptane (23 mL) wash was applied to displace the DMAc and water. The solids were dried at 45° C. in a vacuum oven. The final product 24 was isolated as a brown solid (5.2 g, 77%). $^1$H NMR (400 MHz, DMSO, mixture of rotomers, δ): 12.31-11.78 (m, 1H), 8.15-8.03 (m, 1H), 8.02-7.84 (m, 2H), 7.84-7.43 (m, 4H), 5.04-4.84 (m, 1H), 3.62-3.21 (m, 2H), 2.42-2.09 (m, 1H), 2.08-1.78 (m, 1H), 1.40 (s, 4H), 1.17 (s, 5H), 0.75-0.31 (m, 4H); $^{19}$F NMR (376 MHz, CDCl$_3$) δ −103.85 (s), −104.03 (s). MS-ESI$^+$: [M+H]$^+$ calcd for C$_{27}$H$_{27}$BrF$_2$N$_3$O$_2$, 542.1, 544.1. found, 542.1, 544.1.

IV. Synthesis of Intermediate 28

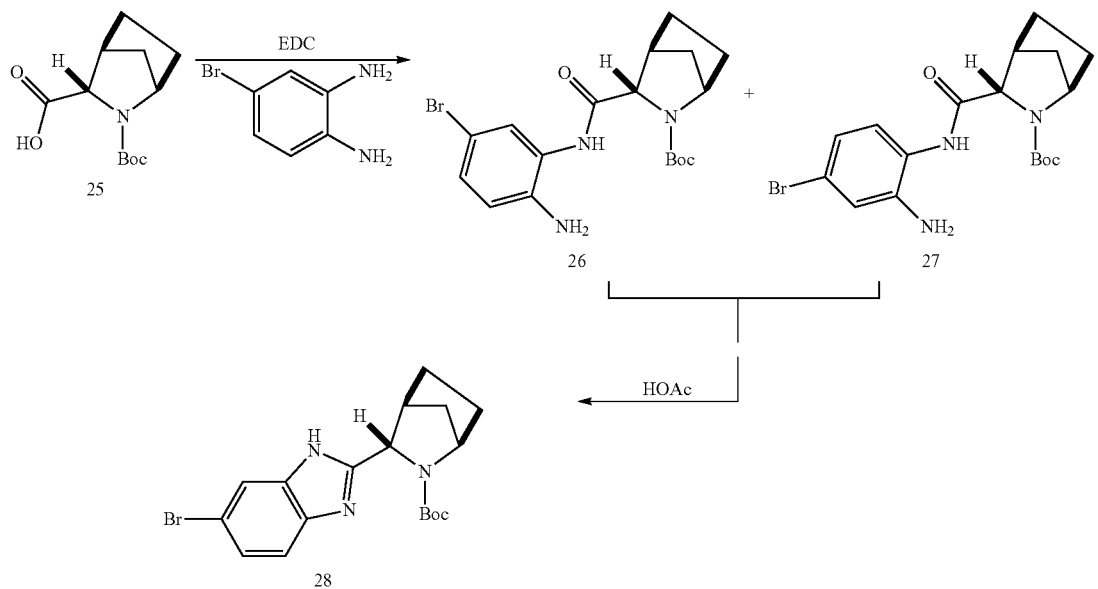

A. Synthesis of 25

B. Synthesis of 26 and 27

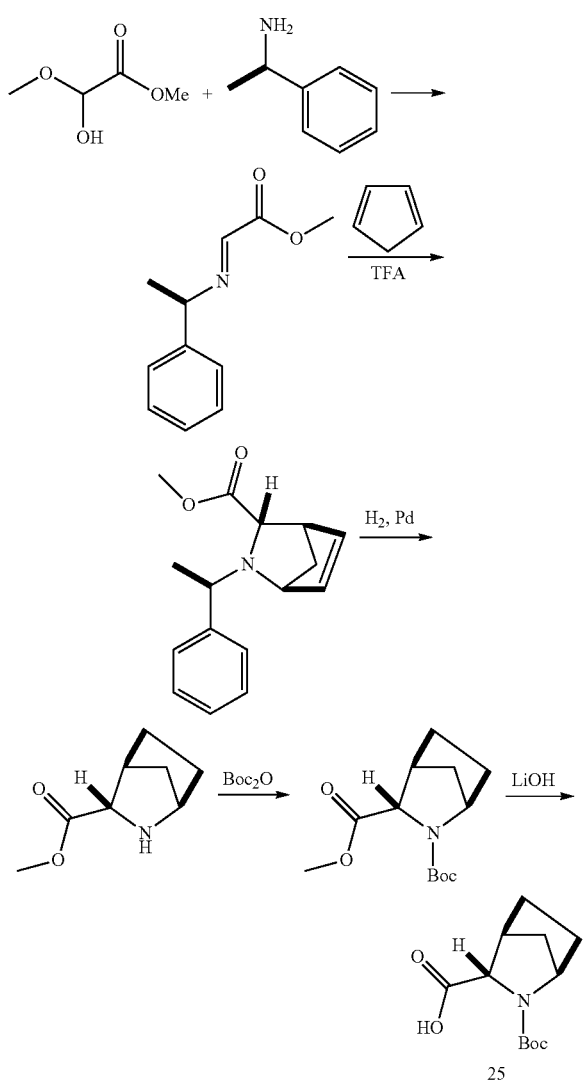

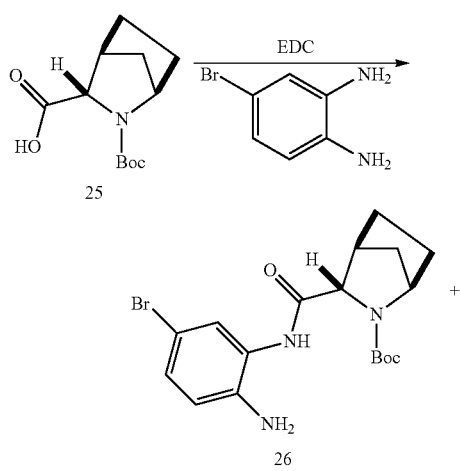

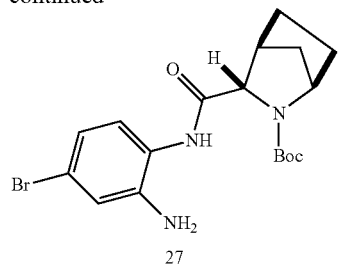

27

To a flask was charged 25 (20.00 g, 0.083 mol), 4-bromo-1,2-benzenediamine (16.74 g, 0.089 mol, 1.08 equiv.), hydroxybenzotriazole (HOBt) (13.96 g, 0.091 mol, 1.1 equiv.), and 1-ethyl-3-(3-dimethylaminopropyl) carbodiimide HCl (EDC-HCl) (17.48 g, 0.091 mol, 1.1 equiv.). The flask was cooled in an ice bath, and was charged with N,N-dimethylacetamide (DMAC, 80 mL). The reaction was allowed to cool to ca. 10° C. with stirring. N-methylmorpholine (NMM) (27.34 mL, 0.249 mol, 3 equiv.) was added over 5 minutes keeping the internal temperature below 20° C. The reaction was stirred at rt for 20 h. Upon reaction completion, the reaction mixture was added to MTBE (200 mL) and water (600 mL) in a reparatory funnel and was gently shaken. The layers were allowed to separate, and the aqueous layer was removed. The aqueous layer was extracted twice with MTBE (50 mL), and the organic extracts were combined. The combined organic extracts were then extracted with water (500 mL), forming a mixture that did not separate well. The mixture was filtered over an appropriate solid support and the layers were separated. The organic phase was concentrated under vacuum, and the resulting residue was dissolved in diisopropyl ether (100 mL). The solution was cooled to ca. 5° C. with stirring. Acetic acid (5.22 mL, 0.091 mol, 1.1 equiv.) was added slowly keeping the internal temperature below 10° C., and the resulting suspension was stirred 2 h at 5° C. The thick suspension was then filtered, and the solid was rinsed with diisopropyl ether (100 mL), followed by heptane (100 mL). The cake was dried under vacuum to give the product as a light-beige solid as a mixture of regioisomers 26 and 27 (28.19 g, 72%, >99% AN). $^1$H NMR (400 MHz, DMSO) mixture of 26 & 27 (data is for the two rotamers of the major regioisomer): δ 9.25 (s, 0.5H), 9.13 (s, 0.5H), 7.08 (d, J=8.3 Hz, 0.5H); 7.06 (d, J=8.2 Hz, 0.5H), 6.92 (d, J=2.2 Hz, 0.5H), 6.89 (d, J=2.1 Hz, 0.5H), 6.71 (dd, J=8.4, 2.2, 0.5H), 6.66 (dd, J=8.4, 2.2, 0.5H), 5.10 (br s, 1H), 5.05 (br s, 1H), 4.15 (br s, 0.5H), 4.10 (br s, 0.5H), 3.76 (s, 1H), 2.64 (br s, 1H), 1.96-1.88 (m, 1H), 1.77-1.67 (m, 1H), 1.67-1.19 (m, 4H), 1.41 (s, 4.5H), 1.33 (s, 4.5H). MS-ESI$^+$: [M+H]$^+$ calcd for $C_{18}H_{25}BrO_3N_3$, 410.1, 412.1. found, 410.0, 412.0

C. Synthesis of Intermediate 28

To a reactor was charged the 26/27 mixture (50.0 g, 0.106 mol). MTBE (200 mL, 4V) was charged and to the suspension was added glacial acetic acid (30.4 mL, 0.532 mol, 5 equiv.). The mixture was heated to 55° C. resulting in a brown, homogeneous solution, and was stirred at this temperature for 18 h. Upon reaction completion as determined by HPLC, the solution was cooled to ca. 10° C. and was then quenched with aqueous KOH (35 g in 200 mL H$_2$O) keeping the internal temperature below 20° C. The biphasic mixture was stirred vigorously for 15 min. Agitation was stopped and the layers were allowed to separate. The aqueous layer was drained and back-extracted again with MTBE (50 mL). The organic extracts were combined, H$_2$O (300 mL) was charged, and the biphasic mixture was stirred vigorously for 15 min. Agitation was stopped and the layers were allowed to separate. The aqueous layer was drained, and the tan organic layer was polish filtered. The solvent was distilled to a volume of ca. 50 mL. Diisopropyl ether (IPE, 150 mL) was added while keeping the internal temperature above 48° C. and the solution was distilled to a total volume of ca. 80 mL. IPE (150 mL) was again added and the solution was distilled to ca. 120 mL. This process was continued until the solvent was mainly diisopropyl ether as indicated by an internal temperature during distillation of about 69° C. or as determined by $^1$H NMR. The total volume was then adjusted to ca. 120 mL, and the solution was allowed to cool slowly (10° C./h) overnight to 0° C. resulting in slurry formation. The slurry was then filtered and rinsed with cold IPE (100 mL). The solids were collected and dried in a vacuum oven to give 28 (39.23 g, 94% yield, >99.5% AN). $^1$H NMR (400 MHz, CDCl$_3$, δ): 10.70 (s, 1H), 7.86 (s, 0.5H), 7.58 (d, J=8.6 Hz, 0.5H), 7.54 (s, 0.5H), 7.30 (d, 8.3 Hz, 1H), 7.25 (d, J=8.0 Hz, 0.5H), 4.52 (d, J=3.6 Hz, 1H), 4.15 (s, 1H), 3.43 (d, J=3.2 Hz, 1H), 2.03-1.94 (m, 1H), 1.93-1.81 (m, 1H), 1.80-1.55 (m, 4H), 1.52 (s, 9H). MS-ESI$^+$: [M+H]$^+$ calcd for C$_{18}$H$_{23}$BrO$_2$N$_3$, 392.1, 394.1. found, 392.1, 393.9

V. Synthesis of Amorphous Compound I from Intermediate 28

A. Formation of Compound 29

1a. Coupling of Compounds 28 and 24

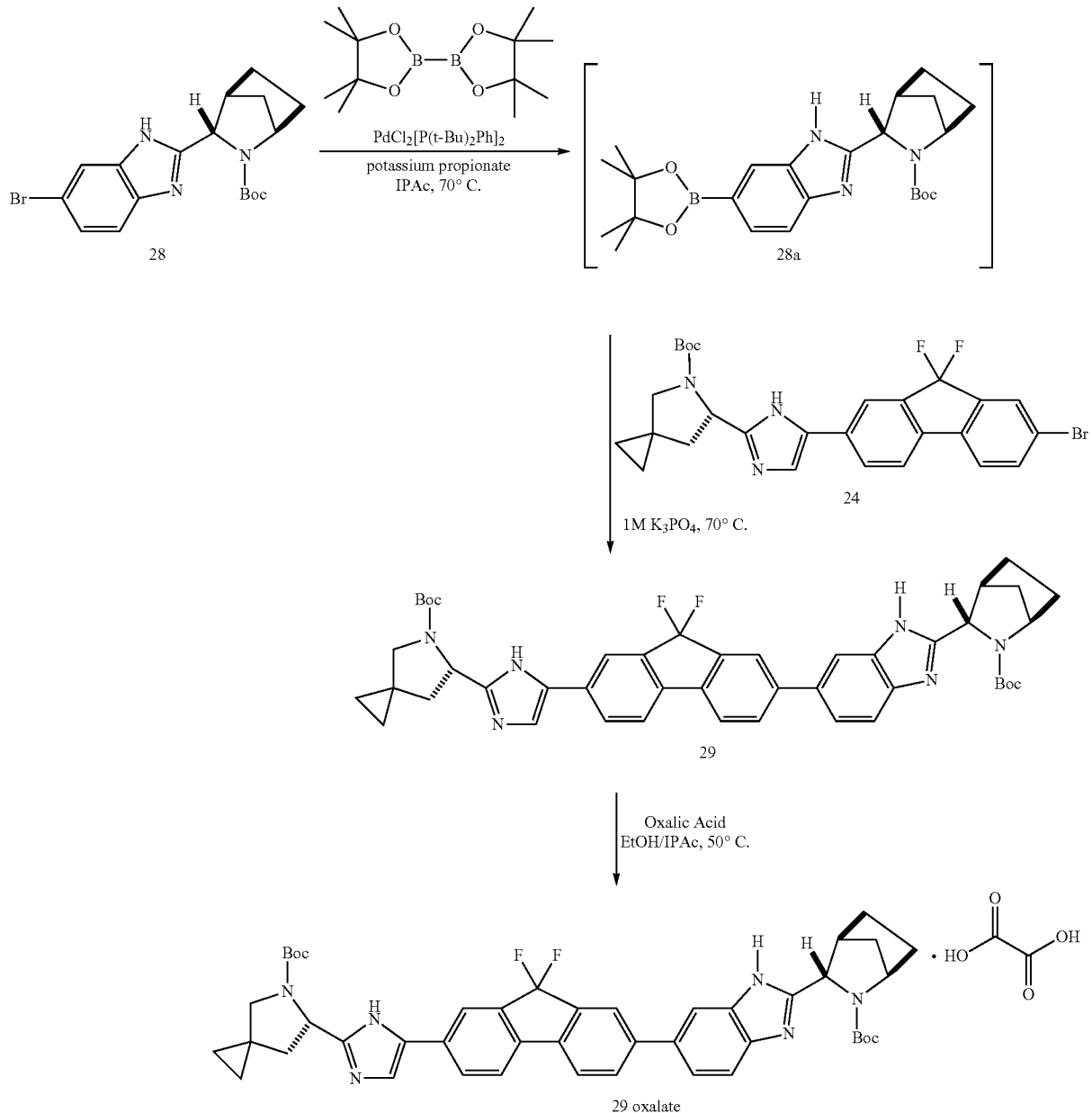

Compound 28 (24.98 g), bis(pinacolato)diboron (19.40 g), potassium propionate (21.40 g) and PdCl$_2$[P(t-Bu)$_2$Ph]$_2$ (2.04 g) were charged to a reactor, and the reactor was inerted. Isopropyl acetate (250 mL) was charged, stirring was initiated and the reactor was re-inerted. The reaction mixture was heated to 75° C. and agitated for 3.5 h. After cooling to 25° C., compound 24 (29.31 g) was charged to the reaction mixture, and the reactor was inerted.

Degassed aqueous 1M $K_3PO_4$ (223 mL) was charged to the reactor, and the reaction mixture was heated to 75° C. The reaction mixture was held at this temperature for 1 h and was then cooled to 35-40° C. N-Acetyl-L-cysteine (6.27 g) was charged, and the mixture was agitated at 35-40° C. for 15 h. The reaction mixture was cooled to 20° C., agitation was stopped and the layers were allowed to split. The phases were separated and N-acetyl-L-cysteine (6.27 g) was charged to the organic layer. The reaction mixture was heated to 45-50° C. After agitating the mixture at 45-50° C. for 2 h, the reaction was cooled to 20° C. and 5% aqueous NaOH (250 mL) was added. The phases were separated, and the organic layer was washed with 5% aqueous NaCl (125 mL). The organic phase was then treated with 5% aqueous NaCl (125 mL) and transferred to a separatory funnel via filtration through filter paper. The layers were separated. The organic phase was transferred to a reactor and concentrated to approximately 160 mL by vacuum distillation. iPrOAc (20 mL) was charged to bring the final volume to approx. 180 mL. Ethanol (100 mL) was charged, and the contents were heated to approximately 50° C. A solution of oxalic acid (9.3 g) in ethanol (40 mL) was then charged to the mixture. The solution was seeded with 29 oxalate (200 mg) and aged at 50° C. for 72 h. Isopropyl acetate (240 mL) was charged over 5 h, and the slurry was cooled to 15° C. over 4 h and stirred at this temperature for 20 h. The product was collected by filtration, washed with a solution of ethanol in isopropyl acetate (48 mL EtOH, 191 mL iPrAc) and dried under vacuum at 45° C. to provide 29 oxalate as an off-white solid (41.46 g, 81% yield). $^1$H NMR (400 MH, DMSO-$d_6$, δ) 11.80 (br s, 4H), 8.11 (d, J=1.2 Hz, 1H), 8.00 (d, J=9.2 Hz, 1H), 7.98 (s, 1H), 7.90 (s, 2H), 7.87, (d, J=9.2 Hz, 1H), 7.85 (s, 1H), 7.80 (s, 1H), 7.60 (dd, J=8.4, 1.2 Hz, 1H), 7.56 (dd, J=7.6, 1.6 Hz, 1H), 5.03 (m, 0.5H), 4.99 (m, 0.5H), 4.52 (s, 0.5H), 4.50 (s, 0.5H), 4.28 (br s, 0.5H), 4.19 (br s, 0.5H), 3.48 (m, 1H), 3.34 (m, 1H), 2.66 (br d, J=12.7 Hz, 1H), 2.38 (m, 0.5H), 2.26 (m, 0.5H), 2.04 (m, 1H), 1.96 (m, 0.5H), 1.86 (d, J=11.6 Hz, 0.5H), 1.77 (m, 1H), 1.70 (m, 1H), 1.64 (2H, m), 1.43 (s, 6H) 1.41 (s, 3H), 1.35 (m, 1H), 1.19 (s, 5H), 1.14 (s, 4H), 0.65 (m, 2H) 0.54 (m, 1H), 0.42 (m, 1H). HRMS-ESI$^+$: [M+H]$^+$ calcd for $C_{45}H_{49}O_4N_6F_2$, 775.3778. found, 775.3773.

B. Bis-Boc Deprotection of Compound 29

To a solution of 29 (92.5 g, 119 mmol) in MeCN (324 mL) at 65° C. was charged a 1.5 N aqueous HCl solution (398 mL, 5.0 mol equiv). The reaction mixture was agitated for about 2 h at 65° C. and monitored for completion by HPLC analysis. Upon determination of consumption of starting material, the temperature of the reaction mixture was adjusted to 45° C. Acetonitrile (648 mL) was charged over a course of ≥30 min in order to maintain an internal temperature of 40-50° C. Upon completion of this anti-solvent addition, seed crystals of 30 hydrochloride salt were charged (0.103 g). The slurry was aged at 45° C. for ≥1 h. Additional MeCN (1480 mL) was charged over a course of ≥30 min in order to maintain an internal temperature of 40-50° C. The slurry was cooled to 20° C. over ≥2 h and then filtered. The wet cake was dried to provide 84.6 g of 30 (as its tetra-HCl salt, also including ~6% $H_2O$ content, 80.4% yield). Typical water content ranges from about 4 to about 13%. $^1$H NMR (400 MHz, DMSO-$d_6$, δ): 10.83 (br s, 2H), 10.44 (br s, 2H), 10.33 (br s, 1H), 9.33 (br s, 1H), 8.37 (s, 1H), 8.36 (s, 1H), 8.26 (d, J=8.0 Hz, 1H), 8.08 (d, J=0.8 Hz, 1H), 8.06 (d, J=8.0 Hz, 1H), 8.03 (d, J=0.8 Hz, 1H), 8.01 (d, J=8.4 Hz, 1H), 7.98 (dd, J=8.0, 1.2 Hz, 1H), 7.79 (dd, J=8.4, 0.4 Hz, 1H), 7.75 (dd, J=8.4, 1.2 Hz, 1H), 5.29 (dd, J=8.0, 7.6 Hz, 1H), 4.82 (d, J=3.6 Hz, 1H), 4.19 (s, 1H), 3.65 (d, J=10.8 Hz, 1H), 3.14 (s, 1H), 3.12 (d, J=10.8 Hz, 1H), 2.85 (dd, J=13.2, 9.6 Hz, 1H), 2.23 (dd, J=12.8, 7.6 Hz, 1H), 2.11 (m, 1H), 1.99 (d, J=11.2 Hz, 1H), 1.83 (m, 1H), 1.76 (m, 1H), 1.71 (d, J=10.8 Hz, 1H), 1.67 (m, 1H), 0.84 (m, 2H), 0.70 (m, 2H). HRMS-ESI$^+$: [M+H]$^+$ calcd for $C_{35}H_{33}N_6F_2$, 575.2729. found, 575.2729.

Compound 30 was isolated as a crystalline solid from a mixture of $CH_3CN$ and aq. HCl.

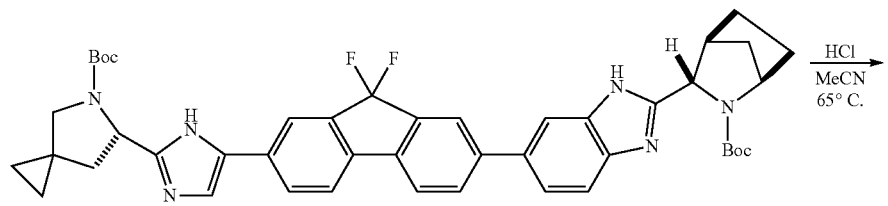

29

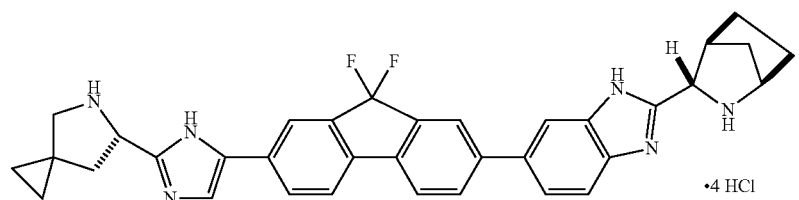

30

C. Amide Coupling

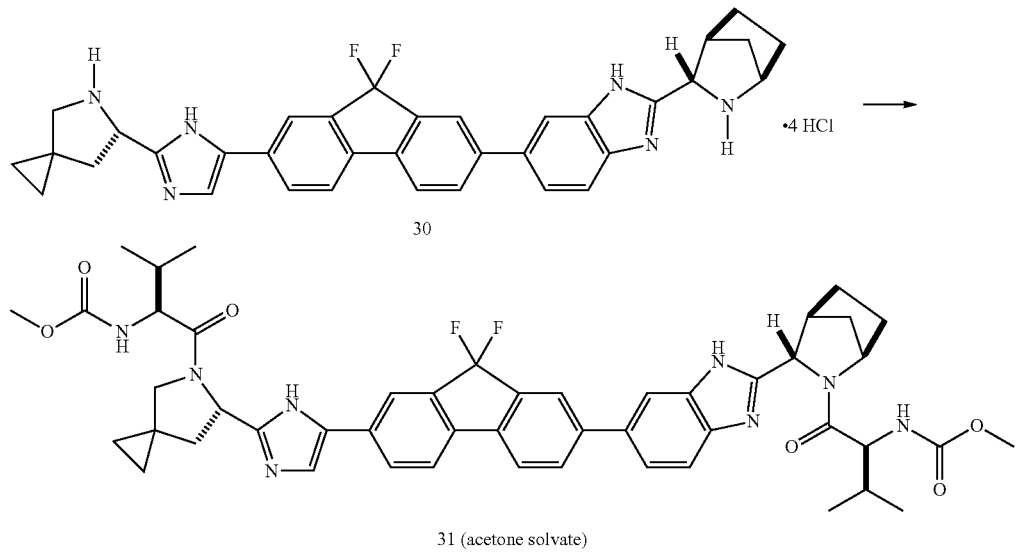

EDC-HCl (4.39 g), HOBt (2.06 g), Moc-Valine (4.02 g), and DMF (50 mL) were charged to a flask. The reaction mixture was agitated for 20 min at 23° C. The solution was then cooled to 0° C. 30-HCl salt (5.0 g) and N-methylmorpholine (5.03 mL) were charged to the reaction mixture. The contents were warmed to room temperature and stirred for 4 hours at 23° C. Water (2.5 mL) was added to the reaction mixture and the contents were stirred for 15 hours at 23° C. EtOAc (70 mL) and water (100 mL) were added and the layers were separated. To the organic layer was added EtOAc (50 mL) and water (50 mL), the layers mixed and then separated. The organic layer was washed with 5% $NaHCO_3$ (50 mL) and water (2×25 mL). The organic layer was then distilled to 2.5 vols (12.5 mL) and cooled to 23° C. Acetone (70 mL) was added to the organic layer. The reaction contents were seeded with compound 31 (acetone solvate) and stirred for 15 hours. The contents were filtered, the wet cake was washed with acetone (5 mL) and the cake was dried to provide 4.78 g of 31 as the acetone solvate (73%). $^1H$ NMR (400 MHz, DMSO-$d_6$, δ): 12.29 (s, 0.1H), 12.19 (d, J=4.0 Hz, 1H), 12.14 (s, 0.2H), 11.85 (s, 1H), 8.10 (s, 0.1H), 8.08 (s, 1H), 8.01 (s, 0.1H), 7.963 (m, 1H), 7.955 (s, 1H), 7.89 (d, J=6.4 Hz, 1H), 7.87 (s, 1H), 7.83 (dd, J=8.4, 2.4 Hz, 1H), 7.79 (dd, J=7.2, 2.8 Hz, 1H), 7.78-7.90 (misc., 0.9H), 7.70 (s, 1H), 7.61 (d, J=8.4 Hz, 1H), 7.55 (s, 1H), 7.51 (dd, J=8.8, 1.6 Hz, 1H), 7.44 (m, 0.1H), 7.31 (d, J=8.4 Hz, 1H), 7.21 (d, J=8.4 Hz, 1H), 6.91 (d, J=8.0 Hz, 0.2H), 6.77 (m, 0.2H), 5.34 (d, J=7.6 Hz, 0.1H), 5.20 (dd, J=8.0, 5.2 Hz, 1H), 5.18 (m, 0.1H), 4.88 (s, 0.1H), 4.67 (d, J=6.4 Hz, 1H), 4.55 (s, 1H), 4.17 (dd, J=8.0, 8.0 Hz, 1H), 4.10 (m, 0.2H), 4.01 (dd, J=8.4, 8.0 Hz, 1H), 3.97 (m, 0.1H), 3.82 (d, J=9.6 Hz, 1H), 3.77 (s, 0.2H), 3.71 (d, J=9.6 Hz, 1H), 3.554 (s, 3H), 3.548 (s, 3H), 3.43 (s, 0.4H), 3.20 (d, J=7.6 Hz, 0.3H), 2.77 (s, 0.1H), 2.66 (s, 1H), 2.41 (d, J=8.8 Hz, 1H), 2.22 (dd, J=12.4, 8.0 Hz, 1H), 2.13 (m, 0.4H), 2.08 (s, 6H), 2.05 (dd, J=13.2, 5.2 Hz, 1H), 1.99 (m, 2H), 1.92 (m, 1H), 1.77 (m, 2H), 1.61 (m, 0.3H), 1.56 (m, 1H), 1.46 (d, J=9.2 Hz, 1H), 1.33 (d, J=10.0 Hz, 0.1H), 0.97 (dd, J=6.4, 2.0 Hz, 3H), 0.93 (d, J=6.8 Hz, 3H), 0.88 (d, J=6.4 Hz, 3H), 0.87 (d, J=6.4 Hz, 3H), 0.80-1.05 (misc., 2H), 0.70 (m, 1H), 0.59 (m, 2H), 0.54 (m, 1H), 0.33 (m, 0.1H). HRMS-ESI$^+$: [M+H]$^+$ calcd for $C_{49}H_{55}O_6N_8F_2$, 889.4207. found, 889.4205.

C. Isolation of Amorphous Compound I

The acetone solvate of Compound I, Compound 31 (191.4 g), was combined with acetonitrile (1356 g) in a reaction vessel and mixed until a solution was formed. This solution was slowly added to another reaction vessel containing vigorously agitated water (7870 g). The combined reaction mixture was agitated at about 23° C. for about 30 minutes. The solid was then filtered and dried at about 40-45° C. to afford amorphous Compound I (146.4 g, 82% yield).

Example 11

Formulations of Amorphous Compound I

Tablets containing 1 mg and 10 mg of amorphous Compound I (free base) were prepared using wet and dry granulation processes as discussed below.

High-Shear Wet Granulation Process

Wet granulated formulations contained commonly used excipients, and included fillers (lactose and microcrystalline cellulose), a disintegrant, a binder, and a lubricant. Compositions of the formulations prepared by a high shear wet granulation process are presented in Table 25.

TABLE 25

Quantitative Composition of amorphous Compound I 10 mg Tablets

| Ingredient | Unit Formula | |
|---|---|---|
| | (% w/w) | (mg/tablet) |
| Compound I (Amorphous Free Base) | 0.0-80.0 | 0.0-200.0 |
| Lactose Monohydrate | 0.0-80.0 | 0.0-200.0 |
| Microcrystalline Cellulose | 0.5-10.0 | 1.25-25.0 |
| Crospovidone | 0.0-5.0 | 0.0-12.5 |
| Copovidone | 0.0-5.0 | 0.0-12.5 |
| Poloxamer 188 Micro | 0.0-5.0 | 0.012.5 |
| Cremaphor EL | 0.0-2.0 | 0.0-5.0 |
| Magnesium Stearate | 100 | 250 |
| Total Core Weight | 0.0-80.0 | 0.0-200.0 |

Dry Granulation Process

Dry granulation formulations were also evaluated, and their compositions are presented in Table 26. Oral bioavailability of the amorphous Compound I from dry granulations was equivalent to a surfactant containing wet granulation formulation. Typical excipients were used in the dry granulation process, and included lactose and microcrystalline cellulose as fillers, a disintegrant, and a lubricant. Anhydrous lactose was used instead of the more typical lactose monohydrate to minimize the presence of water in close proximity with the amorphous free base. Chemical and physical stability of the lead formulation were acceptable, as well as all powder blend uniformity and tablet metrics.

TABLE 26

Quantitative Composition of amorphous Compound I 10 mg Tablets

| Ingredient | (% w/w) | Unit Formula (mg/tablet) |
| --- | --- | --- |
| Compound I (Amorphous Free Base) | 4.0 | 10.0 |
| Lactose Anhydrous | 0.0-80.0 | 0.0-200.0 |
| Microcrystalline Cellulose | 0.0-80.0 | 0.0-200.0 |
| Crospovidone | 0.0-10.0 | 0.0-25.0 |
| Copovidone | 0.0-5.0 | 0.0-12.5 |
| Poloxamer 188 Micro | 0.0-5.0 | 0.0-12.5 |
| Croscarmellose Sodium | 0.0-8.0 | 0.0-20.0 |
| Magnesium Stearate | 0.0-2.0 | 0.0-5.0 |
| Total Core Weight | 100 | 250 |

Further, amorphous Compound II mg and 10 mg tablets were film-coated with hypromellose-based Opardy White YS-1-18202A and their compositions are presented in Table 27.

TABLE 27

Quantitative Composition of amorphous Compound I 1 mg and 10 mg Tablets

| | 1 mg Tablet | | 10 mg Tablet | |
| --- | --- | --- | --- | --- |
| Ingredient | % w/w | Unit Formula (mg/tablet) | % w/w | Unit Formula (mg/tablet) |
| Compound I (Amorphous Free Base) | 0.40 | 1.0 | 4.00 | 10.0 |
| Lactose Anhydrous | 50.0-75.0 | 175.25 | 50.0-75.0 | 166.25 |
| Microcrystalline Cellulose | 0.0-35.0 | 62.5 | 0.0-35.0 | 62.5 |
| Croscarmellose Sodium | 0.0-5.0 | 7.5 | 0.0-5.0 | 7.5 |
| Magnesium Stearate | 0.0-2.0 | 3.75 | 0.0-2.0 | 3.75 |
| Total Tablet Core Weight | 100.0 | 250.0 | 100.0 | 250.0 |
| Opadry White YS-1-18202-A | 3.0-5.0 | 12.5 | 3.0-5.0 | 12.5 |
| Total Coated Tablet Weight | | 262.5 | | 262.5 |

Example 12

Formulations of Compound I D-tartrate

Tablets containing 10 mg of Compound I D-tartrate were prepared using the dry granulation process as discussed below.

Dry Granulation Process

An important aspect of the process that was critical to maintain was a high speed conical milling step, which was necessary to disperse small but relatively hard agglomerates of Compound I D-tartrate. The milling procedure was also employed to maintain acceptable blend and tablet content uniformity given the relatively low drug load of the tablets. Further, Compound I D-tartrate 10 mg tablets were film-coated with hypromellose-based Opardy White YS-1-18202A and their compositions are presented in Table 28.

TABLE 28

Quantitative Composition of Compound I D-tartrate 10 mg Tablets

| | 10 mg Tablet | |
| --- | --- | --- |
| Ingredient | % w/w | Unit Formula (mg/tablet) |
| Compound I D-tartrate | 0.40-8.0 | 11.7 |
| Lactose Monohydrate | 50.0-75.0 | 129.3 |
| Microcrystalline Cellulose | 0.0-35.0 | 50.0 |
| Croscarmellose Sodium | 0.0-5.0 | 6.0 |
| Magnesium Stearate | 0.0-2.0 | 3.0 |
| Total Tablet Core Weight | 100.0 | 200.0 |
| Opadry White YS-1-18202-A | 5.0 | 10 |
| Total Coated Tablet Weight | | 210.0 |

Tablets containing 10 mg of Compound I D-tartrate with a different composition than the one described in Table 28 and tablets containing 30 mg of Compound I D-tartrate were prepared using the above-described dry granulation process. Their compositions are presented in Table 29.

TABLE 29

Quantitative Composition of Compound I D-tartrate 10 mg and 30 mg Tablets

| | 10 mg Tablet | | 30 mg Tablet | |
| --- | --- | --- | --- | --- |
| Ingredient | % w/w | Unit Formula (mg/tablet) | % w/w | Unit Formula (mg/tablet) |
| Compound I D-tartrate Salt | 0.40-8.0 | 11.7 | 0.40-8.0 | 35.1 |
| Lactose Monohydrate | 50.0-75.0 | 408.3 | 50.0-75.0 | 384.9 |
| Microcrystalline Cellulose | 0.0-35.0 | 150.0 | 0.0-35.0 | 150.0 |
| Croscarmellose Sodium | 0.0-5.0 | 18.0 | 0.0-5.0 | 18.0 |
| Magnesium Stearate | 0.0-2.0 | 12.0 | 0.0-2.0 | 12.0 |
| Total Tablet Core Weight | 100.0 | 600.0 | 100.0 | 600.0 |
| Opadry White YS-1-18202-A | 5.00 | 30.0 | 5.00 | 30.0 |
| Total Coated Tablet Weight | | 630.0 | | 630.0 |

Polarized light microscopy (PLM) data were acquired for most of the Compound I forms described herein. For example, PLM data for Forms I, IV, VI, VII, IX, X, XI, and XII confirmed that each of the forms exists as a crystalline solid.

We claim:

1. Crystalline (1-{3-[6-(9,9-difluoro-7-{2-[5-(2-methoxy-carbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester diacetone solvate (Compound I Form I) characterized by an X-ray powder diffractogram comprising the following peaks: 6.8, 12.5, and 19.8 °2θ±0.2 °2θ, as determined on a diffractometer using Cu—Kα radiation at a wavelength of 1.54178 Å.

2. Compound I Form I according to claim 1, wherein the diffractogram further comprises peaks at 10.2, 11.1, and 23.8 °2θ±0.2 °2θ.

3. Compound I Form I according to claim 1, wherein the diffractogram is substantially as shown in FIG. 2.

4. Compound I Form I according to claim 1, characterized by a differential scanning calorimetry (DSC) curve that comprises a minor endotherm at about 124° C. and a major endotherm at about 162° C.

5. Compound I Form 1 according to claim 4, wherein the DSC curve is substantially as shown in FIG. 3.

6. Crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester monoacetone solvate (Compound I Form II) characterized by an X-ray powder diffractogram comprising the following peaks: 12.2, 12.7, and 20.5 °2θ±0.2 °2θ, as determined on a diffractometer using Cu—Kα radiation at a wavelength of 1.54178 Å.

7. Compound I Form II according to claim 6, wherein the diffractogram further comprises peaks at 7.5, 11.4, and 20.0 °2θ±0.2 °2θ.

8. Compound I Form II according to claim 6, wherein the diffractogram is substantially as shown in FIG. 4.

9. Compound I Form II according to claim 6, characterized by a differential scanning calorimetry (DSC) curve that comprises an endotherm at about 130° C.

10. Compound I Form H according to claim 9, wherein the DSC curve is substantially as shown in FIG. 5.

11. A pharmaceutical composition comprising a compound of Compound I Form I according to claim 1, or Compound I Form II according to claim 6, and a pharmaceutically acceptable excipient.

12. A method for treating a subject suffering from hepatitis C virus (HCV), comprising administering to the subject a therapeutically effective amount of Compound I Form I according to claim 1, or Compound I Form II according to claim 6.

13. The method according to claim 12, comprising further administering to the subject at least one anti-HCV agent.

14. The method according to claim 13, wherein the anti-HCV agent is a compound selected from the group consisting of ribavirin,

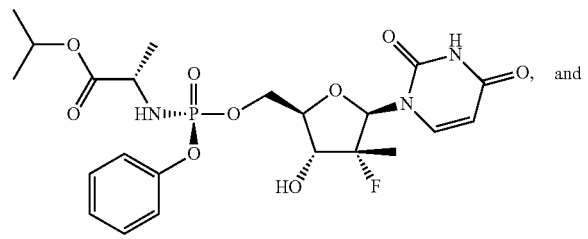

and

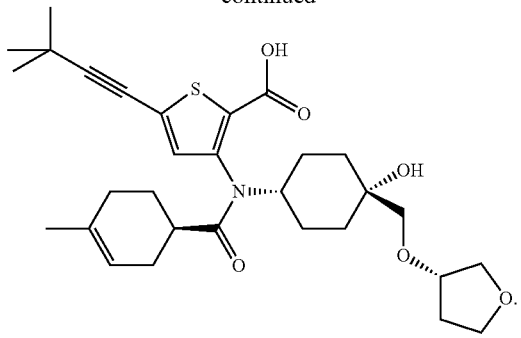

15. A process for making crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl -propyl)-carbamic acid methyl ester diacetone solvate (Compound I Form I) characterized by an X-ray powder diffractogram comprising the following peaks: 6.8, 12.5, and 19.8 °2θ±0.2 °2θ, as determined on a diffractometer using Cu-Kα radiation at a wavelength of 1.54178 Å, comprising the step of
  (1) contacting amorphous (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester with acetone,
whereby Compound I Form I is formed.

16. The process according to claim 15, further comprising the step of
  (2) isolating Compound I Form I.

17. A process for making crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester monoacetone solvate (Compound I Form II) characterized by an X-ray powder diffractogram comprising the following peaks: 12.2, 12.7, and 20.5°2θ±0.2 °2θ, as determined on a diffractometer using Cu—Kα radiation at a wavelength of 1.54178 Å, comprising the step of:
  (1) partially desolvating crystalline (1-{3-[6-(9,9-difluoro-7-{2-[5-(2-methoxycarbonylamino-3-methyl-butyryl)-5-aza-spiro[2.4]hept-6-yl]-3H-imidazol-4-yl}-9H-fluoren-2-yl)-1H-benzoimidazol-2-yl]-2-aza-bicyclo[2.2.1]heptane-2-carbonyl}-2-methyl-propyl)-carbamic acid methyl ester diacetone solvate (Compound I Form I) characterized by an X-ray powder diffractogram comprising the following peaks: 6.8, 12.5, and 19.8 °2θ±0.2 °2θ, as determined on a diffractometer using Cu—Kα radiation at a wavelength of 1.54178 Å,
whereby Compound I Form II is formed.

* * * * *